US012247078B2

(12) United States Patent
Throsby et al.

(10) Patent No.: US 12,247,078 B2
(45) Date of Patent: *Mar. 11, 2025

(54) ERBB-2 AND ERBB-3 BINDING BISPECIFIC ANTIBODIES FOR USE IN THE TREATMENT OF CELLS THAT HAVE AN NRG1 FUSION GENE

(71) Applicant: Merus N.V., Utrecht (NL)

(72) Inventors: Mark Throsby, Utrecht (NL); Cecilia Anna Wilhelmina Geuijen, Utrecht (NL); David Andre Baptiste Maussang-Detaille, Utrecht (NL); Ton Logtenberg, Utrecht (NL)

(73) Assignee: Merus N.V., Utrecht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/583,481

(22) Filed: Feb. 21, 2024

(65) Prior Publication Data

US 2024/0182587 A1    Jun. 6, 2024

Related U.S. Application Data

(60) Continuation of application No. 18/449,460, filed on Aug. 14, 2023, which is a division of application No. 16/499,185, filed as application No. PCT/NL2018/050206 on Apr. 3, 2018, now Pat. No. 11,780,925.

(30) Foreign Application Priority Data

Mar. 31, 2017  (EP) .................................... 17164292

(51) Int. Cl.
*C07K 16/28* (2006.01)
*C07K 16/46* (2006.01)

(52) U.S. Cl.
CPC ........ *C07K 16/2863* (2013.01); *C07K 16/468* (2013.01); *C07K 2317/21* (2013.01); *C07K 2317/31* (2013.01); *C07K 2317/52* (2013.01)

(58) Field of Classification Search
None
See application file for complete search history.

(56) References Cited

U.S. PATENT DOCUMENTS

| | | | |
|---|---|---|---|
| 4,801,687 A | 1/1989 | Ngo | |
| 4,816,567 A | 3/1989 | Cabilly et al. | |
| 5,151,504 A | 9/1992 | Croze | |
| 5,731,168 A | 3/1998 | Carter et al. | |
| 7,642,228 B2 | 1/2010 | Carter et al. | |
| 7,705,103 B2 | 4/2010 | Sherman et al. | |
| 8,349,574 B2 | 1/2013 | Bates et al. | |
| 8,592,562 B2 | 11/2013 | Kannan et al. | |
| 8,628,774 B2 | 1/2014 | Gurney et al. | |
| 9,220,775 B2 | 12/2015 | Chowdhury et al. | |
| 9,248,181 B2 | 2/2016 | De Kruif et al. | |
| 9,248,182 B2 | 2/2016 | De Kruif et al. | |
| 9,358,286 B2 | 6/2016 | De Kruif et al. | |
| 9,551,208 B2 | 1/2017 | Ma et al. | |
| 9,758,805 B2 | 9/2017 | De Kruif et al. | |
| 9,914,777 B2 | 3/2018 | Bakker et al. | |
| 9,968,676 B2 | 5/2018 | Adler et al. | |
| 10,208,354 B2 | 2/2019 | Fernandez-Cuesta et al. | |
| 10,358,492 B2 | 7/2019 | Bakker et al. | |
| 10,416,162 B2 | 9/2019 | Huang et al. | |
| 10,844,127 B2 | 11/2020 | Logtenberg et al. | |
| 11,780,925 B2 | 10/2023 | Throsby et al. | |
| 2003/0078385 A1 | 4/2003 | Arathoon et al. | |
| 2004/0071696 A1 | 4/2004 | Adams et al. | |
| 2006/0212956 A1 | 9/2006 | Crocker et al. | |
| 2009/0181022 A1 | 7/2009 | Nielsen et al. | |
| 2009/0182127 A1 | 7/2009 | Kjaergaard et al. | |
| 2009/0191559 A1 | 7/2009 | Huang et al. | |
| 2010/0015133 A1 | 1/2010 | Igawa et al. | |
| 2010/0183615 A1 | 7/2010 | Kufer et al. | |
| 2010/0286374 A1 | 11/2010 | Kannan et al. | |
| 2011/0077163 A1 | 3/2011 | Doranz | |
| 2011/0195454 A1 | 8/2011 | Mcwhirter et al. | |
| 2012/0107234 A1 | 5/2012 | Pedersen et al. | |
| 2012/0107306 A1 | 5/2012 | Elis et al. | |
| 2012/0270801 A1 | 10/2012 | Frejd et al. | |
| 2012/0328623 A1 | 12/2012 | Takahashi | |
| 2013/0071859 A1 | 3/2013 | Bates et al. | |
| 2013/0084297 A1 | 4/2013 | Daly et al. | |

(Continued)

FOREIGN PATENT DOCUMENTS

AU   2014212081 A1   8/2015
EP   0120694 A2   10/1984

(Continued)

OTHER PUBLICATIONS

Adelaïde, J., et al., "A Recurrent Chromosome Translocation Breakpoint in Breast and Pancreatic Cancer Cell Lines Targets the Neuregulin/NRG1 Gene," Genes Chromosome Cancer, 37(4):333-345, Wiley-Liss, Inc, United States (Aug. 2003).

Agus, D.B., et al., "Targeting ligand-activated ErbB2 signaling inhibits breast and prostate tumor growth," Cancer Cell, 2(2):127-137, Cell Press, United States (Aug. 2002).

Balko, J.M., et al., "The receptor tyrosine kinase ErbB3 maintains the balance between luminal and basal breast epithelium," PNAS, 109(1):221-226, U.S. National Academy of Science, United States (Jan. 2012).

Birnbaum, D., et al., "Chromosome arm 8p and cancer: a fragile hypothesis," The Lancet Oncology, 4:639-642, Elsevier, Netherlands (Oct. 2003).

Chua, Y.L., et al., "The NRG1 gene is frequently silenced by methylation in breast cancers and is a strong candidate for the 8p tumor suppressor gene," Oncogene, 28(46):4041-4052, Macmillan Publishers Limited, Germany (Nov. 2009).

(Continued)

*Primary Examiner* — Ruixiang Li
(74) *Attorney, Agent, or Firm* — Sterne, Kessler, Goldstein & Fox P.L.L.C.

(57) ABSTRACT

The invention relates to the field of antibodies. In particular it relates to the field of therapeutic (human) antibodies for the treatment of ErbB-2/ErbB-3 positive cells. More in particular it relates to treating of cells comprising an NRG1 fusion gene comprising at least a portion of the NRG1-gene fused to a sequence from a different chromosomal location.

20 Claims, 10 Drawing Sheets

Specification includes a Sequence Listing.

(56) References Cited

U.S. PATENT DOCUMENTS

| | | |
|---|---|---|
| 2013/0115208 A1 | 5/2013 | Ho et al. |
| 2013/0156779 A1 | 6/2013 | Clarke et al. |
| 2013/0185821 A1 | 7/2013 | Babb et al. |
| 2013/0251703 A1 | 9/2013 | Elis et al. |
| 2013/0259867 A1 | 10/2013 | Amler et al. |
| 2013/0336885 A1 | 12/2013 | Hongo et al. |
| 2013/0336981 A1 | 12/2013 | De Kruif et al. |
| 2013/0344093 A1 | 12/2013 | Daly et al. |
| 2014/0056898 A1 | 2/2014 | Zhang et al. |
| 2014/0072579 A1 | 3/2014 | De Kruif et al. |
| 2014/0120096 A1 | 5/2014 | Bakker et al. |
| 2014/0140999 A1 | 5/2014 | De Kruif et al. |
| 2014/0141019 A1 | 5/2014 | Kharrat et al. |
| 2014/0302020 A1 | 10/2014 | Tremblay et al. |
| 2014/0378664 A1 | 12/2014 | Suh et al. |
| 2015/0013996 A1 | 1/2015 | Davies et al. |
| 2015/0139996 A1 | 5/2015 | De Kruif et al. |
| 2015/0196637 A1 | 7/2015 | De Kruif et al. |
| 2016/0031984 A1 | 2/2016 | Reyes et al. |
| 2016/0229920 A1 | 8/2016 | Ward et al. |
| 2016/0367699 A1 | 12/2016 | Jackson et al. |
| 2017/0037145 A1 | 2/2017 | Geuijen et al. |
| 2017/0166653 A1 | 6/2017 | Garner et al. |
| 2020/0247892 A1 | 8/2020 | Geuijen et al. |
| 2020/0291130 A1 | 9/2020 | Throsby et al. |
| 2021/0054096 A1 | 2/2021 | Maussang-Detaille et al. |

FOREIGN PATENT DOCUMENTS

| | | |
|---|---|---|
| EP | 0314161 A1 | 5/1989 |
| EP | 0481790 A2 | 4/1992 |
| EP | 0523949 A1 | 1/1993 |
| EP | 2604625 A1 | 6/2013 |
| EP | 3600411 A1 | 2/2020 |
| EP | 3600413 A1 | 2/2020 |
| JP | H11500915 A | 1/1999 |
| JP | 2008531557 A | 8/2008 |
| JP | 2011508604 A | 3/2011 |
| JP | 2012509259 A | 4/2012 |
| JP | 2013511288 A | 4/2013 |
| JP | 2014508782 A | 4/2014 |
| JP | 2014511383 A | 5/2014 |
| JP | 2017507944 A | 3/2017 |
| WO | WO-9627011 A1 | 9/1996 |
| WO | WO-9850431 A2 | 11/1998 |
| WO | WO-0063403 A2 | 10/2000 |
| WO | WO-03004704 A2 | 1/2003 |
| WO | WO-03107218 A1 | 12/2003 |
| WO | WO-2004009618 A2 | 1/2004 |
| WO | WO-2004061104 A2 | 7/2004 |
| WO | WO-2005000894 A2 | 1/2005 |
| WO | WO-2005118635 A2 | 12/2005 |
| WO | WO-2006028936 A2 | 3/2006 |
| WO | WO-2006044908 A2 | 4/2006 |
| WO | WO-2006091209 A2 | 8/2006 |
| WO | WO-2006106905 A1 | 10/2006 |
| WO | WO-2007110205 A2 | 10/2007 |
| WO | WO-2007147901 A1 | 12/2007 |
| WO | WO-2008027236 A2 | 3/2008 |
| WO | WO-2008100624 A2 | 8/2008 |
| WO | WO-2008119353 A1 | 10/2008 |
| WO | WO-2008140493 A2 | 11/2008 |
| WO | WO-2009051974 A1 | 4/2009 |
| WO | WO-2009080251 A1 | 7/2009 |
| WO | WO-2009080252 A1 | 7/2009 |
| WO | WO-2009080253 A1 | 7/2009 |
| WO | WO-2009089004 A1 | 7/2009 |
| WO | WO-2009098596 A2 | 8/2009 |
| WO | WO-2009157771 A2 | 12/2009 |
| WO | WO-2010022736 A2 | 3/2010 |
| WO | WO-2010059315 A1 | 5/2010 |
| WO | WO-2010084197 A1 | 7/2010 |
| WO | WO-2010108127 A1 | 9/2010 |
| WO | WO-2010129304 A2 | 11/2010 |
| WO | WO-2010151792 A1 | 12/2010 |
| WO | WO-2011022727 A2 | 2/2011 |
| WO | WO-2011028952 A1 | 3/2011 |
| WO | WO-2011028953 A1 | 3/2011 |
| WO | WO-2011143545 A1 | 11/2011 |
| WO | WO-2012023053 A2 | 2/2012 |
| WO | WO-2012058768 A1 | 5/2012 |
| WO | WO-2012116317 A2 | 8/2012 |
| WO | WO-2012125573 A2 | 9/2012 |
| WO | WO-2012125864 A2 | 9/2012 |
| WO | WO-2012131555 A2 | 10/2012 |
| WO | WO-2013048883 A2 | 4/2013 |
| WO | WO-2013084151 A2 | 6/2013 |
| WO | WO-2013134686 A1 | 9/2013 |
| WO | WO-2013149159 A1 | 10/2013 |
| WO | WO-2013157953 A1 | 10/2013 |
| WO | WO-2013157954 A1 | 10/2013 |
| WO | WO-2014051433 A1 | 4/2014 |
| WO | WO-2014060365 A1 | 4/2014 |
| WO | WO-2014081954 A1 | 5/2014 |
| WO | WO-2014159580 A1 | 10/2014 |
| WO | WO-2014165855 A1 | 10/2014 |
| WO | WO-2014182970 A1 | 11/2014 |
| WO | WO-2015130172 A1 | 9/2015 |
| WO | WO-2015130173 A1 | 9/2015 |
| WO | WO-2016077734 A2 | 5/2016 |
| WO | WO-2016090024 A2 | 6/2016 |
| WO | WO-2016201454 A1 | 12/2016 |
| WO | WO-2017069628 A2 | 4/2017 |
| WO | WO-2018182422 A1 | 10/2018 |

OTHER PUBLICATIONS

Cooke, S.L., et al., "High-resolution array CGH clarifies events occurring on 8p in carcinogenesis," BMC Cancer, 8(288):1-15, BioMed Central Ltd., United Kingdom (Oct. 2008).

Duruisseaux, M., et al., "NRG1 fusion in a French cohort of invasive mucinous lung adenocarcinoma," Cancer Medicine, 5(12):3579-3585, John Wiley & Sons Ltd., United States (Dec. 2016).

Falls, D.L., "Neuregulins: functions, form, and signaling strategies," Exp Cell Res, 284:14-30, Elsevier, Netherlands (Mar. 2003).

Fernandez-Cuesta, L., et al., "Molecular Pathways: Targeting NRG1 Fusions in Lung Cancer," Clinical Cancer Research, 21(9):1989-1994, American Association for Cancer Research, United States (May 2015).

Fernandez-Cuesta, L., et al., "CD74-NRG1 Fusions in Lung Adenocarcinoma," Cancer Discovery, 4(4):415-422, American Association for Cancer Research, United States (Apr. 2014).

Gaborit, N., et al., "Emerging anti-cancer antibodies and combination therapies targeting HER3/ERBB3," Human Vaccines and Immunotherapies, 12(3):576-592, Taylor & Francis, United Kingdom (Mar. 2015).

Geuijen, C., et al., "Abstract LB-261: Mechanism of action of MCLA-128, a humanized bispecific IgG1 antibody targeting the HER2: HER3 heterodimer," Cancer Research; 106th Annual Meeting of The American Association for Cancer Research (AAACR), 75(Suppl 15):LB-261, Philadelphia, United States (Aug. 2015).

Hayes, N.V.L., and Gullick, W.J., "The Neuregulin Family of Genes and their Multiple Splice Variants in Breast Cancer," J. Mammary Gland Biol Neoplasia, 13(205):214, Springer, United States (Jun. 2008).

International Search Report for International Application No. PCT/NL2018/050206, European Patent Office, Netherlands, mailed on Jun. 22, 20018, 4 pages.

Jung, Y., et al., "VAMP2-NRG1 Fusion Gene is a Novel Oncogenic Driver of Non-Small-Cell Lung Adenocarcinoma," J Thor Oncol 10(7): 1107-1111, International Association for the Study of Lung Cancer, United States (Jul. 2015).

Junttila, T.T., et al., "Ligand-Independent HER2/HER3/PI3K Complex is Disrupted by Trastuzumab and is Effectively Inhibited by the PI3K Inhibitor GDC-0941," Cancer Cell, 15(5):429-440, Elsevier, Netherlands (May 2009).

Junttila, T.T., et al., "Superior In vivi Efficacy of Afucosylated Trastuzumab in the Treatment of HER2-Amplified Breast Cancer,"

(56) References Cited

OTHER PUBLICATIONS

Cancer Research, 70(11):4481-4489, American Association for Cancer Research, United States (Jun. 2010).

Le Clorennec, C., et al., "Neuregulin 1 Allosterically Enhances the Antitumor Effects of the Noncompeting Anti-HER3 Antibody 9 F7-F11 by Increasing its Binding to HER3," Molecular Cancer Therapeutics, 16(7):1312-1323, American Association for Cancer Research, United States (Jul. 2017).

Lee-Hoeflich, S.T., et al., "A Central Role for HER3 in HER2-Amplified Breast Cancer: Implications for Targeted Therapy," Cancer Research, 68(14):5878-5887, American Association for Cancer Research, United States (Jul. 2008).

Malm, M., et al., "Targeting HER3 using mono- and bispecific antibodies or alternative scaffolds," MABS 8(7): 1195-1209, Taylor & Frances, United Kingdom (Oct. 2016).

Merchant, M.A., et al., "An efficient route to human bispecific IgG," Nature Biotechnology, 16: 677-681, Nature Publishing Group, United States (Jul. 1998).

De Nardis, C., et al., "A new approach for generation bispecific antibodies based on a common light chain format and the stable architecture of human immunoglobulin G1," Journal of Biological Chemistry, 292(35):14706-14717, The American Society for Biochemistry and Molecular Biology, Inc., United States (Sep. 2017).

Ocana, A., et al., "HER3 Overexpression and Survival in Solid Tumors: A Meta-Analysis," J Natl Cancer Inst, 105(4):266-273, Oxford University Press, United Kingdom (Feb. 2013).

Pole, J.C.M., et al., High-resolution analysis of chromosome rearrangements on 8p in breast, colon and pancreatic cancer reveals a complex pattern of loss, gain and translocation, Oncogene, 25:5693-5706, Nature Publishing Group, United Kingdom (Sep. 2006).

Sanchez-Valdivieso, E.A., et al., "γ-Heregulin has no biological significance in primary breast cancer," British Journal of Cancer, 86(8):1362-1366, Cancer Research UK, United Kingdom (Apr. 2002).

Schoeberl, B., et al., "An ErB3 Antibody, MM-121, is Active in Cancers with Ligand-Dependent Activation," Cancer Research, 70(6):2485-2494, American Association for Cancer Research, United States (Mar. 2010).

Sergina, N.V., et al., "Escape from HER-family tyrosine kinase inhibitor therapy by the kinase-inactive HER3," Nature, 445(7126):437-441, Springer, United Kingdom (Jan. 2007).

Weinstein, E.J., et al., "The oncogene heregulin induces apoptosos in breast wpithelial cells and tumors," Oncogene, 17:2107-2113, Stockton Press, United Kingdom (Oct. 1998).

Wilson, T.R., et al., "Widespread potential for growth-factor-driven resistance to anticancer kinase inhibitors," Nature, 487(7408):505-509, Springer, United Kingdom (Jul. 2012).

Wilson, T.R., et al., "Neuregulin-1-Mediated Autocrine Signaling Underlies Sensitivity to HER2 Kinase Inhibitors in a Subset of Human Cancer," Cancer Cells, 20(2):158-172, Elsevier, Inc., Netherlands (Aug. 2011).

Yarden, Y. et al., "The ERBB network: at last, cancer therapy meets systems biology," Nat Rev Cancer, 12:553-563, Macmillan Publishers, Limited, United Kingdom (Jul. 2012).

Zhang, H., et al., "ErbB receptors: from oncogenes to targeted cancer therapies," J Clin Invest, 117(8):2051-2058, The American Society for Clinical Investigations, United States (Aug. 2007).

125084 Erbitux Pharmacology Review Part 2—FDA, 31 pages.

Zhu, Z., et al., "Remodeling Domain Interfaces to Enhance Heterodimer Formation," Protein Science 6(4):781-788, Cold Spring Harbor Laboratory Press, United States (Apr. 1997).

Almagro, J.C. and Fransson, J., "Humanization of Antibodies," Frontiers in Bioscience 13:1619-1633, Frontiers in Bioscience Publications, United States (Jan. 2008).

Appella, E , et al., "Structure and Function of Epidermal Growth Factor-Like Regions in Proteins," FEBS Letters 231(1):1-4, John Wiley & Sons Ltd, United Kingdom (Apr. 1988).

Ardeshirpour, Y., et al., "In vivo assessment of HER2 receptor density in HER2-positive tumors by near-infrared imaging, using repeated injections of the fluorescent probe," Technology In Cancer Research & Treatment 13(5):427-434, SAGE, United States (Oct. 2014).

Arteaga, C.L., et al., "Treatment of Her2-positive Breast Cancer: Current Status and Future Perspectives," Nature Reviews Clinical Oncology 9(1):16-32, Nature Publishing Group, United Kingdom (Nov. 2011).

Schaefer, G., et al., "A Two-in-one Antibody Against Her3 and Egfr Has Superior Inhibitory Activity Compared With Monospecific Antibodies," Cancer Cell 20(4):472-486, Cell Press, United States (Oct. 2011).

Bargou, R., et al., "Tumor Regression in Cancer Patients by Very Low Doses of a T Cell-engaging Antibody," Science 321(5891):974-977, American Association for the Advancement of Science, United States (Aug. 2008).

Barthelemy, P.A., et al., "Comprehensive Analysis of the Factors Contributing to the Stability and Solubility of Autonomous Human Vh Domains," The Journal of Biological Chemistry 283:3639-3654, American Society for Biochemistry and Molecular Biology, United States (Feb. 2008).

Baselga, J., et al., "Pertuzumab Plus Trastuzumab Plus Docetaxel for Metastatic Breast Cancer," The New United Kingdom Journal of Medicine 366(2):109-119, Massachusetts Medical Society, United States (Jan. 2012).

Beiboer, S.H., et al., "Guided Selection of a Pan Carcinoma Specific Antibody Reveals Similar Binding Characteristics yet Structural Divergence between the Original Murine Antibody and its Human Equivalent," Journal of Molecular Biology 296(3):833-849, Elsevier, United Kingdom (Feb. 2000).

Birchmeier, C., et al., "Met, Metastasis, Motility and More," Nature Reviews Molecular Cell Biology 4(12):915-925, Nature Publishing Group, United Kingdom (Dec. 2003).

Blomquist, M.C., et al., "Vaccinia Virus 19-Kilodalton Protein: Relationship to Several Mammalian Proteins, Including Two Growth Factors," Proceedings of the National Academy of Sciences of the United States of America 81(23):7363-7367, National Academy of Sciences, United States (Dec. 1984).

Bostrom, J., et al., "Variants of the Antibody Herceptin that Interact with HER2 and VEGF at the Antigen Binding Site," Science 323(5921):1610-1614, American Association for the Advancement of Science, United States (Mar. 2009).

Boyer, C.M., et al., "Relative Cytotoxic Activity of Immunotoxins Reactive With Different Epitopes on the Extracellular Domain of the C-Erbb-2 (Her-2/Neu) Gene Product P185," International Journal of Cancer 82(4):525-531, John Wiley & Sons, Inc., United States (Aug. 1999).

Strelkauskas, A., et al., "Human Monoclonal Antibody: 2. Simultaneous Expression of lgG and lgM with Similar Binding Specificities by a Human Hybrid Clone," Hybridoma 6(5):479-488, Mary Ann Liebert, United States (Oct. 1987).

Zhao, X., et al., "Targeting C-type Lectin-like Molecule-1 for Antibody-mediated Immunotherapy in Acute Myeloid Leukemia," Haematologica 95(1):71-78, Ferrata Storti Foundation, Italy (Jan. 2010).

Selzer, T., et al., "Rational Design of Faster Associating and Tighter Binding Protein Complexes," Nature Structural & Molecular Biology 7(7):537-541, Nature Publishing Group, United States (Jul. 2000).

Carter, P., "Bispecific Human IgG by Design," Journal of Immunological Methods 248(1-2):7-15, Elsevier, Netherlands (Feb. 2001).

Carter, P., et al., "Toward the Production of Bispecific Antibody Fragments for Clinical Applications," Journal of Hematotherapy 4:463-470, Mary Ann Liebert, Inc., United States (Oct. 1995).

Castoldi, R., et al., "A Novel Bispecific EGFR/Met Antibody Blocks Tumor-promoting Phenotypic Effects Induced by Resistance to EGFR Inhibition and Has Potent Antitumor Activity," Oncogene 32(50):5593-5601, Nature Publishing Group, United Kingdom (Jul. 2013).

Chames, P., and Baty, D., "Bispecific Antibodies for Cancer Therapy: The Light at the End of the Tunnel?," MAbs 1(6):539-547, Taylor & Francis, United States (Nov.-Dec. 2009).

Chandra, A., "The Role of ERBB3 Inhibitors as Cancer Therapeutics," Boston University, 1-78 (May 2015).

(56) References Cited

OTHER PUBLICATIONS

Chen, C.T., et al., "MET activation mediates resistance to lapatinib inhibition of HER2-amplified gastric cancer cells," Molecular Cancer Therapeutics 11(3):650-669, American Association for Cancer Research, Inc., United States (Mar. 2012).

Chernomordik, V., et al., "Quantitative Analysis of HER2 Receptor Expression in Vivo By Near-Infrared Optical Imaging," Molecular Imaging 9(4):192-200, Sage Publications, United States (Aug. 2010).

Schlom, J., et al., "Therapeutic Advantage of High-affinity Anticarcinoma Radioimmunoconjugates," Cancer Research 52(5):1067-1072, American Association for Cancer Research, United States (Mar. 1992).

Clarke, M.F., et al., "Cancer stem cells—perspectives on current status and future directions: AACR Workshop on cancer stem cells," Cancer Research 66(19):9339-9344, American Association for Cancer Research, United States (Oct. 2006).

Cochran, J.R., et al., "Domain-level Antibody Epitope Mapping Through Yeast Surface Display of Epidermal Growth Factor Receptor Fragments," Journal of Immunology Methods 287(1-2):147-158, Elsevier, Netherland (Apr. 2004).

Conforti, F., et al., "Dissecting Breast Cancer Complexity: Specific Biological Features and Vulnerabilities of Triple Positive Breast Cancer Tumors," Clinic of Oncology 2(1288):1-3, Remedy Publications LLC, United States (May 2017).

Corada, M., et al., "Monoclonal Antibodies Directed To Different Regions of Vascular Endothelial Cadherin Extracellular Domain Affect Adhesion and Clustering of the Protein and Modulate Endothelial Permeability," Blood 97(6):1679-1684, American Society of Hematology, United States (Mar. 2001).

Corona S.P., et al., "CDK4/6 Inhibitors in HER2-positive Breast Cancer," Critical Reviews in Oncology/Hematology 118:208-214, Elsevier, Netherlands (Apr. 2017).

Curley, M.D., et al., "Seribantumab, An Anti-ERBB3 Antibody, Delays the Onset of Resistance and Restores Sensitivity to Letrozole in an Estrogen Receptor-Positive Breast Cancer Model," Molecular Cancer Therapeutics 14(11):2642-2652, American Association for Cancer Research, Inc., United States (Nov. 2015).

Davis, C.G., "The Many Faces of Epidermal Growth Factor Repeats," The New Biologist 2(5):410-419, W.B. Saunders Co., United States (May 1990).

Davis, J.H., et al., "SEEDbodies: Fusion Proteins Based on Strand-exchange Engineered Domain (SEED) CH3 Heterodimers in an Fc Analogue Platform for Asymmetric Binders or Immunofusions and Bispecific Antibodies," Protein Engineering, Design & Selection 23(4):195-202, Oxford University Press, United Kingdom (Apr. 2010).

De Genst, E., et al., "Antibody Repertoire Development in Camelids," Developmental and Comparative Immunology 30(1-2):187-198, Elsevier Science, United States (2006).

De Goeij, B.E., et al., "Efficient Payload Delivery by a Bispecific Antibody-Drug Conjugate Targeting HER2 and CD63," Molecular Cancer Therapeutics 5(11):2688-2697, American Association for Cancer Research, United States (Nov. 2016).

De Kruif, J., et al., "Selection and Application of Human Single Chain Fv Antibody Fragments from a Semi-Synthetic Phage Antibody Display Library with Designed CDR3 Regions," Journal of Molecular Biology 248(1):97-105, Elsevier, United Kingdom (Apr. 1995).

De Kruif, J., et al., "Generation of Stable Cell Clones Expressing Mixtures of Human Antibodies," Biotechnology and Bioengineering 106(5):741-750, Wiley, United States (Aug. 2010).

Zhang, B., et al., "Abstract 655: Combination of Mm-111, an Erbb2/erbb3 Bispecific Antibody, With Endocrine Therapies as an Effective Strategy for Treatment of Er+/her2+ Breast Cancer," Cancer Research 71(8):655-655, American Association for Cancer Research, United States (Jul. 2011).

Schmitz, K., and Ferguson K.M., "Interaction of Antibodies With ErbB Receptor Extracellular Regions," Experimental Cell Research 315(4):659-670, Academic Press, United States (Feb. 2009).

De Pascalis, R., et al., "Grafting of 'Abbreviated' Complementarity-determining Regions Containing Specificity-determining Residues Essential for Ligand Contact to Engineer a Less Immunogenic Humanized Monoclonal Antibody," Journal of Immunology 169(6):3076-3084, The American Association of Immunologists, United States (Sep. 2002).

De Vries, S.J., et al., "The HADDOCK Web Server for Data-driven Biomolecular Docking," Nature Protocols 5(5):883-897, Nature Publishing Group, United Kingdom (May 2010).

Dhanasekaran S.M., et al., "Transcriptome meta-analysis of lung cancer reveals recurrent aberrations in NRG1 and Hippo pathway genes," Nature Communications 5:5893, Springer Nature, Germany (Dec. 2014).

Seidel, C., et al., "Role of hepatocyte growth factor and its receptor c-met in multiple myeloma," Medical Oncology 15:145-153, Springer Nature, Switzerland AG (Sep. 1998).

Doolittle, R.F., et al., "Computer-Based Characterization of Epidermal Growth Factor Precursor," Nature 307(5951):558-560, Nature Publishing Group, United Kingdom (Feb. 1984).

Dreier, T., et al., "Extremely Potent, Rapid and Costimulation-Independent Cytotoxic T-Cell Response against Lymphoma Cells Catalyzed by a Single-Chain Bispecific Antibody," International Journal of Cancer 100(6):690-697, Wiley-Liss, United States (Aug. 2002).

Zhang, Y.W., et al., "MET kinase inhibitor SGX523 synergizes with epidermal growth factor receptor inhibitor erlotinib in a hepatocyte growth factor-dependent fashion to suppress carcinoma growth," Cancer Research 70(17):6880-6890, American Association for Cancer Research, United States (Sep. 2010).

Ewer, M.S., et al., "Cardiotoxicity of Anticancer Treatments: What the Cardiologist Needs to Know," Nature Reviews Cardiology 7(10):564-575, Nature Publishing Group, United Kingdom (Oct. 2010).

Ferguson, K.M., "Structure-based View of Epidermal Growth Factor Receptor Regulation," Annual Review of Biophysics 37:353-373, Annual Reviews, United States (2008).

Fong, J.T., et al., "Alternative signaling pathways as potential therapeutic targets for overcoming EGFR and c-Met inhibitor resistance in non-small cell lung cancer," PLoS One 8(11):e78398, Public Library of Science, United States (Nov. 2013).

Freeman D., et al., "Panitumumab and Cetuximab Epitope Mapping and in Vitro Activity," Journal of Clinical Oncology 26(15):14536-14536, American Society of Clinical Oncology, United States (May 2008).

Fu, W., et al., "Insights into HER2 signaling from step-by-step optimization of anti-HER2 antibodies," MAbs 6(4):978-990, Taylor & Francis, United Kingdom (Jul.-Aug. 2014).

Shames, D.S., et al., "High Heregulin Expression is Associated with Activated HER3 and May Define an Actionable Biomarker in Patients with Squamous Cell Carcinomas of the Head and Neck," PLoS One 8(2):e56765, Public Library of Science, United States (Feb. 2013).

Garrett, T.P., et al., "Crystal Structure of a Truncated Epidermal Growth Factor Receptor Extracellular Domain Bound to Transforming Growth Factor alpha," Cell 110(6):763-773, Cell Press, United States (Sep. 2002).

Wolff, A.C., et al., "Recommendations for Human Epidermal Growth Factor Receptor 2 Testing in Breast Cancer: American Society of Clinical Oncology/College of American Pathologists Clinical Practice Guideline Update," Journal of Clinical Oncology 31(31):3997-4013, Grune & Stratton, United States (Nov. 2013).

Woning, S.V.D., et al., "Quantification of ErbB3 Receptor Density on Human Breast Cancer Cells, Using a Stable Radio-Labeled Mutant of Nrglbeta," Biochemical and Biophysical Research Communications, 378(2):285-289, Elsevier, United States (Jan. 2009).

Xu, F., et al., "Antibody-Induced Growth Inhibition is Mediated Through Immunochemically and Functionally Distinct Epitopes on the Extracellular Domain of the c-erB-2 (HER-2/neu) Gene Product p185," International Journal of Cancer 53(3):401-408, Wiley-Liss, United States (Feb. 1993).

Yano, S. et al., "Hepatocyte Growth Factor Induces Gefitinib Resistance of Lung Adenocarcinoma With Epidermal Growth Fac-

(56) References Cited

OTHER PUBLICATIONS tor Receptor-activating Mutations," Cancer Research 68(22):9479-9487, American Association for Cancer Research, United States (Nov. 2008).

Yano, S., et al., "Molecular Mechanism of EGFR-TKI Resistance," Japanese Journal of Lung Cancer 49(6):939-943, The Japan Lung Cancer Society, Japan (Oct. 2009).

Yarden, Y. et al., "The EGFR family and its ligands in human cancer: signaling mechanisms and therapeutic opportunities," European Journal of Cancer 37(Supp4):S3-S8, Elsevier, Netherlands (Sep. 2001).

Yarden, Y., et al., "The ERBB Network: At Last, Cancer Therapy Meets Systems Biology," Nature Reviews Cancer 12(8):553-563, Nature Publishing Group, United Kingdom (Jul. 2012).

Yonesaka, K., et al., "Activation of ERBB2 Signaling Causes Resistance to the Egfr-Directed Therapeutic Antibody Cetuximab," Science Translational Medicine 3(99):99ra86, American Association for the Advancement of Science, United States (Sep. 2011).

Yu, H., et al., "Plasma Levels of Insulin-like Growth Factor-I and Lung Cancer Risk: A Case- control Analysis," Journal of the National Cancer Institute 91(2):151-156, Oxford University Press, United States (Jan. 1999).

Uberall, I., et al., "The status and role of ErbB receptors in human cancer," Experimental and Molecular Pathology 84:79-89, Elsevier, Netherlands (Apr. 2008).

U.S. Appl. No. 61/635,935, inventor Kruif; C.A.D, filed Apr. 20, 2012.

Vajdos, F.F., et al., "Comprehensive Functional Maps of the Antigen-binding Site of an Anti-Erbb2 Antibody Obtained with Shotgun Scanning Mutagenesis," Journal of Molecular Biology 320(2):415-428, Academic Press, United Kingdom (Jul. 2002).

Vecchione, L., et al., "EGFR-targeted therapy," Experimental Cell Research 317(19):2765-2771, Academic Press, United States (Nov. 2011).

Geuijen, C.A.W., et al., "Unbiased Combinatorial Screening Identifies a Bispecific IgG1 that Potently Inhibits HER3 Signaling via HER2-Guided Ligand Blockade," Cancer Cell 33(5):922-936, Elsevier, Netherlands (May 2018).

Sheridan, C., "Amgen Swallows Micromet to BiTE Into All Market," Nature Biotechnology 30(4):300-301, Nature America Publishing, United States (Apr. 2012).

Girlanda, S., et al., "MICA Expressed by Multiple Myeloma and Monoclonal Gammopathy of Undetermined Significance Plasma Cells Costimulates Pamidronate-activated Gammadelta Lymphocytes," Cancer Research, 65(16):7502-7508, American Association for Cancer Research, United States (Aug. 2005).

Greco, W.R., et al., "The Search for Synergy: a Critical Review From a Response Surface Perspective," Pharmacological Reviews 47(2):331-385, American Society for Pharmacology and Experimental Therapeutics, United States (Jun. 1995).

Gulli, L.F., et al., "Epidermal Growth Factor-induced Apoptosis in A431 Cells can be Reversed by Reducing the Tyrosine Kinase Activity," Cell Growth & Differentiation 7(2):173-178, The Association, United States (Feb. 1996).

Gunasekaran, K., et al., "Enhancing Antibody Fc Heterodimer Formation Through Electrostatic Steering Effects: Applications to Bispecific Molecules and Monovalent IgG," Journal of Biological Chemistry 285(25):19637-19646, American Society for Biochemistry and Molecular Biology, United States (Jun. 2010).

Gussow, D., and Seemann, G., "Humanization of Monoclonal Antibodies," Methods in Enzymology 203:99-121, Elsevier Science, United States (1991).

Shiraiwa H., et al., "Engineering a Bispecific Antibody With a Common Light Chain: Identification and Optimization of an Anti-cd3 Epsilon and Anti-GPC3 Bispecific Antibody, Ery974," Methods 154:10-20, Academic Press, United States (Feb. 2019).

Hammond, M.E.H., et al., "American Society of Clinical Oncology/ College of American Pathologists Guideline Recommendations for Immunohistochemical Testing of Estrogen and Progesterone Receptors in Breast Cancer," Journal of Clinical Oncology 28(16):2784-2795, American Society of Clinical Oncology, United States (Jun. 2010).

Siegfried, J.M., et al., "The clinical significance of hepatocyte growth factor for non-small cell lung cancer," The Annals of Thoracic Surgery 66(6):1915-1918, Elsevier, Netherlands (Dec. 1998).

Harms B., et al., "Understanding the Role of Cross-arm Binding Efficiency in the Activity of Monoclonal and Multispecific Therapeutic Antibodies", Methods 65(1):95-104, Elsevier, Netherlands (Jan. 2014).

Hathaway, H.J., et al., "Detection of breast cancer cells using targeted magnetic nanoparticles and ultra-sensitive magnetic field sensors," Breast Cancer Research 13(5):R108, BioMed Central, United Kingdom (Nov. 2011).

Hendsch, Z.S., et al., "Preferential Heterodimer Formation via Undercompensated Electrostatic Interactions," Journal of the American Chemical Society 123(6):1264-1265, American Chemical Society, United States (Feb. 2001).

Hommel, U., et al., "Human Epidermal Growth Factor. High Resolution Solution Structure and Comparison With Human Transforming Growth Factor Alpha," Journal of Molecular Biology 227(1):271-282, Elsevier, United Kingdom (Sep. 1992).

Sinha, N., et al., "Differences in Electrostatic Properties at Antibody-antigen Binding Sites: Implications for Specificity and Cross-reactivity," Biophysical Journal 83(6):2946-2968, Cambridge, United States (Dec. 2002).

Hu, T., and Li, C., "Convergence between Wnt-B-catenin and EGFR signaling in cancer," Molecular Cancer 236:1-7, BioMed Central, United States (Sep. 2010).

Huang W, et al., "Comparison of Central HER2 Testing With Quantitative Total HER2 Expression and HER2 Homodimer Measurements Using a Novel Proximity-Based Assay," American Journal of Clinical Pathology 134(2):303-311, Oxford University Press, United Kingdom (Aug. 2010).

Huhalov, A., et al., "MM-111, an ErbB2/ErbB3 Bispecific Antibody with Potent Activity in ErbB2-Overexpressing Cells, Positively Combines with Trastuzumab to Inhibit Growth of Breast Cancer Cells Driven by the ErbB2/ErbB3 Oncogenic Unit", Cancer Research 51:845-846, American Association for Cancer Research, United States (Apr. 2010).

Idusogie, E.E., et al., "Mapping of the Clq Binding Site on Rituxan, A Chimeric Antibody with a Human IgG1 Fc," The Journal of Immunology 164(8):4178-4184, American Association of Immunologists, United States (Apr. 2000).

International Search Report and Written Opinion for International Application No. PCT/NL2018/050329, European Patent Office, Netherlands, mailed on Sep. 17, 2018, 10 pages.

International Search Report and Written Opinion for International Application No. PCT/NL2018/050205, European Parent Office, Netherlands, mailed on Sep. 10, 2018, 23 pages.

International Preliminary Report on Patentability for International Application No. PCT/NL2016/050726, The International Bureau of WIPO, mailed on Apr. 24, 2018, 13 pages.

International Search Report and Written Opinion for International Application No. PCT/NL2018/050537, European Patent Office, Netherlands, mailed on Jan. 30, 2019, European Patent Office, Rijswijk, Netherlands, 19 pages.

International Search Report and Written Opinion for International Application No., PCT/NL2018/050204, European Patent Office, Netherlands, mailed on Jun. 25, 2018, 16 pages.

International search report and written opinion for International Application No. PCT/NL2016/050726, European Patent Office, Netherlands, mailed Jun. 2, 2017, 20 pages.

Jackson, C., et al., "Clinical Significance of HER-2 Splice Variants in Breast Cancer Progression and Drug Resistance," International Journal of Cell Biology 2013:973584, Hindawi, United Kingdom (Jul. 2013).

Zolot, R.S., et al., "Antibody-Drug Conjugates," Nature Reviews Drug Discovery 12(4):259-260, Nature Publishing Group, United Kingdom (Apr. 2013).

(56) References Cited

OTHER PUBLICATIONS

Sinha, N., et al., "Electrostatics in Protein Binding and Function," Current Protein and Peptide Science 3(6):601-614, Bentham Science Publishers, Netherlands (Dec. 2002).
Jelovac, D., et al., "HER2-Directed Therapy for Metastatic Breast Cancer," Oncology (Williston Park) 27(3):166-175, CMP Healthcare Media, United States (Mar. 2013).
Ji, H., et al., "Epidermal growth factor receptor variant III mutations in lung tumorigenesis and sensitivity to tyrosine kinase inhibitors," PNAS 103(20):7817-7822, United States National Academy of Sciences, United States (May 2006).
Jiang, B., et al., "A Novel Peptide Isolated from a Phage Display Peptide Library with Trastuzumab can Mimic Antigen Epitope of HER-2," The Journal of Biological Chemistry 280(6):4656-4662, The American Society for Biochemistry and Molecular Biology, United States (Feb. 2005).
Jin, H., et al., "Metmab, the One-Armed 5D5 Anti-C-Met Antibody, Inhibits Orthotopic Pancreatic Tumor Growth and Improves Survival," Cancer Research 68(11):4360-4368, American Association for Cancer Research, United States (Jun. 2008).
Jorissen, R.N., et al., "Epidermal Growth Factor Receptor: Mechanisms of Activation and Signaling," Experimental Cell Research 284(1):31-53, Academic Press, United States (Mar. 2003).
Kabat, E.A., et al., "Identical V Region Amino Acid Sequences and Segments of Sequences in Antibodies of Different Specificities. Relative Contributions of Vh and Vl Genes, Minigenes, and Complementarity-determining Regions to Binding of Antibody-combining Sites," Journal of Immunology 147(5):1709-1719, American Association of Immunologists, United States (Sep. 1991).
Kang J.C., et al., "Engineering Multivalent Antibodies to Target Heregulin-Induced HER3 Signaling in Breast Cancer Cells," MAbs 6(2):340-353, Taylor & Francis, United Kingdom (Apr. 2014).
Kim, G.P., et al. "Targeting Colorectal Cancer with Human Anti-EGFRMonoclonocal Antibodies: Focus on Panitumumab," Biologics 2(2):223-228, Dove Medical Press, New Zealand (Jun. 2008).
Soltoff, S.P., et al., "ErbB3 is involved in activation of phosphatidylinositol 3-kinase by epidermal growth factor," Molecular and Cellular Biology 14(6):3550-3558, American Society for Microbiology, United States (Jun. 1994).
Kim, K.H., et al., "Progress of Antibody-Based Inhibitors of the Hgf-Cmet Axis in Cancer Therapy," Experimental & Molecular Medicine 49(3):e307, Nature Publishing Group, United States (Mar. 2017).
Kipriyanov, S.M., et al., "Bispecific CD3 x CD19 Diabody for T Cell-Mediated Lysis of Malignant Human B Cells," International Journal of Cancer 77(5):763-772, Wiley-Liss, United States (Aug. 1998).
Klein, C., et al., "Progress in Overcoming the Chain Association Issue in Bispecific Heterodimeric IgG Antibodies," MAbs 4(6):653-663, Taylor & Francis, United States (Nov.-Dec. 2012).
Kodack D.P., et al., "Combined Targeting of HER2 and VEGFR2 for Effective Treatment of HER2-amplified Breast Cancer Brain Metastases," Proceedings of the National Academy of Sciences 109(45):E3119-E3127, United States National Academy of Sciences, United States (Nov. 2012).
Koide, A., et al., "The Fibronectin Type III Domain as a Scaffold for Novel Binding Proteins," Journal of Molecular Biology 284(4):1141-1151, Academic Press, United States (Dec. 1998).
Kol, A., et al., "HER3, Serious Partner in Crime: Therapeutic Approaches and Potential Biomarkers for Effect of HER3-targeting," Pharmacology & Therapeutics 143(1):1-11, Pergamon Press, United Kingdom (Jul. 2014).
Kontermann, R.E., "Dual Targeting Strategies with Bispecific Antibodies," MAbs 4(2):182-197, Taylor and Francis, United States (Mar.-Apr. 2012).
Sorkin, A., "Internalization of the Epidermal Growth Factor Receptor: Role in Signaling," Biochemical Society Transactions 29(Pt 4):480-484, Portland Press on the Behalf of the Biochemical Society, United Kingdom (Aug. 2001).
Kruif, D.J., et al., "Human Immunoglobulin Repertoires Against Tetanus Toxoid Contain a Large and Diverse Fraction of High-affinity Promiscuous V(H) Genes," Journal of Molecular Biology 387(3):548-558, Elsevier, United Kingdom (Apr. 2009).
Spiess, C., et al., "Alternative Molecular Formats and Therapeutic Applications for Bispecific Antibodies," Molecular Immunology 67(2 Pt A):95-106, Pergamon Press, United Kingdom (Oct. 2015).
Kubota, T., et al., "Engineered therapeutic antibodies with improved effector functions," Cancer Science 100(9):1566-1572, Wiley Publishing on behalf of the Japanese Cancer Association, United Kingdom (Sep. 2009).
Kulkarni-Kale, U., et al., "CEP: a Conformational Epitope Prediction Server," Nucleic Acids Research 33:W168-W171, Oxford University Press, United Kingdom (Jul. 2005).
Landgraf, R., et al., "HER2 Therapy. HER2 (ERBB2): Functional Diversity from Structurally Conserved Building Blocks," Breast Cancer Research 9(1):202, BioMed Central Ltd, United Kingdom (2007).
Lazrek, Y., et al., "Anti-HER3 Domain 1 and 3 Antibodies Reduce Tumor Growth by Hindering HER2/HER3 Dimerization and AKT-Induced MDM2. Xiap, and Fox1 Phosphorylation," Neoplasia 15(3):335-347, Neoplasia Press, United States (Mar. 2013).
Le Gall, F., et al., "Effect of Linker Sequences Between the Antibody Variable Domains on the Formation, Stability and Biological Activity of a Bispecific Tandem Diabody," Protein Engineering, Design & Selection 17(4):357-366, Oxford University Press, United Kingdom (Apr. 2004).
Ledon, N., et al., "Comparative Analysis of Binding Affinities to Epidermal Growth Factor Receptor of Monoclonal Antibodies Nimotuzumab and Cetuximab Using Different Experimental Animal Models," Placenta 32:531-534, Elsevier, Netherlands (Jul. 2011).
Lee, D., et al., "Development of antibody-based c-Met inhibitors for targeted cancer therapy," Immunotargets and Therapy 9(4):34-44, Dove Medical Press, New Zealand (Feb. 2015).
Lee, H.J., et al., "Gemini Vitamin D Analog Suppresses Erbb2-positive mammary tumor growth via inhibition of ErbB2/AKT/ERK Signaling," Journal of Steroid Biochemistry and Molecular Biology 121(1-2):408-412 Elsevier Science Ltd, United Kingdom (Jul. 2010).
Li, S., et al., "Structural basis for inhibition of the epidermal growth factor receptor by cetuximab," Cancer Cell 7(4):301-311, Elsevier, United States (Apr. 2005).
Lichtenberger, B.M., et al., "Epidermal Egfr Controls Cutaneous Host Defense and Prevents Inflammation," Science Translational Medicine 5(199):1-13, American Association for the Advancement of Science, United States (Aug. 2013).
Liesveld, J.L., et al., "Expression of IgG Fc Receptors in Myeloid Leukemic Cell Lines. Effect of Colony-stimulating Factors and Cytokines," Journal of Immunology 140(5):1527-1533, American Association of Immunologists, United States (Mar. 1988).
Liu, C and Lee, A., "ADCC Enhancement Technologies for Next Generation Therapeutic Antibody," Trends in Bio/Pharmaceutical Industry, 9 pages, 2009.
Liu, M.A., et al., "Heteroantibody Duplexes Target Cells for Lysis by Cytotoxic T Lymphocytes," Proceedings of the National Academy of Sciences of the United States of America 82(24):8648-8652, National Academy of Sciences, United States (Dec. 1985).
Loffler, A., et al., "A Recombinant Bispecific Single-chain Antibody, CD19 X CD3, Induces Rapid and High Lymphoma-directed Cytotoxicity by Unstimulated T Lymphocytes," Blood 95(6):2098-2103, American Society of Hematology, United States (Mar. 2000).
Logtenberg, T., "Hub for Organoids", Poster Presentation, www.innovationforhealth.nl/index.php/page/getFileUID/id/82364b177dfed9754d785aafffb21363/cr_usedb/25, 29 pages, Mar. 22, 2016.
Lotenberg, T., "Hub for organoids can we take it beyond the buzz" Retrieved from Internet: (https://www.innovationtorhealth.nl/index.php/page/getFileUIDIuid/82364b177dfed9754d785aafffb21363/crusedb/25).
Luo, H., et al., "Noninvasive Brain Cancer Imaging With a Bispecific Antibody Fragment, Generated via Click Chemistry," Proceedings

(56) References Cited

OTHER PUBLICATIONS of the National Academy of Sciences of the United States of America 112(41):12806-12811, National Academy of Sciences, United States (Oct. 2015).

Ma, P.C., et al., "C-Met: Structure, Functions and Potential for Therapeutic Inhibition," Cancer and Metastasis Reviews 22:309-325, Kluwer Academic, Netherlands (Dec. 2003).

Malm, M., et al., "Engineering of a Bispecific Affibody Molecule Towards HER2 and HER3 by Addition of an Albumin-Binding Domain Allows for Affinity Purification and in Vivo Half-Life Extension," Biotechnology Journal 9(9):1215-1222, Wiley-VCH Verlag, Germany (Sep. 2014).

Marshall, A.S., et al., "Identification and Characterization of a Novel Human Myeloid Inhibitory C-type Lectin-like Receptor (MICL) That is Predominantly Expressed on Granulocytes and Monocytes," The Journal of Biological Chemistry 279(15):14792-14802, American Society for Biochemistry and Molecular Biology, United States (Apr. 2004).

Maulik, G., et al., "Role of the hepatocyte growth factor receptor, c-Met, in oncogenesis and potential for therapeutic inhibition," Cytokine & Growth Factor Reviews 13(1):41-59, Elsevier Science, United Kingdom (Feb. 2002).

Maussang ., et al., "The Binding Mode of the Bispecific Anti-Her2xHer3 antibody MCLA-128 is Responsible for its Potent Inhibition of HRG-Driven Tumorigenesis," Research Poster Presentation Design, 2001, Apr. 1, 2017, Retrieved from the Internet: (URL: http://www.merus.nl/wordpress/wp-content/uploads/2017/04/MCLA- 128-poster-AACR2017-final-.pdf).

May, C., et al., "Advances in Bispecific Biotherapeutics for the Treatment of Cancer," Biochemical Pharmacology 84:1105-1112, Elsevier, Netherlands (Nov. 2012).

McDonagh, C.F., et al., "Antitumor Activity of a Novel Bispecific Antibody that Targets the ErbB2/ErbB3 Oncogenic Unit and Inhibits Heregulin-Induced Activation of ErbB3," Molecular Cancer Therapeutics 11(3):582-593, American Association for Cancer Research, United States (Mar. 2012).

Merlino, G.T., et al., "Amplification and Enhanced Expression of the Epidermal Growth Factor Receptor Gene in A431 Human Carcinoma Cells," Science 224(4647): 417-419, American Association for the Advancement of Science, United States (Apr. 1984).

Merten, H., et al., "Antibody-drug Conjugates for Tumor Targeting-novel Conjugation Chemistries and the Promise of Non-IgG Binding Proteins," Bioconjugate Chemistry 26(11):2176-2185, American Chemical Society, United States (Nov. 2015).

Merus, www.merus.nl, press release, 2 pages, dated Jan. 7, 2013.

Merus, www.merus.nl, press release, 3 pages, dated Jun. 17, 2013.

Momeny, M., et al., "Heregulin-HER3-HER2 signaling promotes matrix metalloproteinase-dependent blood-brain-barrier transendothelial migration of human breast cancer cell lines," Oncotarget 6(6):3932-3946, Impact Journals LLC, United States (Feb. 2015).

Moores, S.L., et al., "A Novel Bispecific Antibody Targeting EGFR and cMet is Effective against EGFR Inhibitor-Resistant Lung Tumors," Cancer Research 76(13):3942-3953, American Association for Cancer Research, United States (May 2016).

Morgillo, F., et al., "Mechanisms of resistance to EGFR targeted drugs: lung cancer," ESMO Open 2016 1:e000060, 13 pages, Biomedical Journal, United States (May 2016).

Stancovski, I., et al., "Mechanistic aspects of the opposing effects of monoclonal antibodies to the ERBB2 receptor on tumor growth," Proceedings of the National Academy of Sciences USA 88(19):8691-8695, National Academy of Sciences, United States (Oct. 1991).

Morrison, M.M., et al., "ErbB3 Downregulation Enhances Luminal Breast Tumor Response to Antiestrogens," The Journal of Clinical Investigation 123(10):4329-4343, American Society for Clinical Investigation, United States (Oct. 2013).

Mosmi, S., et al., "Role of MetMAb (OA-5D5) in c-MET Active Lung Malignancies," Expert Opinion on Biological Therapy 11(12):1655-1662, Taylor & Francis, United Kingdom (Dec. 2011).

Mullard, A., et al., "Maturing Antibody-drug Conjugate Pipeline Hits 30," Nature Reviews Drug Discovery 12(5):329-332, Nature Publishing Group, United Kingdom (May 2013).

Musolino, A., et al., "Immunoglobulin G Fragment C Receptor Polymorphisms and Clinical Efficacy of Trastuzumab-based Therapy in Patients With Her-2/neu-positive Metastatic Breast Cancer," Journal of Clinical Oncology 26(11): 1789-1796, American Society of Clinical Oncology, United States (Apr. 2008).

Nakade, J., et al., "Triple Inhibition of EGFR, MET, and VEGF Suppresses Regrowth of HGF-Triggered, Erlotinib-Resistant Lung Cancer Harboring an EGFR Mutation," Journal of Thoracic Oncology 9(6):775-783, Elsevier, United States (Jun. 2014).

Nieba, L., et al., "Disrupting the Hydrophobic Patches at the Antibody Variable/constant Domain Interface: Improved in Vivo Folding and Physical Characterization of an Engineered Scfv Fragment," Protein Engineering 10(4):435-444, Oxford University Press, United Kingdom (Apr. 1997).

Nissim, A., et al., "Antibody Fragments From a 'single Pot' Phage Display Library as Immunochemical Reagents," The EMBO Journal 13(3):692-698, EMBO Press, Germany (Feb. 1994).

Park, N.J., et al., "Measurement of Cetuximab and Panitumumab-Unbound Serum EGFR Extracellular Domain Using an Assay Based on Slow Off-Rate Modified Aptamer (SOMAmer) Reagents," PloS One 8(8):e71703, Public Library of Science, United States (Aug. 2013).

Surati, M., et al., "Role of MetMab (OA-5D5) in c-MET active lung malignancies," Expert Opinion on Biological Therapy 11(12):1655-1662, Taylor & Francis, United Kingdom (Dec. 2011).

Olayioye, M.A., et al., "The ErbB Signaling Network: Receptor Heterodimerization in Development and Cancer," EMBO Journal 19(13):3159-3167, EMBO Press, Germany (Jul. 2000).

Omenn, G.S., et al., "A New Class of Protein Cancer Biomarker Candidates: Differentially-Expressed Splice Variants of ERBB2 (HER2/neu) and ERBB1 (EGFR) in Breast Cancer Cell Lines," Journal of Proteomics 107:103-112, Elsevier, Netherlands (Jul. 2014).

Tanner, M., et al., "Characterization of a Novel Cell Line Established From a Patient With Herceptin-resistant Breast Cancer," Molecular Cancer Therapeutics 3(12):1585-1592, American Association for Cancer Research, United States (Dec. 2004).

Thery, J.C., et al., "Resistance to Human Epidermal Growth Factor Receptor Type 2-targeted Therapies," European Journal of Cancer 50(5):892-901, Elsevier, Netherlands (Mar. 2014).

Organ, S.L., et al., "An Overview of the C-Met Signaling Pathway," Therapeutic Advances in Medical Oncology 3(1 Suppl):S7-S19, Sage, United Kingdom (Nov. 2011).

Pan, D.S., et al., "Binding Characteristic of Fully Human Anti-EGFR Monoclonal Antibody to EGFR in Skin Tissues of Different Species of Animals," Chinese Journal of New Drugs Co. Ltd, 21(1):26-30, China (Jan. 2012).

Panke, C., et al., "Quantification of Cell Surface Proteins with Bispecific Antibodies," Protein Engineering Design and Selection 26(10):645-654, Oxford University Press, United Kingdom (Aug. 2013).

Papadea, C., and Check, I.J., "Human Immunoglobulin G and Immunoglobulin G Subclasses: Biochemical, Genetic, and Clinical Aspects," Critical Reviews in Clinical Laboratory Sciences 27(1):27-58, Informa Healthcare, United Kingdom (1989).

Pastore, S., et al., "Erk1/2 Regulates Epidermal Chemokine Expression and Skin Inflammation," Journal of Immunology 174:5047-5056 (Apr. 2005).

Patel, D.K., "Clinical Use of Anti-epidermal Growth Factor Receptor Monoclonal Antibodies in Metastatic Colorectal Cancer," Pharmacotherapy 28(11):31S-41S, Wiley, United States (Nov. 2008).

Paul, I., et al., "Current Understanding on EGFR and Wnt/Beta-Catenin Signaling in Glioma and Their Possible Crosstalk," Genes & Cancer 4(11-12):427-446, Sage, United States (Nov. 2013).

Pedersen, M.W., et al., "Targeting Three Distinct HER2 Domains with a Recombinant Antibody Mixture Overcomes Trastuzumab Resistance," Molecular Cancer Therapeutics 14(3):669-680, American Association for Cancer Research, United States (Jan. 2015).

Wadhwa, D., et al., "Trastuzumab Mediated Cardiotoxicity in the Setting of Adjuvant Chemotherapy for Breast Cancer: a Retrospec-

(56) References Cited

OTHER PUBLICATIONS tive Study," Breast Cancer Research and Treatment 117(2):357-364, Kluwer Academic, Netherlands (Sep. 2009).

Wehrman, T.S., et al., "A System for Quantifying Dynamic Protein Interactions Defines a Role for Herceptin in Modulating ErbB2 Interactions," Proceedings of the National Academy of Sciences of the United States of America 103(50):19063-19068, National Academy of Sciences, United States (Dec. 2006).

Wick, M.J., et al., "Establishment and Characterization of a HER2-positive, TDM1-Resistant PDX Breast Model," Abstract C74 at AACR-NCI-EORTC International Conference: Molecular Targets and Cancer Therapeutics, Nov. 5-9, 2015, Boston and Drug Resistance and Modifiers, vol. 14, No. 12, Supplement 2, 4 pages.

Troise, F., et al., "A novel ErbB2 epitope targeted by human antitumor immunoagents," FEBS Journal 278:1156-1166, John Wiley & Sons, United States (Apr. 2011).

Prigent, S., et al., "Identification of C-erbB-3 Binding Sites for Phosphatidylinositol 3'-kinase and SHC Using an EGF Receptor/c-erbB-3 Chimera," The EMBO Journal 13(12):2831-2841, National Center for Biotechnology Information, United States (Jun. 1994).

Raffen, R., et al., "Reengineering Immunoglobulin Domain Interactions by Introduction of Charged Residues," Protein Engineering 11(4):303-309, Oxford University Press, United Kingdom (Apr. 1998).

Regina, A., et al., "ANG4043, a Novel Brain-Penetrant peptide-mAb Conjugate, is Efficacious Against HER2-positive Intracranial Tumors in Mice," Molecular Cancer Therapeutics 14(1):129-140, American Association for Cancer Research, Inc., United States (Jan. 2015).

Richards, D.A., et al., "A Phase 1 Study of Mm-111, a Bispecific HER2/HER3 Antibody Fusion Protein, Combined with Multiple Treatment Regimens in Patients with Advanced HER2-Positive Solid Tumors," Journal of Clinical Oncology 32(15):651, American Society of Clinical Oncology, United States (May 2014).

Ridgway, J.B., et al., "'Knobs-Into-Holes' Engineering of Antibody CH3 Domains for Heavy Chain Heterodimerization," Protein Engineering 9(7):617-621, Oxford University Press, United Kingdom (Jul. 1996).

Riemer, A.B., et al., "Matching of Trastuzumab (Herceptin) Epitope Mimics Onto the Surface of Her-2/neu-a New Method of Epitope Definition," Molecular Immunology 42(9):1121-1124, Pergamon Press, United Kingdom (May 2005).

Robertson, S.C., et al., "RTK mutations and human syndromes: when good receptors turn bad," Trends in Genetics 16(6):368, Elsevier Science Publishers B.V, United Kingdom (Jun. 2000).

Robinson, M.K., et al., "Targeting ErbB2 and ErbB3 with a bispecific single-chain FV Enhances targeting selectivity and induces a therapeutic effect in Vitro", British Journal of CA 99(9):1415-1425, Nature Publishing Group, United Kingdom (Oct. 2008).

Roskoski, R., "The ErbB/HER Family of Protein-Tyrosine Kinases and Cancer," Pharmacological Research 79:34-74, Elsevier, Netherlands (Jan. 2014).

Sandercock, A.M., et al., "Identification of anti-tumour biologics using primary tumour models, 3-D phenotypic screening and image-based multi-parametric profiling," Mol Cancer 14:147, BioMed Central Ltd, United Kingdom (Jul. 2015).

Wang, X. Z., et al., "γ-heregulin is the product of a chromosomal translocation fusing the DOC4 and HGL/NRG1 genes in the MDA-MB-175 breast cancer cell line," Oncogene 18(41):5718-5721, Nature Publishing Group, United Kingdom (Oct. 1999).

Geuijen, C., et al., "Preclinical Activity of MCLA-128, an ADCC Enhanced Bispecific IgG1 Antibody Targeting the HER2:HER3 Heterodimer," Journal of Clinical Oncology 32(15):560-560, Netherlands (May 2014).

Howarth, K.D., et al., "NRG1 fusions in breast cancer," Breast Cancer Res 23(1):3, BioMed Central, United Kingdom (Jan. 2021).

Shin, D.H., et al., "Oncogenic function and clinical implications of SLC3A2-NRG1 fusion in invasive mucinous adenocarcinoma of the lung," Oncotarget 7(43):69450-69465, Impact Journals, United States (Oct. 2016).

Schmidt, M., et al., "High-resolution insertion-site analysis by linear amplification-mediated PCR (LAM-PCR)," Nat Methods 4(12):1051-1057, Springer Nature, Germany (Dec. 2007).

U.S. Appl. No. 18/449,460, Throsby, M., et al., filed Aug. 14, 2023 (Not Published).

```
                                                            CDR3
                70        80        90       100       110       120
MF3178  RVTMTRDTSISTAYMELSRLRSDDTAVYYCAR DHGSRHFWSYWGFDY WGQGTLVTVSS
MF6055  ....E..T........................ ............... ...........
MF6056  ..S.E..T.......Q................ ............... ...........
MF6057  ....E..T.......Q...............T ............... ...........
MF6058  ..S.E..T.......Q................ ............... ...........
MF6059  ....E..T.......Q...............T ............... ...........
MF6060  ....E..T........................ ............... ...........
MF6061  .......T.......................T ............... ...........
MF6062  .......T........................ ............... ...........
MF6063  .......T........................ ............... ...........
MF6064  .......T........................ ............... ...........
MF6065  .......T.....V.........E........ ............... ...........
MF6066  .......T.............S.E........ ............... ...........
MF6067  .......T.....V.........E........ ............... ...........
MF6068  .......T.............S.E........ ............... ...........
MF6069  .......T........................ ............... ...........
MF6070  .......T.....V.........E........ ............... ...........
MF6071  .......T.............S.E........ ............... ...........
MF6072  .......T.....V.........E........ ............... ...........
MF6073  .......T.............S.E........ ............... ...........
MF6074  .......T........................ ............... ...........
```

ERBB-2 AND ERBB-3 BINDING BISPECIFIC ANTIBODIES FOR USE IN THE TREATMENT OF CELLS THAT HAVE AN NRG1 FUSION GENE

CROSS-REFERENCE TO RELATED APPLICATIONS

This application is a continuation of U.S. application Ser. No. 18/449,460, date Aug. 14, 2023, which is a divisional of U.S. application Ser. No. 16/499,185, 371(c) date Sep. 27, 2019, now U.S. Pat. No. 11,780,925, which is a 35 U.S.C. § 371 National Phase Application of PCT/NL2018/050206, filed Apr. 3, 2018; which claims priority to EP Application No. 17164292.9, filed Mar. 31, 2017.

REFERENCE TO A SEQUENCE LISTING SUBMITTED ELECTRONICALLY VIA EFS-WEB

This application includes a Sequence Listing submitted electronically via EFS-Web (Name: "4096_0260003_Seqlisting_ST26.xml"; Size; 207,139 Bytes; and Date of Creation: Jan. 16, 2023), which is hereby incorporated by reference in its entirety.

The invention relates to the field of antibodies. In particular it relates to the field of therapeutic (human) antibodies for the treatment of a ErbB-2/ErbB-3 positive cell. More in particular it relates to treating tumors comprising an NRG1 fusion gene comprising at least a portion of the NRG1-gene fused to a sequence from a different chromosomal location.

Neuregulin-1 (NRG1) has been proposed as a candidate oncogene and as a candidate tumor suppressor gene. It is likely to be involved in epithelial cancers, because it encodes ligands that can bind to the ErbB-family of receptors. To date, there are over 16 soluble and transmembrane proteins derived from the NRG1 gene. Proteolytic processing of the extra cellular domain of the transmembrane NRG1 isoforms release soluble factors. HRG1-β1 is one of the proteins encoded by the gene. It contains an Ig domain and an EGF-like domain that is necessary for direct binding to receptor tyrosine kinases ErbB-3 and ErbB-4. The NRG1 gene and the isoforms are known under a number of different aliases such as: Neuregulin 1; Pro-NRG1; HRGA; SMDF; HGL; GGF; NDF; NRG1 Intronic Transcript 2 (Non-Protein Coding); Heregulin, Alpha (45 kD, ERBB2 P185-Activator); Acetylcholine Receptor-Inducing Activity; Pro-Neuregulin-1, Membrane-Bound Isoform; Sensory And Motor Neuron Derived Factor; Neu Differentiation Factor; Glial Growth Factor 2; NRG1-IT2; MSTP131; MST131; ARIA; GGF2; HRG1; and HRG. External Ids for NRG1 Gene are HGNC: 7997; Entrez Gene: 3084; Ensembl: ENSG00000157168; OMIM: 142445 and UniProtKB: Q02297.

Isoforms of NRG1 are made by alternative splicing, and include forms that are transmembrane, externally membrane bound, shed, secreted or intracellular (Falls, 2003; Hayes and Gullick, 2008). They bind to ErbB-3 or ErbB-4, which probably signal as heterodimers with ErbB-2 (HER2). Although the NRG1-encoded proteins are usually thought of as mitogens, they can also be powerfully proapoptotic: in particular, expressing NRG1 in cells can cause apoptosis of the expressing cell (Weinstein et al., 1998).

The NRG1 gene has been identified as a potential cancer-critical gene in two, apparently contradictory, contexts. First, it is the prime candidate for the major tumor suppressor gene thought to be on chromosome 8p, the short arm of chromosome 8. Loss of chromosome 8p is one of the most frequent genomic events in epithelial cancers, including breast, colon, bladder and prostate. This has been shown successively by loss of heterozygosity, comparative genomic hybridization (CGH) and array-CGH studies (for references, see Birnbaum et al., 2003; Pole et al., 2006). The classical interpretation of this loss of chromosome 8p would be that there is a tumor suppressor gene there. Chromosome 8p losses in carcinoma cell lines were mapped using fluorescence-in situ hybridization and array-comparative genomic hybridization (array-CGH). It was found that most breaks were proximal to, or actually within NRG1, making NRG1 and genes immediately telomeric to NRG1 the prime candidates for such a tumor suppressor (Pole et al., 2006; Cooke et al., 2008). Second, NRG1 could be an oncogene because it seems to be the target of chromosome translocations in breast cancer (for review see Chua et al 2009).

In the present invention it was found that tumors with chromosome 8p modifications exhibit growth inhibition in response to exposure to a bispecific antibody that comprises a first antigen-binding site that can bind an extracellular part of ErbB-2 and a second antigen-binding site that can bind an extracellular part of ErbB-3.

SUMMARY OF THE INVENTION

In one aspect, a method is provided for the treatment of an individual that has an ErbB-2 and ErbB-3 positive cell, the method comprising administering a bispecific antibody that comprises a first antigen-binding site that can bind an extracellular part of ErbB-2 and a second antigen-binding site that can bind an extracellular part of ErbB-3 to the individual in need thereof, the method characterized in that cell that comprises an NRG1 fusion gene comprising at least a portion of the NRG1-gene fused to a sequence from a different chromosomal location. Typically, the cell comprises an NRG1 fusion gene comprising at least the 3' end of the NRG1-gene fused to a 5' sequence from a different chromosomal location.

The said cell may be a cancer cell. The said cancer cell may be a cancer cell associated with an NRG1-fusion gene, such as a cancer cell driven by an NRG1-fusion.

In another aspect, a method is provided for the treatment of an individual that has an ErbB-2 and ErbB-3 positive tumor or is at risk of having said tumor, the method comprising administering a bispecific antibody that comprises a first antigen-binding site that can bind an extracellular part of ErbB-2 and a second antigen-binding site that can bind an extracellular part of ErbB-3 to the individual in need thereof, the method characterized in that cells of the tumor comprises an NRG1 fusion gene comprising a portion of the NRG1 fusion, such as the 3' end of the NRG1-gene, fused to a sequence, such as a 5' sequence, from a different chromosomal location.

An individual at risk of having an ErbB-2 and ErbB-3 positive tumor may be an individual that is in remission.

Preferably, the NRG1-fusion gene expresses a protein that comprises an NRG1 EGF-like domain. Preferably, the NRG-fusion is a fusion of NRG1 and a gene on human chromosome 8. Preferably, the gene on human chromosome 8 encodes an excreted protein or a cellular membrane associated protein. Preferably, the NRG1 fusion gene is a fusion of the 3' end of the NRG1-gene with the 5' sequence of one of the genes selected from the group consisting of CD74; DOC4; TNFRSF10B; CLU; VAMP2; SLC3A2; RBPMS;

WRN; SDC4; KIF13B; SLECA2; PDE7A; ATP1B1; CDK1; BMPR1B; MCPH1 and RAB2IL1.

Preferably, the cell is an epithelial cell. Preferably, the cell is a breast cancer cell, an ovarian cancer cell, a lung cancer cell, such as non-small cell lung cancer or a metastasis thereof.

Preferably, the tumor is of an epithelial origin. Preferably, the tumor is a breast cancer, ovarian cancer, lung cancer, or a metastasis thereof.

The cell may be a cancer cell, for example an ovarian cancer comprising, for example, the CLU-NRG1 fusion or the RAB2IL1-NRG1

The cell may be a cancer cell, for example a breast cancer cell comprising, for example, the DOC4-NRG1 fusion The cell may be a cancer cell, for example a NSCLC (lung) cancer, such as the subtype termed invasive mucinous adenocarcinoma, comprising, for example, VAMP2-NRG1, RBPMS-NRG1, WRN-NRG1, SDC4-NRG1, SLEC3A2-NRG1, KIF13B-NRG1 or CD74-NRG1.

Preferably, the individual has undergone a therapy that targeted towards EGFR inhibition, preferably with an EGFR binding antibody, which is preferably cetuximab.

Preferably, the method further comprises determining the ErbB-1 cell-surface receptor density; ErbB-2 cell-surface receptor density; ErbB-3 cell-surface receptor density; ErbB-4 cell-surface receptor density or a combination thereof on the cells of the tumor. Preferably, the cell or tumor has less than 400,000 ErbB-1 cell-surface receptors per cell, preferably less than 200.000 ErbB-1 cell-surface receptors per cell.

Preferably, the method further comprises administering to the individual an ErbB-1 inhibitor, preferably cetuximab.

Preferably in the methods disclosed herein, the ErbB-2/ErbB-3 positive cell or tumor has less than 50,000 ErbB-3 cell-surface receptors per cell.

Preferably in the methods disclosed herein, the cell or cells of said tumor have a heregulin expression level that is greater than the heregulin expression level of MCF7 cells.

As is clear to a skilled person the bispecific antibodies disclosed herein are also for the use in the preparation of a medicament and for the use in therapy, as disclosed herein.

In particular, a bispecific antibody that comprises a first antigen-binding site that can bind an extracellular part of ErbB-2 and a second antigen-binding site that can bind an extracellular part of ErbB-3 for use in the treatment of an individual that has an ErbB-2 and ErbB-3 positive cell, which cell comprises an NRG1 fusion gene comprising at least the 3' end of the NRG1-gene fused to a 5' sequence from a different chromosomal location.

The said cell may be a cancer cell. The said cancer cell may be a cancer cell associated with an NRG1-fusion, such as a cancer cell driven by an NRG1-fusion.

Also, the bispecific antibodies are for use in the treatment of an ErbB-2/ErbB-3 positive tumor, wherein the cells of the tumor comprise an NRG1 fusion gene comprising the 3' end of the NRG1-gene fused to a 5' sequence from a different chromosomal location.

Preferably in the methods and uses disclosed herein, said first antigen-binding site binds domain I of ErbB-2 and said second antigen-binding site binds domain III of ErbB-3, preferably wherein the affinity of the first antigen-binding site for ErbB-2 is lower than the affinity of the second antigen-binding site for ErbB-3. Preferably wherein said bispecific antibody comprises i) at least the CDR1, CDR2 and CDR3 sequences of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 or wherein said antibody comprises CDR sequences that differ in at most 3 amino acids, preferably in at most 2 amino acids, preferably in at most 1 amino acid from the CDR1, CDR2 and CDR3 sequences of MF2926, MF2930, MF1849; MF2973, MF3004, MF3958, MF2971, MF3025, MF2916, MF3991, MF3031, MF2889, MF2913, MF1847, MF3001, MF3003 or MF1898; and/or ii) at least the CDR1, CDR2 and CDR3 sequences of an ErbB-3 specific heavy chain variable region selected from the group consisting of MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 and MF6074, or wherein said antibody comprises CDR sequences that differ in at most 3 amino acids, preferably in at most 2 amino acids, preferably in at most 1 amino acid from the CDR1, CDR2 and CDR3 sequences of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 or MF6074. Preferably, the antibody comprises i) an ErbB-2 specific heavy chain variable region sequence selected from the group consisting of the heavy chain variable region sequences of MF2926, MF2930, MF1849; MF2973, MF3004, MF3958, MF2971, MF3025, MF2916, MF3991, MF3031, MF2889, MF2913, MF1847, MF3001, MF3003 and MF1898, or wherein said antibody comprises a heavy chain variable region sequence that differs in at most 15 amino acids from the heavy chain variable region sequences of MF2926, MF2930, MF1849; MF2973, MF3004, MF3958, MF2971, MF3025, MF2916, MF3991, MF3031, MF2889, MF2913, MF1847, MF3001, MF3003 or MF1898; and/or ii) an ErbB-3 specific heavy chain variable region sequence selected from the group consisting of the heavy chain variable region sequences of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 and MF6074, or wherein said antibody comprises a heavy chain variable region sequence that differs in at most 15 amino acids from the heavy chain variable region sequences of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 or MF6074.

Preferably, the antibody comprises at least the CDR1, CDR2 and CDR3 sequences of the ErbB-2 specific heavy chain variable region MF3958 and the antibody comprises at least the CDR1, CDR2 and CDR3 sequences of the ErbB-3 specific heavy chain variable region MF3178. Preferably, the bispecific antibody comprises the "heavy chain for erbB-2 binding" as depicted in the Sequence listing part 1D and the "heavy chain for erbB-3 binding" as depicted in the Sequence listing part 1D.

Preferably, the first antigen binding site and said second antigen binding site comprise a light chain variable region comprising the IgVKl-39 gene segment, most preferably the rearranged germline human kappa light chain IgVKl-39*01/ IGJKl*01 or IgVκ1-39*01/IGJκ5*01. Preferably, the light chain variable region comprises a CDR1 having the sequence (RASQSISSYLN; SEQ ID NO: 75), a CDR2 having the sequence (AASSLQS; SEQ ID NO: 76), and a CDR3 having the sequence (QQSYSTPPT; SEQ ID NO: 77).

DETAILED DESCRIPTION OF THE INVENTION

An NRG1 fusion gene comprises at least a portion of the NRG1-gene fused to a sequence from a different chromosomal location. "At least a portion" indicates that the entire NRG-1 gene may be present in a fusion or a portion thereof. The fusion preferably has at least the coding sequence of exons 6, 7 and 8. Another way to define the NRG1 part in the NRG1-fusion gene is that it comprises the EGF-like domain of NRG1. The at least a portion of the NRG1 gene may be fused to a sequence from a different chromosomal location such that the said sequence is located 5' or 3' to the at least a portion of the NRG1 gene.

Preferably, the 3' end of the NRG1-gene may be fused to a 5' sequence from a different chromosomal location. The NRG1-gene codes for the various isoforms of NRG1. Various isoforms and their expected function are described in Adelaide et al (2003). GGF and GGF2 isoforms contain a kringle-like sequence plus Ig and EGF-like domains; and the SMDF isoform shares only the EGF-like domain with other isoforms. The EGF-like domain is encoded by the 3' end of the gene. The EGF-like domain is present in all NRG1 fusion genes of the present invention. Fusions have been found wherein the 5' from different chromosomal location comprises an excretion signal and/or or a transmembrane domain of a cellular membrane protein with at least one extracellular domain. An example is the CD74-NRG1 fusion. The 5' sequence from different chromosomal location may also insert a sequence that activates transcription of NRG1, examples are promoters or enhancers. The 5' sequence is typically a sequence from a gene different than NRG1. The sequence can comprise a coding region, an expression regulatory sequence such as a promoter or an enhancer, or a combination thereof. The NRG-fusion comprises a 5' sequence from a different location can be from a different chromosome or from another part of chromosome 8. In a preferred embodiment the 5'sequence is from a gene on human chromosome 8.

The NRG1-gene, for example the 3' end of the NRG-1 gene, in the fusion preferably has at least the coding sequence of exons 6, 7 and 8. Another way to define the NRG1 part in the NRG1-fusion gene is that it comprises the EGF-like domain of NRG1. This domain is encoded by the 3' end of the NRG1 gene (exons 6-8) and is necessary for binding to ErbB-3. NRG1-fusions retain an in frame coding region for this EGF-like domain at the 3'end of the fusion. An EGF-like domain is a sequence of typically about thirty to forty amino-acid residues long of which the prototype is found in the sequence of epidermal growth factor (EGF) [PMID: 2288911, PMID: 6334307, PMID: 1522591, PMID: 6607417, PMID: 3282918, PMID: 11498013]. It is known to be present, in a more or less conserved form, in a large number of other, mostly animal proteins. A common feature of EGF-like domains is that they are found in the extracellular domain of membrane-bound proteins or in proteins known to be secreted (exception: prostaglandin G/H synthase). The EGF domain typically includes six cysteine residues which have been shown (in EGF) to be involved in disulphide bonds. The main structure is a two-stranded beta-sheet followed by a loop to a C-terminal short two-stranded sheet. Subdomains between the conserved cysteines vary in length.

The NRG1 fusion gene is preferably a fusion of the 3' end of the NRG1-gene with the 5' sequence of one of the genes selected from the group consisting of CD74; DOC4; TNFRSF10B; CLU; VAMP2; SLC3A2; RBPMS; WRN; SDC4; KIF13B; SLECA2; PDE7A; ATP1B1; CDK1; BMPR1B; MCPH1 and RAB2IL1.

The NRG1 fusion gene may be a fusion of at least a portion of the NRG1-gene with a sequence from a different chromosomal location located 3' thereto. Such a NRG1 fusion gene may be a fusion of at least a portion of the NRG1-gene with a sequence from a different chromosomal location CD74, STMN2, PMEPA1, PROSC or PSAP located 3' thereto. The receptors for all NRG1 isoforms are the ErbB family of tyrosine kinase transmembrane receptors. The family is also referred to as the human epidermal growth factor (EGF) receptor family (HER). The family has four members: ErbB (Erythroblastoma)-1, ErbB-2, ErbB-3 and ErbB-4. Epidermal growth factor (EGF) receptor (EGFR, ErbB1, or HER1). The receptors (reviewed in Yarden and Pines 2012) are widely expressed on epithelial cells. Upregulation of HER receptors or their ligands, such as heregulin (HRG) or epidermal growth factor (EGF), is a frequent event in human cancer (Wilson, Fridlyand et al. 2012). Overexpression of ErbB-1 and ErbB-2 in particular occurs in epithelial tumors and is associated with tumor invasion, metastasis, resistance to chemotherapy, and poor prognosis (Zhang, Berezov et al. 2007). In the normal breast, ErbB-3 has been shown to be important in the growth and differentiation of luminal epithelium. For instance, loss/ inhibition of ErbB-3 results in selective expansion of the basal over the luminal epithelium (Balko, Miller et al. 2012). Binding of ligand to the extracellular domain of the RTKs induces receptor dimerization, both between the same (homodimerization) and different (heterodimerization) receptor subtypes. Dimerization can activate the intracellular tyrosine kinase domains, which undergo autophosphorylation and, in turn, can activate a number of downstream pro-proliferative signaling pathways, including those mediated by mitogen-activated protein kinases (MAPK) and the prosurvival pathway Akt (reviewed in Yarden and Pines, 2012). No specific endogenous ligand has been identified for ErbB-2, which is therefore assumed to normally signal through heterodimerization (Sergina, Rausch et al. 2007). ErbB-3 can be activated by engagement of its ligands. These ligands include but are not limited to neuregulin (NRG) and heregulin (HRG).

ErbB-1 is known under various synonyms, the most common of which is EGFR. EGFR has an extracellular domain (ECD) that is composed of four subdomains, two of which are involved in ligand binding and two of which are involved in homo-dimerisation and hetero-dimerisation. EGFR integrates extracellular signals from a variety of ligands to yield diverse intracellular responses. The major signal transduction pathway activated by EGFR is composed of the Ras-mitogen-activated protein kinase (MAPK) mitogenic signalling cascade. Activation of this pathway is initiated by the recruitment of Grb2 to tyrosine phosphorylated EGFR. This leads to activation of Ras through the Grb2-bound Ras-guanine nucleotide exchange factor Son of Sevenless (SOS). In addition, the PI3-kinase-Akt signal transduction pathway is also activated by EGFR, although this activation is much stronger in case there is co-expression of ErbB-3 (HER3). The EGFR is implicated in several human epithelial malignancies, notably cancers of the breast, bladder, non-small cell lung cancer lung, colon, ovarian head and neck and brain. Activating mutations in the gene have been found, as well as over-expression of the receptor and of its ligands, giving rise to autocrine activation loops. This RTK has therefore been extensively used as target for cancer therapy. Both small-molecule inhibitors targeting the RTK and monoclonal antibodies (mAbs) directed to the extracellular ligand-binding domains have been developed and have shown hitherto several clinical successes, albeit mostly for a select group of patients. The database accession number for the human EGFR protein and the gene encoding it is (GenBank NM_005228.3). This accession number is primarily given to provide a further method of identification of EGFR protein as a target, the actual sequence of the EGFR protein bound by an antibody may vary, for instance because of a mutation in the encoding gene such as those occurring in some cancers or the like.

The words cancer and tumor are used herein typically both refer to cancer, unless otherwise specifically stated.

Where reference herein is made to EGFR, the reference refers to human EGFR unless otherwise stated. The antigen-binding site that binds EGFR, binds EGFR and a variety of variants thereof such as those expressed on some EGFR positive tumors.

The term 'ErbB-3' as used herein refers to the protein that in humans is encoded by the ERBB3 gene. Alternative names for the gene or protein are HER3; LCCS2; MDA-BF-1; c-ErbB-3; c-ErbB3; ErbB3-S; p180-ErbB3; p45-sErbB3; and p85-sErbB3. Where reference is made herein to ErbB-3, the reference refers to human ErbB-3. An antibody comprising an antigen-binding site that binds ErbB-3, binds human ErbB-3. The ErbB-3 antigen-binding site may, due to sequence and tertiary structure similarity between human and other mammalian orthologs, also bind such an ortholog but not necessarily so. Database accession numbers for the human ErbB-3 protein and the gene encoding it are (NP_001005915.1, NP_001973.2, NC_000012.11, NC_018923.2, NT_029419.12). The accession numbers are primarily given to provide a further method of identification of ErbB-3 as a target, the actual sequence of the ErbB-3 protein bound by an antibody may vary, for instance because of a mutation in the encoding gene such as those occurring in some cancers or the like. The ErbB-3 antigen binding site binds ErbB-3 and a variety of variants thereof, such as those expressed by some ErbB-3 positive tumor cells. The antigen-binding site that binds ErbB-3 preferably binds domain III of ErbB-3.

The term 'ErbB-2' as used herein refers to the protein that in humans is encoded by the ERBB-2 gene. Alternative names for the gene or protein include CD340; HER-2; HER-2/neu; MLN 19; NEU; NGL; TKR1. The ERBB-2 gene is frequently called HER2 (from human epidermal growth factor receptor 2). Where reference is made herein to ErbB-2, the reference refers to human ErbB-2. An antibody comprising an antigen-binding site that binds ErbB-2, binds human ErbB-2. The ErbB-2 antigen-binding site may, due to sequence and tertiary structure similarity between human and other mammalian orthologs, also bind such an ortholog but not necessarily so. Database accession numbers for the human ErbB-2 protein and the gene encoding it are (NP_001005862.1, NP_004439.2 NC_000017.10 NT_010783.15 NC_018928.2). The accession numbers are primarily given to provide a further method of identification of ErbB-2 as a target, the actual sequence of the ErbB-2 protein bound the antibody may vary, for instance because of a mutation in the encoding gene such as those occurring in some cancers or the like. The ErbB-2 antigen binding site binds ErbB-2 and a variety of variants thereof, such as those expressed by some ErbB-2 positive tumor cells. The antigen-binding site that binds ErbB-2 preferably binds domain I of ErbB-2.

CD74 is known under number of aliases. Some of these are CD74 Molecule; CD74 Antigen (Invariant Polypeptide Of Major Histocompatibility Complex, Class II Antigen-Associated); CD74 Molecule, Major Histocompatibility Complex, Class II Invariant Chain; HLA-DR Antigens-Associated Invariant Chain; Gamma Chain Of Class II Antigens; Ia-Associated Invariant Chain; MHC HLA-DR Gamma Chain; HLA-DR-Gamma; DHLAG; P33; HLA Class II Histocompatibility Antigen Gamma Chain; Ia Antigen-Associated Invariant Chain; la-GAMMA and HLADG. External Ids for CD74 are HGNC: 1697; Entrez Gene: 972; Ensembl: ENSG00000019582; OMIM: 142790 and UniProtKB: P04233.

DOC4 or Teneurin Transmembrane Protein 4 (TENM4) is known under a number of different names such as Protein Odd Oz/Ten-M Homolog 4; Tenascin-M4; Ten-M4; Ten-4; ODZ4; TNM4; Odz, Odd Oz/Ten-M Homolog 4 (*Drosophila*); Odz, Odd Oz/Ten-M Homolog 4; Teneurin-4; KIAA1302; Doc4; and ETM5. External Ids for DOC4 are HGNC: 29945; Entrez Gene: 26011; Ensembl: ENSG00000149256; OMIM: 610084 and UniProtKB: Q6N022.

TNFRSF10B or TNF Receptor Superfamily Member 10b is known under a number of different names Tumor Necrosis Factor Receptor Superfamily, Member 10b; TNF-Related Apoptosis-Inducing Ligand Receptor 2; Death Receptor 5; TRAIL-R2; TRAILR2; KILLER; TRICK2; ZTNFR9; DR5; P53-Regulated DNA Damage-Inducible Cell Death Receptor (Killer); Tumor Necrosis Factor Receptor Superfamily Member 10B; Tumor Necrosis Factor Receptor-Like Protein ZTNFR9; Death Domain Containing Receptor For TRAIL/Apo-2L; poptosis Inducing Protein TRICK2A/2B; Apoptosis Inducing Receptor TRAIL-R2; Cytotoxic TRAIL Receptor-2; Fas-Like Protein; TRAIL Receptor 2; CD262 Antigen; KILLER/DR5; TRICK2B; TRICK2A; TRICKB; and CD262. External Ids for TNFRSF10B are HGNC: 11905; Entrez Gene: 8795; Ensembl: ENSG00000120889; OMIM: 603612; and UniProtKB: O14763.

The CLU gene or Clusterin is known under a number of different names such as Testosterone-Repressed Prostate Message 2; Apolipoprotein J; Complement-Associated Protein SP-40,40; Complement Cytolysis Inhibitor; Complement Lysis Inhibitor; Sulfated Glycoprotein 2; Ku70-Binding Protein 1; NA1/NA2; TRPM-2; APO-J; APOJ; KUB1; CLI; Clusterin (Complement Lysis Inhibitor, SP-40,40, Sulfated Glycoprotein 2, Testosterone-Repressed Prostate Message 2, Apolipoprotein J); Aging-Associated Gene 4 Protein; Aging-Associated Protein 4; SGP-2; SP-40; TRPM2; AAG4; CLU1; CLU2; and SGP2. External Ids for CLU are HGNC: 2095; Entrez Gene: 1191; Ensembl: ENSG00000120885; OMIM: 185430; and UniProtKB: P10909.

VAMP2 or Vesicle Associated Membrane Protein 2 is known under a number of different names such as synaptobrevin 2; SYB2; Vesicle-Associated Membrane Protein 2; and Synaptobrevin-2. External Ids for VAMP2 are HGNC: 12643; Entrez Gene: 6844; Ensembl: ENSG00000220205; OMIM: 185881; and UniProtKB: P63027.

SLCA3A2 or Solute Carrier Family 3 Member 2 is known under a number of different names such as Lymphocyte Activation Antigen 4F2 Large Subunit; Solute Carrier Family 3 (Activators Of Dibasic And Neutral Amino Acid Transport), Member 2; Antigen Identified By Monoclonal Antibodies 4F2, TRA1.10, TROP4, And T43; Solute Carrier Family 3 (Amino Acid Transporter Heavy Chain), Member 2; 4F2 Cell-Surface Antigen Heavy Chain; CD98 Heavy Chain; 4F2HC; MDU1; Antigen Defined By Monoclonal Antibody 4F2, Heavy Chain; Antigen Defined By Monoclonal Antibody 4F2; 4F2 Heavy Chain Antigen; 4F2 Heavy Chain; CD98 Antigen; CD98HC; 4T2HC; NACAE; CD98 and 4F2. External Ids for SLC3A2 are HGNC: 11026; Entrez Gene: 6520; Ensembl: ENSG00000168003; OMIM: 158070; and UniProtKB: P08195.

RBPMS or RNA Binding Protein With Multiple Splicing is known under a number of different names such as RNA Binding Protein With Multiple Splicing; Heart And RRM Expressed Sequence; HERMES; RNA-Binding Protein With Multiple Splicing; and RBP-MS. External Ids for RBPMS are HGNC: 19097; Entrez Gene: 11030; Ensembl: ENSG00000157110; OMIM: 601558; and UniProtKB: Q93062.

WRN or Werner Syndrome RecQ Like Helicase is known under a number of different names such as Werner Syndrome RecQ Like Helicase; DNA Helicase, RecQ-Like Type 3; RecQ Protein-Like 2; Exonuclease WRN; RECQL2; RECQ3; Werner Syndrome ATP-Dependent Helicase; Werner Syndrome, RecQ Helicase-Like; Werner Syndrome; EC 3.6.4.12; EC 3.1.-.-; EC 3.6.1; and RECQL3. External Ids for WRN are HGNC: 12791; Entrez Gene: 7486; Ensembl: ENSG00000165392; OMIM: 604611 and UniProtKB: Q14191.

SDC4 or Syndecan 4 is known under a number of different names such as Syndecan 4 (Amphiglycan, Ryudocan); Syndecan Proteoglycan 4; Ryudocan Core Protein; Amphiglycan; SYND4; Ryudocan Amphiglycan; and Syndecan-4. External Ids for SDC4 are HGNC: 10661; Entrez Gene: 6385; Ensembl: ENSG00000124145; OMIM: 600017; and UniProtKB: P31431.

Various NRG1 fusion genes are described in Dhanasekaran et al (2014).

The invention provides methods of an individual that has an ErbB-2 and ErbB-3 positive cell or tumor. Alternatively, the individual may be at risk of having a tumor. The method comprises administering a bispecific antibody that comprises a first antigen-binding site that can bind an extracellular part of ErbB-2 and a second antigen-binding site that can bind an extracellular part of ErbB-3 to the individual in need thereof. The method is characterized in that the cell or cells of the tumor comprises an NRG1 fusion gene comprising the 3' end of the NRG1-gene fused to a 5' sequence from a different chromosomal location.

The cell may be a cancer cell. Said cancer cell may be a cancer cell associated with an NRG1-fusion, for example a cancer cell driven by an NRG1-fusion.

Antigen-binding sites in an antibody are typically present in the variable domains. The variable domains comprise a heavy chain variable region and a light chain variable region.

The individual has preferably undergone a therapy that targeted towards EGFR inhibition, preferably with an EGFR binding antibody, which is preferably cetuximab.

A method of treatment of the invention preferably further comprises determining the number of ErbB-1 cell-surface receptor; ErbB-2 cell-surface receptor; ErbB-3 cell-surface receptor; ErbB-4 cell-surface receptor or a combination thereof on the cell or cells of the tumor.

A method of treatment of the invention preferably further comprises determining whether the cell comprises an NRG1-fusion or whether the tumor comprises cells with an NRG1-fusion. This can for instance be done on cells of a biopsy. Various methods are available and many are known in the art. Known that region wherein the chromosome break occurs in the case of NRG1-fusions it is routine for the skilled person to determine whether a tumor comprises such an NRG1-fusion. One way is by means of PCR-amplification with primers that span the junction in the NRG1 fusion. This can easily be implemented for NRG1-fusions that are known to occur. New fusions can also be detected easily. A suitable way is for instance by junction cloning techniques used to find for instance the integration site of retroviral genomes. A suitable method is by means of LAM-PCR see Schmidt et al Nature Methods 4, 1051-1057 (2007) doi: 10.1038/nmeth1103 and specific references to the LAM-technology therein.

A method of treatment of the invention is preferably characterized in that the cell or tumor has less than 400,000 ErbB-1 cell-surface receptors per cell, preferably less than 200.000 ErbB-1 cell-surface receptors per cell.

In a preferred embodiment the method of treatment of the invention further comprises administering to the individual an ErbB-1 inhibitor, preferably cetuximab.

The method of treatments as defined herein can also be defined as a compound or combination of compounds for use in the treatment of. Suitable combination of compounds are a bispecific antibody as defined herein and an ErbB-1 inhibitor.

To establish whether a cell or tumor is positive for ErbB-2 and ErbB-3 the skilled person can for instance determine the ErbB-2 and ErbB-3 amplification and/or staining in immunohistochemistry. At least 10% tumor cells in a biopsy should be positive for both ErbB-2 and for ErbB-3. The biopsy can also contain 20%, 30% 40% 50% 60% 70% or more positive cells. ErbB-1 positive tumors can be similarly identified.

Preferably said positive cancer is a breast cancer, such as early-stage breast cancer. However, the invention can be applied to a wide range of ErbB-2, ErbB-3 or ErbB-2/ErbB-3 positive cancers, like gastric cancer, colorectal cancer, colon cancer, gastro-esophageal cancer, esophageal cancer, endometrial cancer, ovarian cancer, breast cancer, liver cancer, lung cancer, including non-small cell lung cancer, clear cell sarcoma, salivary gland cancer, head and neck cancer, brain cancer, bladder cancer, pancreatic cancer, prostate cancer, kidney cancer, skin cancer, melanoma, and the like. The cell is preferably an epithelial cell. Alternatively, the cell or tumor is preferably a cell or tumor of an epithelial origin. In a preferred embodiment the cell or tumor is a breast cancer, an ovarian cancer, a lung cancer, or a metastasis thereof. Preferably the tumor is of epithelial origin. Preferably, the tumor is a breast cancer, an ovarian cancer, a lung cancer, or a metastasis thereof.

Patients with ErbB 2 positive cells or tumor cells can be classified based on the number of ErbB-2 receptors on the tumor cell surface. Tumors with more than 1,000,000 ErbB-2 receptors on their cell surface are typically classified as ErbB-2 [+++], those with between 150,000 to 1,000,000 are classified as ErbB-2 [++], and those with less than 150,000 are classified as ErbB-2[+]. Preferably, the patient is classified as ErbB-2[++] or ErbB-2 [+++]. Preferably, the ErbB-2/ErbB-3 positive tumor has at least 1,000,000 ErbB-2 cell-surface receptors per cell.

Preferably, methods are provided in which the ErbB-2/ErbB-3 positive cell or tumor has at least 150,000 ErbB-2 cell-surface receptors per cell and less than 50,000 ErbB-3 cell-surface receptors per cell. Preferably, methods are provided in which the ErbB-2/ErbB-3 positive cell or tumor has at least 1,00,000 ErbB-2 cell-surface receptors per cell and less than 50,000 ErbB-3 cell-surface receptors per cell.

In some embodiments, the methods disclosed herein are advantageous in that specific patient populations are first determined based on, e.g., the ErbB-1, ErbB-2, and/or ErbB-3 cell-surface receptor density. Accordingly, the methods disclosed herein preferably comprise determining the ErbB-1 cell-surface receptor density, ErbB-2 cell-surface receptor density, ErbB-3 cell-surface receptor density and/or ErbB-4 cell-surface receptor density for said cell or tumor. As used herein, the term cell-surface receptors density refers to the number of receptors present at the cell-surface per cell.

Preferably, the methods disclosed herein further comprise determining the ErbB-2 cell-surface receptor density for said cell or tumor. Patients may be classified using immunohistochemistry or fluorescence in situ hybridization. The HercepTest™ and/or HER2 FISH (pharm Dx™), marketed both by Dako Denmark A/S, and/or using a HERmark® assay, marketed by Monogram Biosciences are examples of suitable assays for determining ErbB-2 or ErbB-3 cell surface receptor density. Other methods for determining the ErbB-2 receptor cell density are well-known to a skilled person. In vivo methods for determining ErbB-2 are also known, see, e.g., Chernomoridik et al. Mol Imaging. 2010 August; 9(4): 192-200 and Ardeshirpour et al. Technol Cancer Res Treat. 2014 October; 13(5): 427-434. Preferably, the methods disclosed herein further comprise determining the ErbB-2 cell-surface receptor density for said cell or tumor. Such methods are known to a skilled person (see, e.g., van der Woning and van Zoelen Biochem Biophys Res Commun. 2009 Jan. 9; 378(2):285-9). Preferably, the methods disclosed herein further comprise determining the ErbB-1 cell-surface receptor density for said cell or tumor. Such methods are known to a skilled person (see, e.g., EGFR pharmDx™ Kit (Dako)) and McDonagh et al. Mol Cancer Ther 2012; 11:582). Similar methods can be used to determine ErbB-4 cell-surface receptor density.

In some embodiments, the ErbB-1, ErbB-2, ErbB-3, and ErbB-4 cell-surface receptor densities are determined by FACS analysis on biopsied tumor cells.

Preferably, the cells of the ErbB-2/ErbB-3 positive cell or tumor have relatively high levels of heregulin expression. Heregulin is a growth factor that is involved in growth of ErbB 3 positive cell or tumor cells. Typically, when the cell or tumor cells express high levels of heregulin (referred to as heregulin stress), currently known therapies like trastuzumab, pertuzumab and lapatinib are no longer capable of inhibiting cell or tumor growth. This phenomenon is called heregulin resistance. In particular, the heregulin expression level that is greater than the heregulin expression level of MCF7 cells. Heregulin expression levels are for instance measured using qPCR with cell or tumor RNA (such as for instance described in Shames et al. PLOS ONE, February 2013, Vol. 8, Issue 2, pp 1-10 and in Yonesaka et al., Sci. transl. Med., Vol. 3, Issue 99 (2011); pp 1-11), or using protein detection methods, like for instance ELISA, preferably using blood, plasma or serum samples (such as for instance described in Yonesaka et al., Sci. transl. Med., Vol. 3, Issue 99 (2011); pp 1-11).

High heregulin levels are typically present during the formation of metastases (i.e. the migration, invasion, growth and/or differentiation of a cell or tumor cells or tumor initiating cells). Typically, tumor initiating cells are identified based on stem cell markers such as for instance CD44, CD24, CD133 and/or ALDH1. These processes can therefore barely be counteracted with currently known therapies like trastuzumab and pertuzumab. The bispecific antibodies disclosed herein are capable of counteracting the formation of metastases in subjects having cells tumors that comprise an NRG1 fusion gene comprising the 3' end of the NRG1-gene fused to a 5' sequence from a different chromosomal location.

Further provided is therefore a method for counteracting the formation of a metastasis in a subject having a ErbB-2, ErbB-3 or ErbB-2/ErbB-3 positive cell or tumor, wherein said ErbB-2, ErbB-3 or ErbB-2/ErbB-3 positive cell or tumor cell has a heregulin expression level that is at least 60%, preferably at least 70%, more preferably at least 80%, more preferably at least 85%, more preferably at least 90% or 95% of the heregulin expression level of BXPC3 or MCF7 cells, comprising administering to the subject a bispecific antibody comprising a first antigen-binding site that binds ErbB-2 and a second antigen-binding site that binds ErbB-3. Also provided is a bispecific antibody comprising a first antigen-binding site that binds ErbB-2 and a second antigen-binding site that binds ErbB-3 for use in the treatment or prevention of the formation of metastases, wherein said ErbB-2, ErbB-3 or ErbB-2/ErbB-3 positive cell or tumor cell has a heregulin expression level that is at least 60%, preferably at least 70%, more preferably at least 80%, more preferably at least 85%, more preferably at least 90% or 95% of the heregulin expression level of BXPC3 or MCF7 cells. Further provided is a use of a bispecific antibody according to the invention for the preparation of a medicament for the treatment or prevention of the formation of metastases, wherein said ErbB-2, ErbB-3 or ErbB-2/ErbB-3 positive cell or tumor cell has a heregulin expression level that is at least 60%, preferably at least 70%, more preferably at least 80%, more preferably at least 85%, more preferably at least 90% or 95% of the heregulin expression level of BXPC3 or MCF7 cells.

The subject is preferably a human subject. The subject is preferably a subject eligible for monoclonal antibody therapy using an ErbB-2 specific antibody such as trastuzumab.

The amount of bispecific to be administered to a patient is typically in the therapeutic window, meaning that a sufficient quantity is used for obtaining a therapeutic effect, while the amount does not exceed a threshold value leading to an unacceptable extent of side-effects. The lower the amount of antibody needed for obtaining a desired therapeutic effect, the larger the therapeutic window will typically be. The selected dosage level will depend upon a variety of factors including the route of administration, the time of administration, the rate of excretion of the particular compound being employed, the duration of the treatment, other drugs, compounds and/or materials used in combination, the age, sex, weight, condition, general health and prior medical history of the patient being treated, and like factors well known in the medical arts. The dosage can be in the range of the dosing regime for trastuzumab or lower.

The bispecific antibodies can be formulated as a pharmaceutical composition comprising a pharmaceutically acceptable carrier, diluent, or excipient, and additional, optional, active agents. The antibodies and compositions comprising the antibodies can be administered by any route including parenteral, enteral, and topical administration. Parenteral administration is usually by injection, and includes, e.g., intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, intratumoral, and intrasternal injection and infusion.

In preferred embodiments, an ErbB-1 inhibitor can be combined with treatment with the bispecific antibodies disclosed herein. The ErbB-1 inhibitor can be administered simultaneously or sequentially with the bispecific antibody. Treatment with the ErbB-1 inhibitor can be separated by several minutes, hours, or days from the treatment with the bispecific antibody. Preferably, the ErbB-2/ErbB3 cell or tumor is also positive for ErbB1. Preferably, the combination treatment is suitable for ErbB-2/ErbB3 cells or tumors having more than 5,000 surface receptors per cell, preferably at least 20,000 surface receptors per cell, more preferably more than 50,000 surface receptors per cell.

Suitable ErbB-1 inhibitors are known in the art and refer to compounds that inhibit at least one biological activity of ErbB-1 (EGFR), in particular a compound that decreases the expression or signaling activity of ErbB-1. Preferred ErbB-1 inhibitors bind to the extracellular binding site of the tyrosine kinase receptor molecule and block binding of the natural ligands, such as EGF. Such inhibitors include antibodies, antibody portions, and peptides comprising epitopes that target this extracellular EGF receptor binding domain. Preferably, the ErbB-1 inhibitor is an anti-ErbB-1 antibody, preferably selected from cetuximab, matuzumab, necitumumab, nimotuzumab, panitumumab, or zalutumumab. The invention is further related to ErbB-1 inhibitors which can bind or interact with the intracellular phosphorylation site or domain of the tyrosine kinase receptor molecule, such preventing or decreasing phosphorylation by tyrosine kinase. This can be achieved by small (chemical) molecule drugs. Preferred inhibitors include afatinib, erlotinib, gefitinib, lapatinib, osimertinib, and neratinib.

The disclosure provides bispecific antibodies for use in the methods and treatments described herein. Suitable bispecific antibodies comprise a first antigen-binding site that binds ErbB-2 and a second antigen-binding site that binds ErbB-3, wherein the bispecific antibody reduces or can reduce a ligand-induced receptor function of ErbB-3 on an ErbB-2 and ErbB-3 positive cell. Preferred antibodies and their preparation are disclosed in WO 2015/130173, which is hereby incorporated by reference. The examples in WO 2015/130173 further describe a number of properties of the antibodies, such as ligand binding and epitope mapping.

As used herein, the term "antigen-binding site" refers to a site derived from and preferably as present on a bispecific antibody which is capable of binding to antigen. An unmodified antigen-binding site is typically formed by and present in the variable domain of the antibody. The variable domain contains said antigen-binding site. A variable domain that binds an antigen is a variable domain comprising an antigen-binding site that binds the antigen.

In one embodiment an antibody variable domain comprises a heavy chain variable region (VH) and a light chain variable region (VL). The antigen-binding site can be present in the combined VH/VL variable domain, or in only the VH region or only the VL region. When the antigen-binding site is present in only one of the two regions of the variable domain, the counterpart variable region can contribute to the folding and/or stability of the binding variable region, but does not significantly contribute to the binding of the antigen itself.

As used herein, antigen-binding refers to the typical binding capacity of an antibody to its antigen. An antibody comprising an antigen-binding site that binds to ErbB-2, binds to ErbB-2 and, under otherwise identical conditions, at least 100-fold lower to the homologous receptors ErbB-1 and ErbB-4 of the same species. An antibody comprising an antigen-binding site that binds to ErbB-3, binds to ErbB-3 and, under otherwise identical conditions, not to the homologous receptors ErbB-1 and ErbB-4 of the same species. Considering that the ErbB-family is a family of cell surface receptors, the binding is typically assessed on cells that express the receptor(s). Binding of an antibody to an antigen can be assessed in various ways. One way is to incubate the antibody with the antigen (preferably cells expressing the antigen), removing unbound antibody (preferably by a wash step) and detecting bound antibody by means of a labeled antibody that binds to the bound antibody.

Antigen binding by an antibody is typically mediated through the complementarity regions of the antibody and the specific three-dimensional structure of both the antigen and the variable domain allowing these two structures to bind together with precision (an interaction similar to a lock and key), as opposed to random, non-specific sticking of antibodies. As an antibody typically recognizes an epitope of an antigen, and as such epitope may be present in other compounds as well, antibodies according to the present invention that bind ErbB-2 and/or ErbB-3 may recognize other proteins as well, if such other compounds contain the same epitope. Hence, the term "binding" does not exclude binding of the antibodies to another protein or protein(s) that contain the same epitope. Such other protein(s) is preferably not a human protein. An ErbB-2 antigen-binding site and an ErbB-3 antigen-binding site as defined herein typically do not bind to other proteins on the membrane of cells in a post-natal, preferably adult human. A bispecific antibody as disclosed herein is typically capable of binding ErbB-2 and ErbB-3 with a binding affinity of at least $1 \times 10e$-6 M, as outlined in more detail below.

The term "interferes with binding" as used herein means that the antibody is directed to an epitope on ErbB-3 and the antibody competes with ligand for binding to ErbB-3. The antibody may diminish ligand binding, displace ligand when this is already bound to ErbB-3 or it may, for instance through steric hindrance, at least partially prevent that ligand can bind to ErbB-3.

The term "antibody" as used herein means a proteinaceous molecule, preferably belonging to the immunoglobulin class of proteins, containing one or more variable domains that bind an epitope on an antigen, where such domains are derived from or share sequence homology with the variable domain of an antibody. Antibodies for therapeutic use are preferably as close to natural antibodies of the subject to be treated as possible (for instance human antibodies for human subjects). Antibody binding can be expressed in terms of specificity and affinity. The specificity determines which antigen or epitope thereof is specifically bound by the binding domain. The affinity is a measure for the strength of binding to a particular antigen or epitope. Specific binding, is defined as binding with affinities (KD) of at least $1 \times 10e$-6 M, more preferably $1 \times 10e$-7 M, more preferably higher than $1 \times 10e$-9 M. Typically, antibodies for therapeutic applications have affinities of up to $1 \times 10e$-10 M or higher. Antibodies such the bispecific antibodies of the present invention comprise the constant domains (Fc part) of a natural antibody. An antibody of the invention is typically a bispecific full length antibody, preferably of the human IgG subclass. Preferably, an antibody as disclosed herein is of the human IgG1 subclass. Such antibodies have good ADCC properties, have favorable half life upon in vivo administration to humans and CH3 engineering technology exists that can provide for modified heavy chains that preferentially form heterodimers over homodimers upon co-expression in clonal cells.

An antibody as disclosed herein is preferably a "full length" antibody. The term 'full length' is defined as comprising an essentially complete antibody, which however does not necessarily have all functions of an intact antibody. For the avoidance of doubt, a full length antibody contains two heavy and two light chains. Each chain contains constant (C) and variable (V) regions, which can be broken down into domains designated CH1, CH2, CH3, VH, and CL, VL. An antibody binds to antigen via the variable domains contained in the Fab portion, and after binding can interact with molecules and cells of the immune system through the constant domains, mostly through the Fc portion. The terms 'variable domain', 'VH/VL pair', 'VH/VL' are used herein interchangeably. Full length antibodies according to the invention encompass antibodies wherein mutations may be present that provide desired characteristics. Such mutations should not be deletions of substantial portions of any of the regions. However, antibodies wherein one or several amino acid residues are deleted, without essentially altering the binding characteristics of the resulting antibody are embraced within the term "full length antibody". For instance, an IgG antibody can have 1-20 amino acid residue insertions, deletions or a combination thereof in the constant region. For instance, ADCC activity of an antibody can be improved when the antibody itself has a low ADCC activity, by slightly modifying the constant region of the antibody (Junttila, T. T., K. Parsons, et al. (2010). "Superior In vivo Efficacy of Afucosylated Trastuzumab in the Treatment of HER2-Amplified Breast Cancer." Cancer Research 70(11): 4481-4489)

Full length IgG antibodies are preferred because of their favourable half life and the need to stay as close to fully autologous (human) molecules for reasons of immunogenicity. An antibody as disclosed herein is preferably a bispecific IgG antibody, preferably a bispecific full length IgG1 antibody. IgG1 is favoured based on its long circulatory half life in man. In order to prevent any immunogenicity in humans it is preferred that the bispecific IgG antibody is a human IgG1.

The term 'bispecific' (bs) means that one part of the antibody (as defined above) binds to one epitope on an antigen whereas a second part binds to a different epitope. The different epitope is typically present on a different antigen. The first and second antigens are in fact two different proteins. A preferred bispecific antibody is an antibody that comprises parts of two different monoclonal antibodies and consequently binds to two different types of antigen. One arm of the bispecific antibody typically contains the variable domain of one antibody and the other arm contains the variable domain of another antibody. The heavy chain variable regions of the bispecific antibody are typically different from each other, whereas the light chain variable regions are preferably the same. A bispecific antibody wherein the different heavy chain variable regions are associated with the same, or a common, light chain is also referred to as a bispecific antibody with a common light chain.

Preferred bispecific antibodies can be obtained by co-expression of two different heavy chains and a common light chain in a single cell. When wildtype CH3 domains are used, co-expression of two different heavy chains and a common light chain will result in three different species, AA, AB and BB. To increase the percentage of the desired bispecific product (AB) CH3 engineering can be employed, or in other words, one can use heavy chains with compatible heterodimerization domains, as defined hereunder.

The term 'compatible heterodimerization domains' as used herein refers to protein domains that are engineered such that engineered domain A' will preferentially form heterodimers with engineered domain B' and vice versa, whereas homodimerization between A'-A' and B'-B' is diminished.

The term 'common light chain' refers to light chains which may be identical or have some amino acid sequence differences while the binding specificity of the full length antibody is not affected. It is for instance possible, to prepare or find light chains that are not identical but still functionally equivalent, e.g., by introducing and testing conservative amino acid changes, changes of amino acids in regions that do not or only partly contribute to binding specificity when paired with the heavy chain, and the like. The terms 'common light chain', 'common VL', 'single light chain', 'single VL', with or without the addition of the term 'rearranged' are all used herein interchangeably.

A common light chain (variable region) preferably has a germline sequence. A preferred germline sequence is a light chain variable region that is frequently used in the human repertoire and has good thermodynamic stability, yield and solubility. In a preferred embodiment the light chain comprises a light chain region comprising the amino acid sequence of an O12/IgVκ1-39*01 gene segment as depicted in the Sequences 1C "Common light chain IGKV1-39/jk1" with 0-10, preferably 0-5 amino acid insertions, deletions, substitutions, additions or a combination thereof. IgVκ1-39 is short for Immunoglobulin Variable Kappa 1-39 Gene. The gene is also known as Immunoglobulin Kappa Variable 1-39; IGKV139; IGKV1-39; O12a or O12. External Ids for the gene are HGNC: 5740; Entrez Gene: 28930; Ensembl: ENSG00000242371. The variable region of IGKV1-39 is listed in the Sequences 1C. The V-region can be combined with one of five J-regions. Sequences 1C describe two preferred sequences for IgVκ1-39 in combination with a J-region. The joined sequences are indicated as IGKV1-39/jk1 and IGKV1-39/jk5; alternative names are IgVκ1-39*01/IGJκ1*01 or IgVκ1-39*01/IGJκ5*01 (nomenclature according to the IMGT database worldwide web at imgt.org).

It is preferred that the O12/IgVκ1-39*01 comprising light chain variable region is a germline sequence. It is further preferred that the IGJκ1*01 or/IGJκ5*01 comprising light chain variable region is a germline sequence. In a preferred embodiment, the IGKV1-39/jk1 or IGKV1-39/jk5 light chain variable regions are germline sequences.

In a preferred embodiment the light chain variable region comprises a germline O12/IgVκ1-39*01. In a preferred embodiment the light chain variable region comprises the kappa light chain IgVκ1-39*01/IGJκ1*01 or IgVκ1-39*01/IGJκ5*01. In a preferred embodiment a IgVκ1-39*01/IGJκ1*01. The light chain variable region preferably comprises a germline kappa light chain IgVκ1-39*01/IGJκ1*01 or germline kappa light chain IgVκ1-39*01/IGJκ5*01, preferably a germline IgVκ1-39*01/IGJκ1*01.

Obviously, those of skill in the art will recognize that "common" also refers to functional equivalents of the light chain of which the amino acid sequence is not identical. Many variants of said light chain exist wherein mutations (deletions, substitutions, additions) are present that do not materially influence the formation of functional binding regions. The light chain can also be a light chain as specified herein above, having 1-5 amino acid insertions, deletions, substitutions or a combination thereof.

Preferably, both the first antigen binding site and said second antigen binding site comprise a light chain variable region comprising a CDR1 having the sequence (RASQSISSYLN; SEQ ID NO: 75), a CDR2 having the sequence (AASSLQS; SEQ ID NO: 76), and a CDR3 having the sequence (QQSYSTPPT; SEQ ID NO: 77).

The term 'ErbB-' as used herein refers to the protein that in humans is encoded by the ERBB-1 gene. Alternative names for the gene or protein include EGFR, ERBB, HER1, Erb-B2 receptor tyrosine kinase 1. Where reference is made herein to ErbB-1, the reference refers to human ErbB-1.

The term 'ErbB-2' as used herein refers to the protein that in humans is encoded by the ERBB-2 gene. Alternative names for the gene or protein include CD340; HER-2; HER-2/neu; MLN 19; NEU; NGL; TKR1. The ERBB-2 gene is frequently called HER2 (from human epidermal growth factor receptor 2). Where reference is made herein to ErbB-2, the reference refers to human ErbB-2. An antibody comprising an antigen-binding site that binds ErbB-2, binds human ErbB-2. The ErbB-2 antigen-binding site may, due to sequence and tertiary structure similarity between human and other mammalian orthologs, also bind such an ortholog but not necessarily so. Database accession numbers for the human ErbB-2 protein and the gene encoding it are (NP_001005862.1, NP_004439.2 NC_000017.10 NT_010783.15 NC_018928.2). The accession numbers are primarily given to provide a further method of identification of ErbB-2 as a target, the actual sequence of the ErbB-2 protein bound the antibody may vary, for instance because of a mutation in the encoding gene such as those occurring in some cancers or the like. The ErbB-2 antigen binding site binds ErbB-2 and a variety of variants thereof, such as those expressed by some ErbB-2 positive cells or tumor cells.

The term 'ErbB-3' as used herein refers to the protein that in humans is encoded by the ERBB-3 gene. Alternative names for the gene or protein are HER3; LCCS2; MDA-BF-1; c-ErbB-3; c-erbb-3; erbb-3-S; p180-Erbb-3; p45-sErbb-3; and p85-sErbb-3. Where reference is made herein to ErbB-3, the reference refers to human ErbB-3. An antibody comprising an antigen-binding site that binds ErbB-3, binds human ErbB-3. The ErbB-3 antigen-binding site, may, due to sequence and tertiary structure similarity between human and other mammalian orthologs, also bind such an ortholog but not necessarily so. Database accession numbers for the human ErbB-3 protein and the gene encoding it are (NP_001005915.1 NP_001973.2, NC_000012.11 NC_018923.2 NT_029419.12). The accession numbers are primarily given to provide a further method of identification of ErbB-3 as a target, the actual sequence of the ErbB-3 protein bound by an antibody may vary, for instance because of a mutation in the encoding gene such as those occurring in some cancers or the like. The ErbB-3 antigen binding site binds ErbB-3 and a variety of variants thereof, such as those expressed by some ErbB-2 positive cells or tumor cells.

The term 'ErbB-4' as used herein refers to the protein that in humans is encoded by the ERBB-4 gene. Alternative names for the gene or protein include HER4, Erb-B2 receptor tyrosine kinase 4, and Human Epidermal Growth Factor Receptor 4. Where reference is made herein to ErbB-1, the reference refers to human ErbB-4.

The antibodies disclosed herein can reduce a ligand-induced receptor function of ErbB-3 on an ErbB-2 and ErbB-3 positive cell. In the presence of excess ErbB-2, ErbB-2/ErbB-3 heterodimers may provide a growth signal to the expressing cell in the absence of detectable ligand for the ErbB-3 chain in the heterodimer. This ErbB-3 receptor function is herein referred as a ligand-independent receptor function of ErbB-3. The ErbB-2/ErbB-3 heterodimer also provide a growth signal to the expressing cell in the presence of an ErbB-3 ligand. This ErbB-3 receptor function is herein referred to as a ligand-induced receptor function of ErbB-3.

The term "ErbB-3 ligand" as used herein refers to polypeptides which bind and activate ErbB-3. Examples of ErbB-3 ligands include, but are not limited to neuregulin 1 (NRG) and neuregulin 2, betacellulin, heparin-binding epidermal growth factor, and epiregulin. The term includes biologically active fragments and/or variants of a naturally occurring polypeptide.

Preferably, the ligand-induced receptor function of ErbB-3 is ErbB-3 ligand-induced growth of an ErbB-2 and ErbB-3 positive cell. In a preferred embodiment said cell is an MCF-7 cell (ATCC® HTB-22™); an SKBR3 (ATCC® HTB-30™) cell; an NCI-87 (ATCC® CRL-5822™) cell; a BxPC-3-luc2 cell (Perkin Elmer 125058), a BT-474 cell (ATCC® HTB-20™) or a JIMT-1 cell (DSMZ no.: ACC 589).

As used herein the ligand-induced receptor function is reduced by at least 20%, preferably at least 30, 40, 50 60, or at least 70% in a particularly preferred embodiment the ligand-induced receptor function is reduced by 80, more preferably by 90%. The reduction is preferably determined by determining a ligand-induced receptor function in the presence of a bispecific antibody disclosed herein, and comparing it with the same function in the absence of the antibody, under otherwise identical conditions. The conditions comprise at least the presence of an ErbB-3 ligand. The amount of ligand present is preferably an amount that induces half of the maximum growth of an ErbB-2 and ErbB-3 positive cell line. The ErbB-2 and ErbB-3 positive cell line for this test is preferably the MCF-7 cell line (ATCC® HTB-22™), the SKBR3 cell line (ATCC® HTB-30™) cells, the JIMT-1 cell line (DSMZ ACC 589) or the NCI-87 cell line (ATCC® CRL-5822™). The test and/or the ligand for determining ErbB-3 ligand-induced receptor function is preferably a test for ErbB-3 ligand induced growth reduction as specified in the examples.

The ErbB-2 protein contains several domains (see for reference FIG. 1 of Landgraf, R Breast Cancer Res. 2007; 9(1): 202-). The extracellular domains are referred to as domains I-IV. The place of binding to the respective domains of antigen-binding sites of antibodies described herein has been mapped. A bispecific antibody with an antigen-binding site (first antigen-binding site) that binds domain I or domain IV of ErbB-2 (first antigen-binding site) comprises a heavy chain variable region that maintains significant binding specificity and affinity for ErbB-2 when combined with various light chains. Bispecific antibodies with an antigen-binding site (first antigen-binding site) that binds domain I or domain IV of ErbB-2 (first antigen-binding site) and an antigen-binding site for ErbB-3 (second antigen-binding site) are more effective in reducing a ligand-induced receptor function of ErbB-3 when compared to a bispecific antibody comprising an antigen-binding site (first antigen-binding site) that binds to another extra-cellular domain of ErbB-2. A bispecific antibody comprising an antigen-binding site (first antigen-binding site) that binds ErbB-2, wherein said antigen-binding site binds to domain I or domain IV of ErbB-2 is preferred. Preferably said antigen-binding site binds to domain IV of ErbB-2. Preferred antibodies comprises a first antigen-binding site that binds domain I of ErbB-2 and a second antigen-binding site that binds domain III of ErbB-3.

In one preferred embodiment, said antibody comprises an antigen-binding site that binds at least one amino acid of domain I of ErbB-2 selected from the group consisting of T144, T164, R166, P172, G179, S180 and R181, and surface-exposed amino acid residues that are located within about 5 amino acid positions from T144, T164, R166, P172, G179, S180 or R181.

In one preferred embodiment, said antibody preferably comprises an antigen-binding site that binds at least one amino acid of domain III of ErbB-3 selected from the group consisting of R426 and surface-exposed amino acid residues that are located within 11.2 Å from R426 in the native ErbB-3 protein.

A bispecific antibody with an antigen-binding site (first antigen-binding site) that binds ErbB-2, and that further comprises ADCC are more effective than other ErbB-2 binding antibodies that did not have significant ADCC activity, particularly in vivo. A bispecific antibody which exhibits ADCC is therefore preferred. It was found that antibodies wherein said first antigen-binding site binds to domain IV of ErbB-2 had intrinsic ADCC activity. A domain I binding ErbB-2 binding antibody that has low intrinsic ADCC activity can be engineered to enhance the ADCC activity Fc regions mediate antibody function by binding to different receptors on immune effector cells such as macrophages, natural killer cells, B-cells and neutrophils. Some of these receptors, such as CD16A (FcγRIIIA) and CD32A (FcγRIIA), activate the cells to build a response against antigens. Other receptors, such as CD32B, inhibit the activation of immune cells. By engineering Fc regions (through introducing amino acid substitutions) that bind to activating receptors with greater selectivity, antibodies can be created that have greater capability to mediate cytotoxic activities desired by an anti-cancer Mab.

One technique for enhancing ADCC of an antibody is afucosylation. (See for instance Junttila, T. T., K. Parsons, et al. (2010). "Superior In vivo Efficacy of Afucosylated Trastuzumab in the Treatment of HER2-Amplified Breast Cancer." Cancer Research 70(11): 4481-4489). Further provided is therefore a bispecific antibody as disclosed herein, which is afucosylated. Alternatively, or additionally, multiple other strategies can be used to achieve ADCC enhancement, for instance including glycoengineering (Kyowa Hakko/Biowa, GlycArt (Roche) and Eureka Therapeutics) and mutagenesis (Xencor and Macrogenics), all of which seek to improve Fc binding to low-affinity activating FcγRIIIa, and/or to reduce binding to the low affinity inhibitory FcγRIIb.

Several in vitro methods exist for determining the efficacy of antibodies or effector cells in eliciting ADCC. Among these are chromium-51 [Cr51] release assays, europium [Eu] release assays, and sulfur-35 [S35] release assays. Usually, a labeled target cell line expressing a certain surface-exposed antigen is incubated with antibody specific for that antigen. After washing, effector cells expressing Fc receptor CD16 are typically co-incubated with the antibody-labeled target cells. Target cell lysis is subsequently typically measured by release of intracellular label, for instance by a scintillation counter or spectrophotometry.

In preferred bispecific antibodies, the affinity of said second antigen-binding site for an ErbB-3 positive cell is equal to, or preferably higher than, the affinity of said first antigen-binding site for an ErbB-2 positive cell. The affinity (KD) of said second antigen-binding site for an ErbB-3 positive cell is preferably lower than or equal to 2.0 nM, more preferably lower than or equal to 1.5 nM, more preferably lower than or equal to 1.39 nM, more preferably lower than or equal to 0.99 nM. In one preferred embodiment, the affinity of said second antigen-binding site for ErbB-3 on SK-BR-3 cells is lower than or equal to 2.0 nM, more preferably lower than or equal to 1.5 nM, more preferably lower than or equal to 1.39 nM, preferably lower than or equal to 0.99 nM. In one embodiment, said affinity is within the range of 1.39-0.59 nM. In one preferred embodiment, the affinity of said second antigen-binding site for ErbB-3 on BT-474 cells is lower than or equal to 2.0 nM, more preferably lower than or equal to 1.5 nM, more preferably lower than or equal to 1.0 nM, more preferably lower than 0.5 nM, more preferably lower than or equal to 0.31 nM, more preferably lower than or equal to 0.23 nM. In one embodiment, said affinity is within the range of 0.31-0.15 nM. The above-mentioned affinities are preferably as measured using steady state cell affinity measurements, wherein cells are incubated at 4° C. using radioactively labeled antibody, where after cell-bound radioactivity is measured, as described in the Examples of WO 2015/130173.

The affinity (KD) of said first antigen-binding site for an ErbB-2 positive cell is preferably lower than or equal to 5.0 nM, more preferably lower than or equal to 4.5 nM, more preferably lower than or equal to 3.9 nM. In one preferred embodiment, the affinity of said first antigen-binding site for ErbB-2 on SK-BR-3 cells is lower than or equal to 5.0 nM, preferably lower than or equal to 4.5 nM, more preferably lower than or equal to 4.0 nM, more preferably lower than or equal to 3.5 nM, more preferably lower than or equal to 3.0 nM, more preferably lower than or equal to 2.3 nM. In one embodiment, said affinity is within the range of 3.0-1.6 nM. In one preferred embodiment, the affinity of said first antigen-binding site for ErbB-2 on BT-474 cells is lower than or equal to 5.0 nM, preferably lower than or equal to 4.5 nM, more preferably lower than or equal to 3.9 nM. In one embodiment, said affinity is within the range of 4.5-3.3 nM. The above-mentioned affinities are preferably as measured using steady state cell affinity measurements, wherein cells are incubated at 4° C. using radioactively labeled antibody, where after cell-bound radioactivity is measured, as described in the Examples of WO 2015/130173.

Preferably, the bispecific antibodies used in the disclosed methods do not significantly affect the survival of cardiomyocytes. Cardiotoxicity is a known risk factor in ErbB-2 targeting therapies and the frequency of complications is increased when trastuzumab is used in conjunction with anthracyclines thereby inducing cardiac stress.

The bispecific antibodies disclosed herein are preferably used in humans. thus, preferred antibodies are human or humanized antibodies. Tolerance of a human to a polypeptide is governed by many different aspects. Immunity, be it T-cell mediated, B-cell mediated or other is one of the variables that are encompassed in tolerance of the human for a polypeptide. The constant region of a bispecific antibody is preferably a human constant region. The constant region may contain one or more, preferably not more than 10, preferably not more than 5 amino-acid differences with the constant region of a naturally occurring human antibody. It is preferred that the constant part is entirely derived from a naturally occurring human antibody. Various antibodies produced herein are derived from a human antibody variable domain library. As such these variable domains are human. The unique CDR regions may be derived from humans, be synthetic or derived from another organism. The variable region is considered a human variable region when it has an amino acid sequence that is identical to an amino acid sequence of the variable region of a naturally occurring human antibody, but for the CDR region. The variable region of an ErbB-2 binding VH, an ErbB-3 binding VH, or a light chain in an antibody may contain one or more, preferably not more than 10, preferably not more than 5 amino-acid differences with the variable region of a naturally occurring human antibody, not counting possible differences in the amino acid sequence of the CDR regions. Such mutations occur also in nature in the context of somatic hypermutation.

Antibodies may be derived from various animal species, at least with regard to the heavy chain variable region. It is common practice to humanize such e.g. murine heavy chain variable regions. There are various ways in which this can be achieved among which there are CDR-grafting into a human heavy chain variable region with a 3D-structure that matches the 3-D structure of the murine heavy chain variable region; deimmunization of the murine heavy chain variable region, preferably done by removing known or suspected T- or B-cell epitopes from the murine heavy chain variable region. The removal is typically by substituting one or more of the amino acids in the epitope for another (typically conservative) amino acid, such that the sequence of the epitope is modified such that it is no longer a T- or B-cell epitope.

Such deimmunized murine heavy chain variable regions are less immunogenic in humans than the original murine heavy chain variable region. Preferably a variable region or domain is further humanized, such as for instance veneered. By using veneering techniques, exterior residues which are readily encountered by the immune system are selectively replaced with human residues to provide a hybrid molecule that comprises either a weakly immunogenic or substantially non-immunogenic veneered surface. An animal as used in the invention is preferably a mammal, more preferably a primate, most preferably a human.

A bispecific antibody disclosed herein preferably comprises a constant region of a human antibody. According to differences in their heavy chain constant domains, antibodies are grouped into five classes, or isotypes: IgG, IgA, IgM, IgD, and IgE. These classes or isotypes comprise at least one of said heavy chains that is named with a corresponding Greek letter. Preferably the constant region comprises an IgG constant region, more preferably an IgG1 constant region, preferably a mutated IgG1 constant region. Some variation in the constant region of IgG1 occurs in nature, such as for instance the allotypes G1m1, 17 and G1m3, and/or is allowed without changing the immunological properties of the resulting antibody. Typically between about 1-10 amino acid insertions, deletions, substitutions or a combination thereof are allowed in the constant region.

Preferred bispecific antibodies as disclosed herein comprise:
at least the CDR3 sequence, preferably at least the CDR1, CDR2 and CDR3 sequences, or at least the heavy chain variable region sequence, of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898, or a heavy chain variable region sequence that differs in at most 15 amino acids, preferably in at most 1, 2, 3, 4, 5, 6, 7, 8, 9 or 10 amino acids, more preferably in at most 1, 2, 3, 4 or 5 amino acids, from the recited heavy chain variable region sequences; and/or
at least the CDR3 sequence, preferably at least the CDR1, CDR2 and CDR3 sequences, or at least the heavy chain variable region sequence, of an ErbB-3 specific heavy chain variable region selected from the group consisting of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 and MF6074, or a heavy chain variable region sequence that differs in at most 15 amino acids, preferably in at most 1, 2, 3, 4, 5, 6, 7, 8, 9 or 10 amino acids, more preferably in at most 1, 2, 3, 4 or 5 amino acids, from the recited heavy chain variable region sequences.

CDR sequences are for instance varied for optimization purposes, preferably in order to improve binding efficacy or the stability of the antibody. Optimization is for instance performed by mutagenesis procedures where after the stability and/or binding affinity of the resulting antibodies are preferably tested and an improved ErbB-2 or ErbB-3-specific CDR sequence is preferably selected. A skilled person is well capable of generating antibody variants comprising at least one altered CDR sequence. For instance, conservative amino acid substitution is applied. Examples of conservative amino acid substitution include the substitution of one hydrophobic residue such as isoleucine, valine, leucine or methionine for another hydrophobic residue, and the substitution of one polar residue for another polar residue, such as the substitution of arginine for lysine, glutamic acid for aspartic acid, or glutamine for asparagine.

Preferred antibodies comprise a variable domain that binds ErbB-2, wherein the VH chain of said variable domain comprises the amino acid sequence of VH chain MF2926; MF2930; MF1849; MF2973; MF3004; MF3958 (is humanized MF2971); MF2971; MF3025; MF2916; MF3991 (is humanized MF3004); MF3031; MF2889; MF2913; MF1847; MF3001, MF3003 or MF1898; or comprises the amino acid sequence of VH chain MF2926; MF2930; MF1849; MF2973; MF3004; MF3958 (is humanized MF2971); MF2971; MF3025; MF2916; MF3991 (is humanized MF3004); MF3031; MF2889; MF2913; MF1847; MF3001, MF3003 or MF1898 as having at most 15, preferably 1, 2, 3, 4, 5, 6, 7, 8, 9 or 10 more preferably at most 1, 2, 3, 4 or 5, amino acid insertions, deletions, substitutions or a combination thereof with respect to the above mentioned VH chain sequence. The VH chain of the variable domain that binds ErbB-2 preferably comprises the amino acid sequence of:
MF1849; or
MF2971 or a humanized version thereof, wherein said humanized version preferably comprises the amino acid sequence of MF3958; or
MF3004 or a humanized version thereof, wherein said humanized version preferably comprises the amino acid sequence of MF3991. In one embodiment, the VH chain of the variable domain that binds ErbB-2 comprises the amino acid sequence of VH chain MF1849; or MF2971 or a humanized version thereof, wherein said humanized version preferably comprises the amino acid sequence of MF3958; or MF3004 or a humanized version thereof, wherein said humanized version preferably comprises the amino acid sequence of MF3991, wherein the recited VH sequences have at most 15, preferably 1, 2, 3, 4, 5, 6, 7, 8, 9 or 10, more preferably at most 1, 2, 3, 4 or 5, amino acid insertions, deletions, substitutions or a combination thereof with respect to the respective sequence. In a preferred embodiment the VH chain of the variable domain that binds ErbB-2 comprises the amino acid sequence of MF3958; or comprises the amino acid sequence of MF3958 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VH chain sequence.

The VH chain of the variable domain that binds Erb-B3 preferably comprises the amino acid sequence of VH chain MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 or MF6074; or comprises the amino acid sequence of VH chain MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 or MF6074 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VH chain sequence. The VH chain of the variable domain that binds Erb-B3 preferably comprises the amino acid sequence of MF3178, MF3176, MF3163, MF6058, MF6061 or MF6065; or comprises the amino acid sequence of MF3178, MF3176, MF3163, MF6058, MF6061 or MF6065 having at most 15, preferably 1, 2, 3, 4, 5, 6, 7, 8, 9 or 10, more preferably in at most 1, 2, 3, 4 or 5, amino acid insertions, deletions, substitutions or a combination thereof with respect to the respective VH chain sequence. In a preferred embodiment the VH chain of the variable domain that binds ErbB-3 comprises the amino acid sequence of MF3178; or comprises the amino acid sequence of MF3178 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VH chain sequence. Preferably, the above-mentioned amino acid insertions, deletions and substitutions are not present in the CDR3 region. The above-mentioned amino acid insertions, deletions and substitutions are also preferably not present in the CDR1 and CDR2 regions. The above-mentioned amino acid insertions, deletions and substitutions are also preferably not present in the FR4 region.

Preferably, the antibody comprises at least the CDR1, CDR2 and CDR3 sequences of MF1849, MF2971, MF3958, MF3004 or MF3991, most preferably at least the CDR1, CDR2 and CDR3 sequences of MF3958. Said antibody preferably comprises at least the CDR1, CDR2 and CDR3 sequences of MF3178, MF3176, MF3163, MF6058, MF6061 or MF6065, most preferably at least the CDR1, CDR2 and CDR3 sequence of MF3178.

Preferably, the ErbB-2 specific heavy chain variable region comprises the amino acid sequence of the VH chain MF3958 having at most 15, preferably 1, 2, 3, 4, 5, 6, 7, 8, 9 or 10, more preferably at most 1, 2, 3, 4 or 5, amino acid insertions, deletions, substitutions or a combination thereof with respect said VH (preferably wherein said insertions, deletions, substitutions are not in CDR1, CDR2, or CDR3). Preferably, the ErbB-3 specific heavy chain variable region comprises the amino acid sequence of the VH chain MF3178 having at most 15, preferably 1, 2, 3, 4, 5, 6, 7, 8, 9 or 10, more preferably at most 1, 2, 3, 4 or 5, amino acid insertions, deletions, substitutions or a combination thereof with respect said VH. The one or more amino acid insertions, deletions, substitutions or a combination thereof are preferably not in the CDR1, CDR2 and CDR3 region of the VH chain. They are also preferably not present in the FR4 region. An amino acid substitution is preferably a conservative amino acid substitution.

Preferably, the ErbB-2 specific heavy chain variable region comprises the amino acid sequence of the VH chain MF3991 having at most 15, preferably 1, 2, 3, 4, 5, 6, 7, 8, 9 or 10, more preferably at most 1, 2, 3, 4 or 5, amino acid insertions, deletions, substitutions or a combination thereof with respect said VH (preferably wherein said insertions, deletions, substitutions are not in CDR1, CDR2, or CDR3). Preferably, the ErbB-3 specific heavy chain variable region comprises the amino acid sequence of the VH chain MF3178 having at most 15, preferably 1, 2, 3, 4, 5, 6, 7, 8, 9 or 10, more preferably at most 1, 2, 3, 4 or 5, amino acid insertions, deletions, substitutions or a combination thereof with respect said VH. The one or more amino acid insertions, deletions, substitutions or a combination thereof are preferably not in the CDR1, CDR2 and CDR3 region of the VH chain. They are also preferably not present in the FR4 region. An amino acid substitution is preferably a conservative amino acid substitution.

Preferably, the first antigen-binding site of the antibody comprises at least the CDR1, CDR2 and CDR3 sequences of MF3958, or CDR1, CDR2 and CDR3 sequences that differ in at most three, preferably in at most two, preferably in at most one amino acid from the CDR1, CDR2 and CDR3 sequences of MF3958, and wherein said second antigen-binding site comprises at least the CDR1, CDR2 and CDR3 sequence of MF3178, or CDR1, CDR2 and CDR3 sequences that differ in at most three, preferably in at most two, preferably in at most one amino acid from the CDR1, CDR2 and CDR3 sequences of MF3178.

Preferably, the bispecific antibody comprises i) a first antigen binding site comprising an ErbB-2 specific heavy chain variable region comprising the CDR1, CDR2, and CDR3 sequence of MF3958 and a light chain variable region and ii) a second antigen binding site comprising an ErbB-3 specific heavy chain variable region comprising the CDR1, CDR2, and CDR3 sequence of MF3178 and a light chain variable region.

Preferably, the ErbB-2 specific heavy chain variable region has the MF3958 sequence and the ErbB-3 specific heavy chain variable region has the MF3178 sequence. This combination is also referred to as the PB4188 antibody. Preferably, the PB4188 antibody is afucosylated.

Preferably, the bispecific antibody comprises the "heavy chain for erbB-2 binding" as depicted in the Sequence listing part 1D and the "heavy chain for erbB-3 binding" as depicted in the Sequence listing part 1D.

Preferably, the antigen binding sites of the bispecific antibody comprise a germline light chain 012, preferably the rearranged germline human kappa light chain IgVκ1-39*01/IGJκ1*01 or a fragment or a functional derivative thereof (nomenclature according to the IMGT database worldwide web at imgt.org). The terms rearranged germline human kappa light chain IgVκ1-39*01/IGJκ1*01, IGKV1-39/IGKJ1, huVκ1-39 light chain or in short huVκ1-39 are used. The light chain can have 1, 2, 3, 4 or 5 amino acid insertions, deletions, substitutions or a combination thereof. The mentioned 1, 2, 3, 4 or 5 amino acid substitutions are preferably conservative amino acid substitutions, the insertions, deletions, substitutions or a combination thereof are preferably not in the CDR3 region of the VL chain, preferably not in the CDR1, CDR2 or CDR3 region or FR4 region of the VL chain. Preferably, the first antigen binding site and the second antigen binding site comprise the same light chain variable region, or rather, a common light chain. Preferably, the light chain variable region comprises a CDR1 having the sequence (RASQSISSYLN; SEQ ID NO: 75), a CDR2 having the sequence (AASSLQS; SEQ ID NO: 76), and a CDR3 having the sequence (QQSYSTPPT; SEQ ID NO: 77). Preferably, the light chain variable region comprises the common light chain sequence depicted the Sequence listing part 1C.

Various methods are available to produce bispecific antibodies and are discussed in WO 2015/130173. One method involves the expression of two different heavy chains and two different light chains in a cell and collecting antibody that is produced by the cell. Antibody produced in this way will typically contain a collection of antibodies with different combinations of heavy and light chains, some of which are the desired bispecific antibody. The bispecific antibody can subsequently be purified from the collection.

The ratio of bispecific to other antibodies that are produced by the cell can be increased in various ways. Preferably, the ratio is increased by expressing not two different light chains but two essentially identical light chains in the cell. This concept is in the art also referred to as the "common light chain" method. When the essentially identically light chains work together with the two different heavy chains allowing the formation of variable domains with different antigen-binding sites and concomitant different binding properties, the ratio of bispecific antibody to other antibody that is produced by the cell is significantly improved over the expression of two different light chains. The ratio of bispecific antibody that is produced by the cell can be further improved by stimulating the pairing of two different heavy chains with each other over the pairing of two identical heavy chains. The art describes various ways in which such heterodimerization of heavy chains can be achieved. One way is to generate 'knob into hole' bispecific antibodies. See US Patent Application 20030078385 (Arathoon et al.—Genentech). Another and preferred method is described in PCT application No. PCT/NL2013/050294 (WO 2013/157954 A1), which are incorporated herein by reference. Methods and means are disclosed for producing bispecific antibodies from a single cell, whereby means are provided that favor the formation of bispecific antibodies over the formation of monospecific antibodies.

Sequences referred to in the disclosure are presented below and in FIG. 1.

Sequences 1A (erbB-2 Specific)

MF2926: heavy chain variable region sequence of an erbB-2 binding antibody Nucleic acid sequence (underlined sequence encodes end of leader peptide):

```
                                                               (SEQ ID NO: 1)
  1 GGCCCAGCCG GCCATGGCCC AGGTCCAGCT GCAGCAGTCT GGACCTGAGC TGGTGAAACC

61 TGGGGCTTCA GTGATGATTT CCTGCAAGGC TTCTGGTTAC TCATTCACTG GCTACCACAT

121 GAACTGGGTG AAGCAAAGTC CTGAAAAGAG CCTTGAGTGG ATTGGAGACA TAAATCCTAG

181 CATTGGTACG ACTGCCCACA ACCAGATTTT CAGGGCCAAG GCCACAATGA CTGTTGACAA

241 ATCCTCCAAC ACAGCCTACA TGCAGCTCAA GAGCCTGACA TCTGAAGACT CTGGAGTCTT

301 TTACTGTGTT AGAAGAGGGG ACTGGTCCTT CGATGTCTGG GGCACAGGGA CCACGGTCAC

361 CGTCTCCAGT
```

Amino Acid Sequence:

```
                                                               (SEQ ID NO: 2)
QVQLQQSGPELVKPGASVMISCKASGYSFTGYHMNWVKQSPEKSLEWIGD

INPSIGTTAHNQIFRAKATMTVDKSSNTAYMQLKSLTSEDSGVFYCVRRG

DWSFDVWGTGTTVTVSS (SEQ ID NO: 3)
CDR1: GYHMNWVKQSPEKSLE (SEQ ID NO: 4)
CDR2: NQIFRA (SEQ ID NO: 5)
CDR3: RGDWSFDV
```

MF2930: heavy chain variable region sequence of an erbB-2 binding antibody Nucleic acid sequence (underlined sequence encodes end of leader peptide):

```
                                                               (SEQ ID NO: 6)
  1 GGCCCAGCCG GCCATGGCCG AGGTCCAGCT GCAGCAGTCT GGGGCTGAAC TGGTGAAGCC

61 TGGAGCCTCA GTGATGATGT CCTGTAAGGT TTCTGGCTAC ACCTTCACTT CCTATCCTAT

121 AGCGTGGATG AAGCAGGTTC ATGGAAAGAG CCTAGAGTGG ATTGGAAATT TTCATCCTTA

181 CAGTGATGAT ACTAAGTACA ATGAAAACTT CAAGGGCAAG GCCACATTGA CTGTAGAAAA

241 ATCCTCTAGC ACAGTCTACT TGGAGCTCAG CCGATTAACA TCTGATGACT CTGCTGTTTA

301 TTACTGTGCA AGAAGTAACC CATTATATTA CTTTGCTATG GACTACTGGG GTCAAGGAAC

361 CTCGGTCACC GTCTCCAGT
```

Amino Acid Sequence:

(SEQ ID NO: 7)
EVQLQQSGAELVKPGASVMMSCKVSGYTFTSYPIAWMKQVHGKSLEWIGN

FHPYSDDTKYNENFKGKATLTVEKSSSTVYLELSRLTSDDSAVYYCARSN

PLYYFAMDYWGQGTSVTVSS (SEQ ID NO: 8)
CDR1: SYPIAWMKQVHGKSLE (SEQ ID NO: 9)
CDR2: NENFKG (SEQ ID NO: 10)
CDR3: SNPLYYFAMDY

MF1849: heavy chain variable region sequence of an erbB-2 binding antibody Nucleic acid sequence (underlined sequence encodes end of leader peptide):

(SEQ ID NO: 11)
```
  1 GGCCCAGCCG GCCATGGCCC AGGTGCAGCT GGTGGAGTCT GGGGGAGGCG TGGTCCAGCC

61 TGGGAGGTCC CTGAGACTCT CCTGTGCAGC CTCTGGATTC ACCTTCAGTA GCTATGGCAT

121 GCACTGGGTC CGCCAGGCTC CAGGCAAGGG GCTGGAGTGG GTGGCAGTTA TATCATATGA

181 TGGAAGTAAT AAATACTATG CAGACTCCGT GAAGGGCCGA TTCACCATCT CCAGAGACAA

241 TTCCAAGAAC ACGCTGTATC TGCAAATGAA CAGCCTGAGA GCTGAGGACA CGGCCGTGTA

301 TTACTGTGCA AAAGGTGACT ACGGTTCTTA CTCTTCTTAC GCCTTTGATT ATTGGGGCCA

361 AGGTACCCTG GTCACCGTCT CCAGT
```

Amino Acid Sequence:

(SEQ ID NO: 12)
QVQLVESGGGVVQPGRSLRLSCAASGFTFSSYGMHWVRQAPGKGLEWVAV

ISYDGSNKYYADSVKGRFTISRDNSKNTLYLQMNSLRAEDTAVYYCAKGD

YGSYSSYAFDYWGQGTLVTVSS (SEQ ID NO: 13)
CDR1: SYGMH (SEQ ID NO: 14)
CDR2: VISYDGSNKYYADSVKG (SEQ ID NO: 15)
CDR3: GDYGSYSSYAFDY

MF2973: heavy chain variable region sequence of an erbB-2 binding antibody Nucleic acid sequence (underlined sequence encodes end of leader peptide):

(SEQ ID NO: 16)
```
  1 GGCCCAGCCG GCCATGGCCC AGGTGCAGCT GAAGCAGTCT GGGGCTGAGC TGGTGAGGCC

61 TGGGGCTTCA GTGAAGTTGT CCTGCAAGGC TTCTGGCTAC ATTTTCACTG GCTACTATAT

121 AAACTGGTTG AGGCAGAGGC CTGGACAGGG ACTTGAATGG ATTGCAAAAA TTTATCCTGG

181 AAGTGGTAAT ACTTACTACA ATGAGAAGTT CAGGGGCAAG GCCACACTGA CTGCAGAAGA

241 ATCCTCCAGC ACTGCCTACA TGCAGCTCAG CAGCCTGACA TCTGAGGACT CTGCTGTCTA

301 TTTCTGTGCA AGAGGGCCCC ACTATGATTA CGACGGCCCC TGGTTTGTTT ACTGGGGCCA

361 AGGGACTCTG GTCACCGTCT CCAGT
```

Amino Acid Sequence:

(SEQ ID NO: 17)
QVQLKQSGAELVRPGASVKLSCKASGYIFTGYYINWLRQRPGQGLEWIAK

IYPGSGNTYYNEKFRGKATLTAEESSSTAYMQLSSLTSEDSAVYFCARGP

HYDYDGPWFVYWGQGTLVTVSS (SEQ ID NO: 18)
CDR1: GYYINWLRQRPGQGLE (SEQ ID NO: 19)
CDR2: NEKFRG (SEQ ID NO: 20)
CDR3: GPHYDYDGPWFVY

MF3004: heavy chain variable region sequence of an erbB-2 binding antibody Nucleic acid sequence (underlined sequence encodes end of leader peptide):

(SEQ ID NO: 21)
```
  1 GGCCCAGCCG GCCATGGCCC AGGTGCAGCT GAAGCAGTCT GGGGCTGAGC TGGTGAGGCC

61 TGGGGCTTCA GTGAAGCTGT CCTGCAAGGC TTCTGGCTAC ACTTTCACTG GCTACTATAT

121 AAACTGGGTG AAGCAGAGGC CTGGACAGGG ACTTGAGTGG ATTGCAAGGA TTTATCCTGG

181 AAGTGGTTAT ACTTACTACA ATGAGAAGTT CAAGGGCAAG GCCACACTGA CTGCAGAAGA

241 ATCCTCCAGC ACTGCCTACA TGCACCTCAG CAGCCTGACA TCTGAGGACT CTGCTGTCTA

301 TTTCTGTGCA AGACCCCACT ATGGTTACGA CGACTGGTAC TTCGGTGTCT GGGGCACAGG

361 CACCACGGTC ACCGTCTCCA GT
```

Amino Acid Sequence:

(SEQ ID NO: 22)
QVQLKQSGAELVRPGASVKLSCKASGYTFTGYYINWVKQRPGQGLEWIAR

IYPGSGYTYYNEKFKGKATLTAEESSSTAYMHLSSLTSEDSAVYFCARPH

YGYDDWYFGVWGTGTTVTVSS (SEQ ID NO: 23)
CDR1: GYYINWVKQRPGQGLE (SEQ ID NO: 24)
CDR2: NEKFKG (SEQ ID NO: 25)
CDR3: PHYGYDDWYFGV

MF2971: heavy chain variable region sequence of an erbB-2 binding antibody Nucleic acid sequence (underlined sequence encodes end of leader peptide):

(SEQ ID NO: 26)
```
  1 GGCCCAGCCG GCCATGGCCC AGGTGCAGCT GAAGCAGTCT GGGGCTGAGC TGGTGAGGCC

61 TGGGGCTTCA GTGAAACTGT CCTGCAAGGC TTCTGGCTAC ACTTTCACTG CCTACTATAT

121 AAACTGGGTG AAGCAGAGGC CTGGACAGGG ACTTGAGTGG ATTGCAAGGA TTTATCCTGG

181 AAGTGGCTAT ACTTACTACA ATGAGATTTT CAAGGGCAGG GCCACACTGA CTGCAGACGA

241 ATCCTCCAGC ACTGCCTACA TGCAACTCAG CAGCCTGACA TCTGAGGACT CTGCTGTCTA

301 TTTCTGTGCA AGACCTCCGG TCTACTATGA CTCGGCCTGG TTTGCTTACT GGGGCCAAGG

361 GACTCTGGTC ACCGTCTCCA GT
```

Amino Acid Sequence:

(SEQ ID NO: 139)
QVQLKQSGAELVRPGASVKLSCKASGYTFTAYYINWVKQRPGQGLEWIAR

IYPGSGYTYYNEIFKGRATLTADESSSTAYMQLSSLTSEDSAVYFCARPP

VYYDSAWFAYWGQGTLVTVSS (SEQ ID NO: 27)
CDR1: AYYINWVKQRPGQGLE (SEQ ID NO: 28)
CDR2: NEIFKG (SEQ ID NO: 29)
CDR3: PPVYYDSAWFAY

MF3025: heavy chain variable region sequence of an erbB-2 binding antibody Nucleic acid sequence (underlined sequence encodes end of leader peptide):

(SEQ ID NO: 30)
```
  1 GGCCCAGCCG GCCATGGCCC AGGTGCAGCT GAAGCAGTCT GGGGCTGAGC
    TGGTGAGGCC
 61 TGGGACTTCA GTGAAGCTGT CCTGCAAGGC TTCTGGCTAC ACTTTCACTG
    GCTACTATAT
121 AAACTGGGTG AAGCAGAGGC CTGGACAGGG ACTTGAGTGG ATTGCAAGGA
    TTTATCCTGG
181 AAGTGGTTAT ACTTACTACA ATGAGAAGTT CAAGGGCAAG GCCACACTGA
    CTGCAGAAGA
241 ATCCTCCAAC ACTGCCTATA TGCACCTCAG CAGCCTGACA TCTGAGGACT
    CTGCTGTCTA
301 TTTCTGTGCA AGGCCCCACT ATGGTTACGA CGACTGGTAC TTCGCTGTCT
    GGGGCACAGG
361 GACCACGGTC ACCGTCTCCA GT
```

Amino Acid Sequence:

(SEQ ID NO: 31)
QVQLKQSGAELVRPGTSVKLSCKASGYTFTGYYINWVKQRPGQGLEWIAR

IYPGSGYTYYNEKFKGKATLTAEESSNTAYMHLSSLTSEDSAVYFCARPH

YGYDDWYFAVWGTGTTVTVSS (SEQ ID NO: 32)
CDR1: GYYINWVKQRPGQGLE (SEQ ID NO: 33)
CDR2: NEKFKG (SEQ ID NO: 34)
CDR3: PHYGYDDWYFAV

MF2916: heavy chain variable region sequence of an erbB-2 binding antibody Nucleic acid sequence (underlined sequence encodes end of leader peptide):

(SEQ ID NO: 35)
```
  1 GGCCCAGCCG GCCATGGCCC AGGTCCAGCT GCAGCAGTCT GGGGCTGAGC
    TGGTGAGGCC
 61 TGGGGCTTCA GTGAAGCTGT CCTGCAAGGC TTCTGGCTAC ACTTTCACTG
    GCTACTATAT
121 AAACTGGGTG AAGCAGAGGC CTGGACAGGG ACTTGAGTGG ATTGCAAGGA
    TTTATCCTGG
181 CAGTGGTCAT ACTTCCTACA ATGAGAAGTT CAAGGGCAAG GCCACACTGA
    CTACAGAAAA
241 ATCCTCCAGC ACTGCCTACA TGCAGCTCAG CAGCCTGACA TCTGAGGACT
    CTGCTGTCTA
301 TTTCTGTGCA AGACCTATCT ACTTTGATTA CGCAGGGGGG TACTTCGATG
    TCTGGGGCAC
361 AAGAACCTCG GTCACCGTCT CCAGT
```

Amino Acid Sequence:

(SEQ ID NO: 36)
QVQLQQSGAELVRPGASVKLSCKASGYTFTGYYINWVKQRPGQGLEWIAR

IYPGSGHTSYNEKFKGKATLTTEKSSSTAYMQLSSLTSEDSAVYFCARPI

YFDYAGGYFDVVVGTRTSVTVSS (SEQ ID NO: 140)
CDR1: GYYINWVKQRPGQGLE (SEQ ID NO: 141)
CDR2: NEKFKG (SEQ ID NO: 37)
CDR3: PIYFDYAGGYFDV

MF3958: heavy chain variable region sequence of an erbB-2 binding antibody Nucleic acid sequence (underlined sequence encodes end of leader peptide):

(SEQ ID NO: 38)
```
  1 GGCCCAGCCG GCCATGGCCC AGGTGCAGCT GGTGCAGTCT GGCGCCGAAG
    TGAAGAAACC

61 TGGCGCCAGC GTGAAGCTGA GCTGCAAGGC CAGCGGCTAC ACCTTCACCG
    CCTACTACAT

121 CAACTGGGTC CGACAGGCCC CAGGCCAGGG CCTGGAATGG ATCGGCAGAA
    TCTACCCCGG

181 CTCCGGCTAC ACCAGCTACG CCCAGAAGTT CCAGGGCAGA GCCACCCTGA
    CCGCCGACGA

241 GAGCACCAGC ACCGCCTACA TGGAACTGAG CAGCCTGCGG AGCGAGGATA
    CCGCCGTGTA

301 CTTCTGCGCC AGACCCCCCG TGTACTACGA CAGCGCTTGG TTTGCCTACT
    GGGGCCAGGG

361 CACCCTGGTC ACCGTCTCCA GT
```

Amino Acid Sequence:

(SEQ ID NO: 39)
QVQLVQSGAEVKKPGASVKLSCKASGYTFTAYYINWVRQAPGQGLEWIGR

IYPGSGYTSYAQKFQGRATLTADESTSTAYMELSSLRSEDTAVYFCARPP

VYYDSAWFAYWGQGTLVTVSS (SEQ ID NO: 40)
CDR1: AYYIN (SEQ ID NO: 41)
CDR2: RIYPGSGYTSYAQKFQG (SEQ ID NO: 42)
CDR3: PPVYYDSAWFAY

MF3031: heavy chain variable region sequence of an erbB-2 binding antibody Nucleic acid sequence (underlined sequence encodes end of leader peptide):

(SEQ ID NO: 43)
```
  1 GGCCCAGCCG GCCATGGCCC AGGTCCAGCT GCAGCAGTCT GGGGCTGAGC
    TGGTGAGGCC

61 TGGGGCTTCA GTGAAGCTGT CCTGCAAGGC TTCTGGCTAC ACTTTCACTG
    CCTACTATAT

121 AAACTGGGTG AAGCAGAGGC CTGGACAGGG ACTTGAGTGG ATTGCAAAGA
    TTTATCCTGG

181 AAGTGGTTAT ACTTACTACA ATGAGAATTT CAGGGGCAAG GCCACACTGA
    CTGCAGAAGA

241 ATCCTCCAGT ACTGCCTACA TACAACTCAG CAGCCTGACA TCTGAGGACT
    CTGCTGTCTA

301 TTTCTGTGCA AGAGGCGTCT ATGATTACGA CGGGGCCTGG TTTGCTTACT
    GGGGCCAAGG

361 GACTCTGGTC ACCGTCTCCA GT
```

Amino Acid Sequence:

(SEQ ID NO: 142)
QVQLQQSGAELVRPGASVKLSCKASGYTFTAYYINWVKQRPGQGLEWIAK

IYPGSGYTYYNENFRGKATLTAEESSSTAYIQLSSLTSEDSAVYFCARGV

YDYDGAWFAYWGQGTLVTVSS (SEQ ID NO: 44)
CDR1: AYYINWVKQRPGQGLE (SEQ ID NO: 45)
CDR2: NENFRG (SEQ ID NO: 46)
CDR3: GVYDYDGAWFAY

MF3991: heavy chain variable region sequence of an erbB-2 binding antibody Nucleic acid sequence (underlined sequence encodes end of leader peptide):

(SEQ ID NO: 47)
```
  1 GGCCCAGCCG GCCATGGCCC AGGTGCAGCT GGTGCAGTCT GGCGCCGAAG
    TGAAGAAACC

61 TGGCGCCAGC GTGAAGCTGA GCTGCAAGGC CAGCGGCTAC ACCTTCACCG
    CCTACTACAT

121 CAACTGGGTC CGACAGGCCC CAGGCCAGGG CCTGGAATGG ATCGGCAGAA
    TCTACCCCGG

181 CTCCGGCTAC ACCAGCTACG CCCAGAAGTT CCAGGGCAGA GCCACCCTGA
    CCGCCGACGA

241 GAGCACCAGC ACCGCCTACA TGGAACTGAG CAGCCTGCGG AGCGAGGATA
    CCGCCGTGTA

301 CTTCTGCGCC AGACCCCACT ACGGCTACGA CGACTGGTAC TTCGGCGTGT
    GGGGCCAGGG

361 CACCCTGGTC ACCGTCTCCA GT
```

Amino Acid Sequence:

(SEQ ID NO: 48)
QVQLVQSGAEVKKPGASVKLSCKASGYTFTAYYINWVRQAPGQGLEWIGR

IYPGSGYTSYAQKFQGRATLTADESTSTAYMELSSLRSEDTAVYFCARPH

YGYDDWYFGVVVGQGTLVTVSS (SEQ ID NO: 49)
CDR1: AYYIN (SEQ ID NO: 50)
CDR2: RIYPGSGYTSYAQKFQG (SEQ ID NO: 51)
CDR3: PHYGYDDWYFGV

Sequences 1B (erbB-3 Specific)

MF3178: heavy chain variable region sequence of an erbB-3 binding antibody Nucleic acid sequence (underlined sequence encodes end of leader peptide):

(SEQ ID NO: 52)
```
  1 GGCCCAGCCG GCCATGGCCC AGGTGCAGCT GGTGCAGTCT GGGGCTGAGG
    TGAAGAAGCC

61 TGGGGCCTCA GTGAAGGTCT CCTGCAAGGC TTCTGGATAC ACCTTCACCG
    GCTACTATAT

121 GCACTGGGTG CGACAGGCCC CTGGACAAGG GCTTGAGTGG ATGGGATGGA
    TCAACCCTAA

181 CAGTGGTGGC ACAAACTATG CACAGAAGTT TCAGGGCAGG GTCACGATGA
    CCAGGGACAC

241 GTCCATCAGC ACAGCCTACA TGGAGCTGAG CAGGCTGAGA TCTGACGACA
    CGGCTGTGTA
```

-continued

```
301 TTACTGTGCA AGAGATCATG GTTCTCGTCA TTTCTGGTCT TACTGGGCT
    TTGATTATTG

361 GGGCCAAGGT ACCCTGGTCA CCGTCTCCAG T
```

Amino Acid Sequence:

(SEQ ID NO: 53)
QVQLVQSGAEVKKPGASVKVSCKASGYTFTGYYMHWVRQAPGQGLEWMGW

INPNSGGTNYAQKFQGRVTMTRDTSISTAYMELSRLRSDDTAVYYCARDH

GSRHFWSYWGFDYWGQGTLVTVSS (SEQ ID NO: 54)

CDR1: GYYMH (SEQ ID NO: 55)
CDR2: WINPNSGGTNYAQKFQG (SEQ ID NO: 56)
CDR3: DHGSRHFWSYWGFDY

MF3176: heavy chain variable region sequence of an erbB-3 binding antibody Nucleic acid sequence (underlined sequence encodes end of leader peptide):

(SEQ ID NO: 57)
```
  1 GGCCCAGCCG GCCATGGCCG AGGTGCAGCT GTTGGAGTCT GGGGGAGGCT
    TGGTACAGCC

61 TGGGGGGTCC CTGAGACTCT CCTGTGCAGC CTCTGGATTC ACCTTTAGCA
    GCTATGCCAT

121 GAGCTGGGTC CGCCAGGCTC CAGGGAAGGG GCTGGAGTGG GTCTCAGCTA
    TTAGTGGTAG

181 TGGTGGTAGC ACATACTACG CAGACTCCGT GAAGGGCCGG TTCACCATCT
    CCAGAGACAA

241 TTCCAAGAAC ACGCTGTATC TGCAAATGAA CAGCCTGAGA GCCGAGGACA
    CGGCTGTGTA

301 TTACTGTGCA AGAGATTGGT GGTACCCGCC GTACTACTGG GGCTTTGATT
    ATTGGGGCCA

361 AGGTACCCTG GTCACCGTCT CCAGT
```

Amino Acid Sequence:

(SEQ ID NO: 58)
EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCARDW

WYPPYYWGFDYWGQGTLVTVSS (SEQ ID NO: 59)
CDR1: SYAMS (SEQ ID NO: 60)
CDR2: AISGSGGSTYYADSVKG (SEQ ID NO: 61)
CDR3: DWWYPPYYWGFDY

MF3163: heavy chain variable region sequence of an erbB-3 binding antibody Nucleic acid sequence (underlined sequence encodes end of leader peptide):

(SEQ ID NO: 62)
```
  1 GGCCCAGCCG GCCATGGCCC AGGTGCAGCT GGTGCAGTCT GGGGCTGAGG TGAAGAAGCC

61 TGGGGCCTCA GTGAAGGTCT CCTGCAAGGC TTCTGGATAC ACCTTCACCG GCTACTATAT

121 GCACTGGGTG CGACAGGCCC CTGGACAAGG GCTTGAGTGG ATGGGATGGA TCAACCCTAA

181 CAGTGGTGGC ACAAACTATG CACAGAAGTT TCAGGGCAGG GTCACGATGA CCAGGGACAC
```

-continued

```
241 GTCCATCAGC ACAGCCTACA TGGAGCTGAG CAGGCTGAGA TCTGACGACA CGGCCGTGTA

301 TTACTGTGCA AAAGATTCTT ACTCTCGTCA TTTCTACTCT TGGTGGGCCT TTGATTATTG

361 GGGCCAAGGT ACCCTGGTCA CCGTCTCCAG T
```

Amino Acid Sequence:

(SEQ ID NO: 143)
QVQLVQSGAEVKKPGASVKVSCKASGYTFTGYYMHWVRQAPGQGLEWMGW

INPNSGGTNYAQKFQGRVTMTRDTSISTAYMELSRLRSDDTAVYYCAKDS

YSRHFYSWWAFDYWGQGTLVTVSS

-continued (SEQ ID NO: 144)
CDR1: GYYMH (SEQ ID NO: 63)
CDR2: WINPNSGGTNYAQKFQG (SEQ ID NO: 64)
CDR3: DSYSRHFYSWWAFDY MF3099: heavy chain variable region sequence of an erbB-3 binding antibody Nucleic acid sequence (underlined sequence encodes end of leader peptide):

(SEQ ID NO: 65)
```
1   GGCCCAGCCG GCCATGGCCG AGGTCCAGCT GCAGCAGCCT GGGGCTGAGC TGGTGAGGCC

61  TGGGACTTCA GTGAAGTTGT CCTGCAAGGC TTCTGGCTAC ACCTTCACCA GCTACTGGAT

121 GCACTGGGTA AAGCAGAGGC CTGGACAAGG CCTTGAGTGG ATCGGAATTC TTGATCCTTC

181 TGATAGTTAT ACTACCTACA ATCAAAAGTT CAAGGGCAAG GCCACATTAA CAGTAGACAC

241 ATCCTCCAGC ATAGCCTACA TGCAGCTCAG CAGCCTGACA TCTGAGGACT CTGCGCTCTA

301 TTACTGTGCA AGAGGGGGAG ATTACGACGA GGGAGGTGCT ATGGACTACT GGGGTCAAGG

361 AACCTCGGTC ACCGTCTCCA GT
```

Amino Acid Sequence:

(SEQ ID NO: 66)
EVQLQQPGAELVRPGTSVKLSCKASGYTFTSYWMHWVKQRPGQGLEWIGI

LDPSDSYTTYNQKFKGKATLTVDTSSSIAYMQLSSLTSEDSALYYCARGG

DYDEGGAMDYWGQGTSVTVSS (SEQ ID NO: 67)
CDR1: SYWMH (SEQ ID NO: 68)
CDR2: ILDPSDSYTTYNQKFKG (SEQ ID NO: 69)
CDR3: GGDYDEGGAMDY

MF3307: heavy chain variable region sequence of an erbB-3 binding antibody Nucleic acid sequence (underlined sequence encodes end of leader peptide):

(SEQ ID NO: 70)
```
1   GGCCCAGCCG GCCATGGCCC AGGTGCAGCT GGTGCAGTCT GGGGCTGAGG TGAAGAAGCC

61  TGGGGCCTCA GTGAAGGTCT CCTGCAAGGC TTCTGGATAC ACCTTCACCG GCTACTATAT

121 GCACTGGGTG CGACAGGCCC CTGGACAAGG GCTTGAGTGG ATGGGATGGA TCAACCCTAA

181 CAGTGGTGGC ACAAACTATG CACAGAAGTT TCAGGGCAGG GTCACGATGA CCAGGGACAC

241 GTCCATCAGC ACAGCCTACA TGGAGCTGAG CAGGCTGAGA TCTGACGACA CGGCCGTGTA

301 TTACTGTGCA AGAGGTTCTC GTAAACGTCT GTCTAACTAC TTCAACGCCT TTGATTATTG

361 GGGCCAAGGT ACCCTGGTCA CCGTCTCCAG T
```

Amino Acid Sequence:

(SEQ ID NO: 71)
QVQLVQSGAEVKKPGASVKVSCKASGYTFTGYYMHWVRQAPGQGLEWMGW
INPNSGGTNYAQKFQGRVTMTRDTSISTAYMELSRLRSDDTAVYYCARGS
RKRLSNYFNAFDYWGQGTLVTVSS

CDR1: GYYMH (SEQ ID NO: 145)

CDR2: WINPNSGGTNYAQKFQG (SEQ ID NO: 72)

CDR3: GSRKRLSNYFNAFDY (SEQ ID NO: 73)

Sequences 1C
Common Light Chain
  The variable region of IGKV1-39A (SEQ ID NO: 74)
DIQMTQSPSSLSASVGDRVTITCRASQSISSYLNWYQQKPGKAPKLLIYA
ASSLQSGVPSRFSGSGSGTDFTLTISSLQPEDFATYYCQQSYSTP

CDR 1: RASQSISSYLN (SEQ ID NO: 75)

CDR 2: AASSLQS (SEQ ID NO: 76)

CDR 3: QQSYSTPPT (SEQ ID NO: 77)

IGKV1-39/jk1

(SEQ ID NO: 78)
DIQMTQSPSSLSASVGDRVTITCRASQSISSYLNWYQQKPGKAPKLLIYA
ASSLQSGVPSRFSGSGSGTDFTLTISSLQPEDFATYYCQQSYSTPPITFG
QGTRLEIK

Common light chain IGKV1-39/jk1 (constant region is underlined)

(SEQ ID NO: 79)
DIQMTQSPSSLSASVGDRVTITCRASQSISSYLNWYQQKPGKAPKLLIYA
ASSLQSGVPSRFSGSGSGTDFTLTISSLQPEDFATYYCQQSYSTPPTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

IGKV1-39/jk5 common light chain variable domain (SEQ ID NO: 80)
DIQMTQSPSSLSASVGDRVTITCRASQSISSYLNWYQQKPGKAPKLLIYA
ASSLQSGVPSRFSGSGSGTDFTLTISSLQPEDFATYYCQQSYSTPPTFGQ
GTKVEIK Sequences 1D (erbB-2 Specific)
  heavy chain for erbB-2 binding (SEQ ID NO: 81)
QVQLVQSGAEVKKPGASVKLSCKASGYTFTAYYINWVRQAPGQGLEWIGR
IYPGSGYTSYAQKFQGRATLTADESTSTAYMELSSLRSEDTAVYFCARPP
VYYDSAWFAYWGQGTLVTVSSASTKGPSVFPLAPSSKSTSGGTAALGCLV
KDYFPEPVTVSWNSGALTSGVHTFPAVLQSSGLYSLSSVVTVPSSSLGTQ
TYICNVNHKPSNTKVDKRVEPKSCDKTHTCPPCPAPELLGGPSVFLFPPK
PKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREP
QVYTDPPSREEMTKNQVSLTCEVKGFYPSDIAVEWESNGQPENNYKTTPP
VLDSDGSFFLYSKLTVDKSRWQQGNVFSCSVMHEALHNHYTQKSLSLSPG heavy chain for erbB-3 binding (SEQ ID NO: 82)
QVQLVQSGAEVKKPGASVKVSCKASGYTFTGYYMHWVRQAPGQGLEWMGW
INPNSGGTNYAQKFQGRVTMTRDTSISTAYMELSRLRSDDTAVYYCARDH
GSRHFWSYWGFDYWGQGTLVTVSSASTKGPSVFPLAPSSKSTSGGTAALG
CLVKDYFPEPVTVSWNSGALTSGVHTFPAVLQSSGLYSLSSVVTVPSSSL
GTQTYICNVNHKPSNTKVDKRVEPKSCDKTHTCPPCPAPELLGGPSVFLF
PPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQP
REPQVYTKPPSREEMTKNQVSLKCLVKGFYPSDIAVEWESNGQPENNYKT
TPPVLDSDGSFFLYSKLTVDKSRWQQGNVFSCSVMHEALHNHYTQKSLSL
SPG Sequences 1E
HER2-Specific Ab Sequences
  MF2889: heavy chain variable region sequence of an erbB-2 binding antibody Nucleic acid sequence (underlined sequence encodes end of leader peptide):

(SEQ ID NO: 83)
  1 GGCCCAGCCG GCCATGGCCG AGGTCCAGCT GCAGCAGTCT GGAGCTGAGC TGGTAAGGCC
 61 TGGGACTTCA GTGAAGGTGT CCTGCAAGGC TTCTGGATAC GCCTTCACTA ATTATTTGAT
121 AGAGTGGGTA AAGCAGAGGC CTGGCCAGGG CCTTGAGTGG ATTGGAGTGA TTTATCCTGA
181 AGGTGGTGGT ACTATCTACA ATGAGAAGTT CAAGGGCAAG GCAACACTGA CTGCAGACAA

```
241 ATCCTCCAGC ACTGCCTACA TGCAGCTCAG CGGCCTGACA TCTGAGGACT CTGCGGTCTA

301 TTTCTGTGCA AGAGGAGACT ATGATTACAA ATATGCTATG GACTACTGGG GTCAAGGAAC

361 CTCGGTCACC GTCTCCAGT
```

Amino Acid Sequence:

(SEQ ID NO: 84)
```
EVQLQQSGAELVRPGTSVKVSCKASGYAFTNYLIEWVKQRPGQGLEWIGV

IYPEGGGTIYNEKFKGKATLTADKSSSTAYMQLSGLTSEDSAVYFCARGD

YDYKYAMDYWGQGTSVTVSS
```

(SEQ ID NO: 85)
CDR1: NYLIE (SEQ ID NO: 86)
CDR2: VIYPEGGGTIYNEKFKG (SEQ ID NO: 87)
CDR3: GDYDYKYAMDY

MF2913: heavy chain variable region sequence of an erbB-2 binding antibody Nucleic acid sequence (underlined sequence encodes end of leader peptide):

(SEQ ID NO: 88)
```
  1 GGCCCAGCCG GCCATGGCCG AGGTCAAGCT GCAGCAGTCT GGACCTGAGC TGGTGAAGCC

61 TGGCGCTTCA GTGAAGATAT CCTGCAAGGC TTCTGGTTAC TCATTCACTG ACTACAAAAT

121 GGACTGGGTG AAGCAGAGCC ATGGAAAGAG CCTCGAATGG ATTGGAAATA TTAATCCTAA

181 CAGTGGTGGT GTTATCTACA ACCAGAAGTT CAGGGGCAAG GTCACATTGA CTGTTGACAG

241 GTCCTCCAGC GCAGCCTACA TGGAGCTCCG CAGCCTGACA TCTGAGGACA CTGCAGTCTA

301 TTATTGTTCA AGAGGACTGT GGGATGCTAT GGACTCCTGG GGTCAAGGAA CCTCGGTCAC

361 CGTCTCCAGT
```

Amino Acid Sequence:

(SEQ ID NO: 89)
```
EVKLQQSGPELVKPGASVKISCKASGYSFTDYKMDWVKQSHGKSLEWIGN

INPNSGGVIYNQKFRGKVTLTVDRSSSAAYMELRSLTSEDTAVYYCSRGL

WDAMDSWGQGTSVTVSS
```

(SEQ ID NO: 90)
CDR1: DYKMDWVKQSHGKSLE (SEQ ID NO: 91)
CDR2: NQKFRG (SEQ ID NO: 92)
CDR3: GLWDAMDS

MF1847: heavy chain variable region sequence of an erbB-2 binding antibody Nucleic acid sequence (underlined sequence encodes end of leader peptide):

(SEQ ID NO: 93)
```
  1 GGCCCAGCCG GCCATGGCCC AGGTGCAGCT GGTGGAGTCT GGGGGAGGCG TGGTCCAGCC

61 TGGGAGGTCC CTGAGACTCT CCTGTGCAGC CTCTGGATTC ACCTTCAGTA GCTATGGCAT

121 GCACTGGGTC CGCCAGGCTC CAGGCAAGGG GCTGGAGTGG GTGGCAGTTA TATCATATGA

181 TGGAAGTAAT AAATACTATG CAGACTCCGT GAAGGGCCGA TTCACCATCT CCAGAGACAA

241 TTCCAAGAAC ACGCTGTATC TGCAAATGAA CAGCCTGAGA GCTGAGGACA CGGCCGTGTA

301 TTACTGTGCA AAAGGTTGGT GGCATCCGCT GCTGTCTGGC TTTGATTATT GGGGCCAAGG

361 TACCCTGGTC ACCGTCTCCA GT
```

Amino Acid Sequence:

(SEQ ID NO: 94)
QVQLVESGGGVVQPGRSLRLSCAASGFTFSSYGMHWVRQAPGKGLEWVAV

ISYDGSNKYYADSVKGRFTISRDNSKNTLYLQMNSLRAEDTAVYYCAKGW

WHPLLSGFDYWGQGTLVTVSS (SEQ ID NO: 95)
CDR1: SYGMH (SEQ ID NO: 96)
CDR2: VISYDGSNKYYADSVKG (SEQ ID NO: 97)
CDR3: GWWHPLLSGFDY

MF3001: heavy chain variable region sequence of an erbB-2 binding antibody Nucleic acid sequence (underlined sequence encodes end of leader peptide):

(SEQ ID NO: 98)
```
  1 GGCCCAGCCG GCCATGGCCG AGGTCCAGCT GCAGCAGTCT GGGGCTGAAC TGGCAAAACC

61 TGGGGCCTCA GTGAAGCTGT CCTGCAAGAC TTCTGGCTAC AACTTTCCTA TCTACTGGAT

121 GCACTGGGTA AAACAGAGGC CTGGACGGGG TCTGGAATGG ATTGGATACA TTAATCCTAG

181 TACTGGTTAT ATTAAGAACA ATCAGAAGTT CAAGGACAAG GCCACCTTGA CTGCAGACAA

241 ATCCTCCAAC ACAGCCTACA TGCAGCTGAA CAGCCTGACA TATGAGGACT CTGCAGTCTA

301 TTACTGTACA AGAGAAGGGA TAACTGGGTT TACTTACTGG GGCCAAGGGA CTCTGGTCAC

361 CGTCTCCAGT
```

Amino Acid Sequence:

(SEQ ID NO: 99)
EVQLQQSGAELAKPGASVKLSCKTSGYNFPIYWMHWVKQRPGRGLEWIGY

INPSTGYIKNNQKFKDKATLTADKSSNTAYMQLNSLTYEDSAVYYCTREG

ITGFTYWGQGTLVTVSS (SEQ ID NO: 100)
CDR1: IYWMHWVKQRPGRGLE (SEQ ID NO: 101)
CDR2: NQKFKD (SEQ ID NO: 102)
CDR3: EGITGFTY

MF1898: heavy chain variable region sequence of an erbB-2 binding antibody Nucleic acid sequence (underlined sequence encodes end of leader peptide):

(SEQ ID NO: 103)
```
  1 GGCCCAGCCG GCCATGGCCC AGGTGCAGCT GGTGGAGTCT GGGGGAGGCG TGGTCCAGCC

61 TGGGAGGTCC CTGAGACTCT CCTGTGCAGC CTCTGGATTC ACCTTCAGTA GCTATGGCAT

121 GCACTGGGTC CGCCAGGCTC CAGGCAAGGG GCTGGAGTGG GTGGCAGTTA TATCATATGA

181 TGGAAGTAAT AAATACTATG CAGACTCCGT GAAGGGCCGA TTCACCATCT CCAGAGACAA

241 TTCCAAGAAC ACGCTGTATC TGCAAATGAA CAGCCTGAGA GCTGAGGACA CGGCCGTGTA

301 TTACTGTGCA AAAGATGGTT CCGTCGTAC TACTCTGTCT GGCTTTGATT ATTGGGGCCA

361 AGGTACCCTG GTCACCGTCT CCAGT
```

Amino Acid Sequence:

(SEQ ID NO: 104)
QVQLVESGGGVVQPGRSLRLSCAASGFTFSSYGMHWVRQAPGKGLEWVAV

ISYDGSNKYYADSVKGRFTISRDNSKNTLYLQMNSLRAEDTAVYYCAKDG

FRRTTLSGFDYWGQ GTLVTVSS (SEQ ID NO: 146)
CDR1: SYGMH (SEQ ID NO: 147)
CDR2: VISYDGSNKYYADSVKG (SEQ ID NO: 105)
CDR3: DGFRRTTLSGFDY

MF3003 heavy chain variable region sequence of an erbB-2 binding antibody Nucleic acid sequence (underlined sequence encodes end of leader peptide):

(SEQ ID NO: 106)
```
  1 GGCCCAGCCG GCCATGGCCC AGGTGCAGCT GAAGCAGTCT GGACCTGAGC TGGTGAAGCC

61 TGGGGCCTCA GTGAAGATTT CCTGCAAGGC TTCTGGCGAC GCATTCAGTT ACTCCTGGAT

121 GAACTGGGTG AAGCAGAGGC CTGGAAAGGG TCTTGAGTGG ATTGGACGGA TTTATCCTGG

181 AGATGGAGAT ATTAACTACA ATGGGAAGTT CAAGGGCAAG GCCACACTGA CTGCAGACAA

241 ATCCTCCAGC ACAGCCCACC TGCAACTCAA CAGCCTGACA TCTGAGGACT CTGCGGTCTA

301 CTTCTGTGCA AGAGGACAGC TCGGACTAGA GGCCTGGTTT GCTTATTGGG GCCAGGGGAC

361 TCTGGTCACC GTCTCCAGT
```

Amino Acid Sequence:

(SEQ ID NO: 107)
QVQLKQSGPELVKPGASVKISCKASGDAFSYSWMNWVKQRPGKGLEWIGR

IYPGDGDINYNGKFKGKATLTADKSSSTAHLQLNSLTSEDSAVYFCARGQ

LGLEAWFAYWGQGTLVTVSS (SEQ ID NO: 108)
CDR1: YSWMNWVKQRPGKGLE (SEQ ID NO: 109)
CDR2: NGKFKG (SEQ ID NO: 110)
CDR3: GQLGLEAWFAY

HER3-Specific Ab Sequences
MF6058: heavy chain variable region sequence of an erbB-3 binding antibody Nucleic acid sequence (underlined sequence encodes end of leader peptide):

(SEQ ID NO: 111)
```
  1 GGCCCAGCCG GCCATGGCCC AGGTGCAGCT GGTGCAGTCT GGGGCTGACG TGAAGAAGCC

61 TGGGGCCTCA GTGAAGGTCA CGTGCAAGGC TTCTGGATAC ACCTTCACCG GCTACTATAT

121 GCACTGGGTG CGACAGGCCC CTGGACAAGC TCTTGAGTGG ATGGGATGGA TCAACCCTCA

181 AAGTGGTGGC ACAAACTATG CAAAGAAGTT TCAGGGCAGG GTCTCTATGA CCAGGGAGAC

241 GTCCACAAGC ACAGCCTACA TGCAGCTGAG CAGGCTGAGA TCTGACGACA CGGCTACGTA

301 TTACTGTGCA AGAGATCATG GTTCTCGTCA TTTCTGGTCT TACTGGGGCT TGATTATTG

361 GGGCCAAGGT ACCCTGGTCA CCGTCTCCAG T
```

Amino Acid Sequence:

(SEQ ID NO: 112)
QVQLVQSGADVKKPGASVKVTCKASGYTFTGYYMHWVRQAPGQALEWMGW

INPQSGGTNYAKKFQGRVSMTRETSTSTAYMQLSRLRSDDTATYYCARDH

GSRHFWSYWGFDYWGQGTLVTVSS (SEQ ID NO: 148)
CDR1: GYYMH (SEQ ID NO: 113)
CDR2: WINPQSGGTNYAKKFQG (SEQ ID NO: 114)
CDR3: DHGSRHFWSYWGFDY

MF6061: heavy chain variable region sequence of an erbB-3 binding antibody Nucleic acid sequence (underlined sequence encodes end of leader peptide):

(SEQ ID NO: 115)
```
  1 GGCCCAGCCG GCCATGGCCC AGGTGCAGCT GGTGCAGTCT GGGGCTGAGG TGAAGAAGCC

61 TGGGGCCTCA GTGAAGGTCT CCTGCAAGGC TTCTGGATAC ACCTTCACCG GCTACTATAT

121 GCACTGGGTG CGACAGGCCC CTGGACAAGG CTTGAGTGG ATGGGATGGA TCAACCCTCA

181 GAGTGGTGGC ACAAACTATG CACAGAAGTT TAAGGGCAGG GTCACGATGA CCAGGGACAC

241 GTCCACCAGC ACAGCCTACA TGGAGCTGAG CAGGCTGAGA TCTGACGACA CGGCTGTGTA

301 TTACTGTGCA AGAGATCATG GTTCTCGTCA TTTCTGGTCT TACTGGGGCT TTGATTATTG

361 GGGCCAAGGT ACCCTGGTCA CCGTCTCCAG T
```

Amino Acid Sequence:

(SEQ ID NO: 116)
QVQLVQSGAEVKKPGASVKVSCKASGYTFTGYYMHWVRQAPGQGLEWMGW

INPQSGGTNYAQKFKGRVTMTRDTSTSTAYMELSRLRSDDTAVYYCARDH

GSRHFWSYWGFDYWGQGTLVTVSS (SEQ ID NO: 149)
CDR1: GYYMH (SEQ ID NO: 117)
CDR2: WINPQSGGTNYAQKFKG (SEQ ID NO: 150)
CDR3: DHGSRHFWSYWGFDY

MF6065: heavy chain variable region sequence of an erbB-3 binding antibody Nucleic acid sequence (underlined sequence encodes end of leader peptide):

(SEQ ID NO: 118)
```
  1 GGCCCAGCCG GCCATGGCCC AGGTGCAGCT GGTGCAGTCT GGGGCTGAGG TGAAGAAGCC

61 TGGGGCCTCA GTGAAGGTCT CCTGCAAGGC TTCTGGATAC ACCTTCACCT CTTACTATAT

121 GCACTGGGTG CGACAGGCCC CTGGACAAGG CTTGAGTGG ATGGGATGGA TCAACCCTCA

181 GGGGGGTTCT ACAAACTATG CACAGAAGTT TCAGGGCAGG GTCACGATGA CCAGGGACAC

241 GTCCACCAGC ACAGTGTACA TGGAGCTGAG CAGGCTGAGA TCTGAGGACA CGGCTGTGTA

301 TTACTGTGCA AGAGATCATG GTTCTCGTCA TTTCTGGTCT TACTGGGGCT TTGATTATTG

361 GGGCCAAGGT ACCCTGGTCA CCGTCTCCAG T
```

Amino Acid Sequence:

```
                                              (SEQ ID NO: 119)
QVQLVQSGAEVKKPGASVKVSCKASGYTFTSYYMHWVRQAPGQGLEWMGW

INPQGGSTNYAQKFQGRVTMTRDTSTSTVYMELSRLRSEDTAVYYCARDH

GSRHFWSYWGFDYWGQGTLVTVSS (SEQ ID NO: 120)
CDR1: SYYMH (SEQ ID NO: 121)
CDR2: WINPQGGSTNYAQKFQG (SEQ ID NO: 151)
CDR3: DHGSRHFWSYWGFDY
```

For the purpose of clarity and a concise description features are described herein as part of the same or separate embodiments, however, it will be appreciated that the scope of the invention may include embodiments having combinations of all or some of the features described.

BRIEF DESCRIPTION OF THE DRAWINGS

Figure 1:
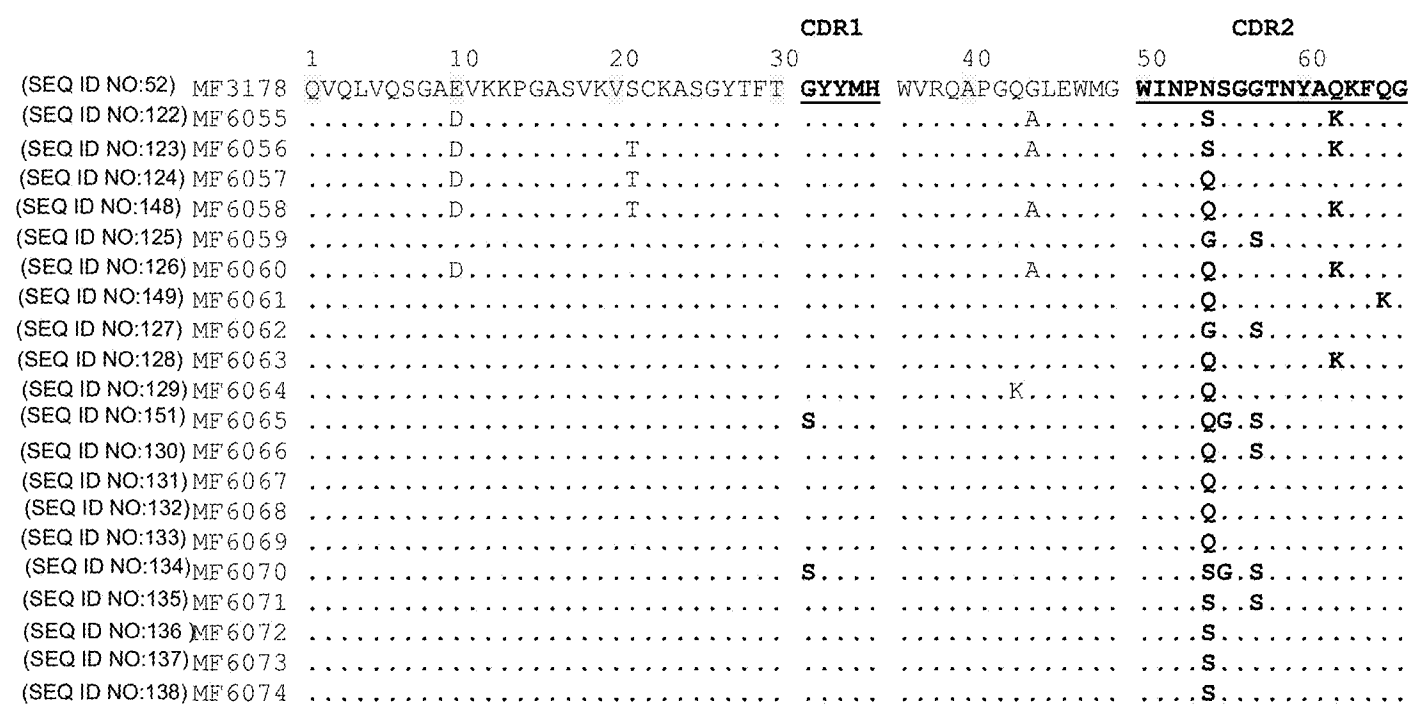

FIG. 1: Amino acid alignment of MF3178 variants. Dots indicate the same amino acid as in MF3178 at that position. The CDR1, CDR2 and CDR3 sequences of MF3178 are in bold and underlined.

The DOC4-NRG1 and CLU-NRG1 gene fusions are expressed in the MDA-MB-175 cell line (breast) and in the OV-10-0050 PDX (ovarian), respectively. Left panel: in vitro MCLA-128 treatment inhibits MDA-MB-175 cell proliferation. Right panel: In vivo, MCLA-128 treatment (25 mg/kg weekly until day 28) reduced tumor growth and eliminated tumors in 6/8 animals.

EXAMPLES

Example 1: ErbB-2-Guided Targeting

An imaging experiment was performed comparing the HER2×HER3 bispecific antibody (PB4188) to the HER3 bivalent monoclonal antibody. Variants of bAb PB4188 and anti-HER3 MF3178 (parental antibody) were labelled with 64Cu and injected intravenously in mouse xenografted with HER2 gene-amplified JIMT-1 tumors. Micro-PET imaging demonstrated that the PB4188 variant more effectively accumulated in tumors compared to the HER3 monoclonal (FIG. 2A).

Figure 2B:
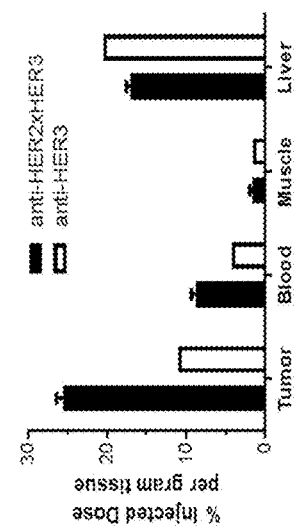
FIG. 2B: Gamma-counter quantification of radioactivity present in tumors confirmed that levels of PB4188 variant in the tumors were 2.5-fold higher than for the parental anti-HER3 antibody.
Figure 2A:
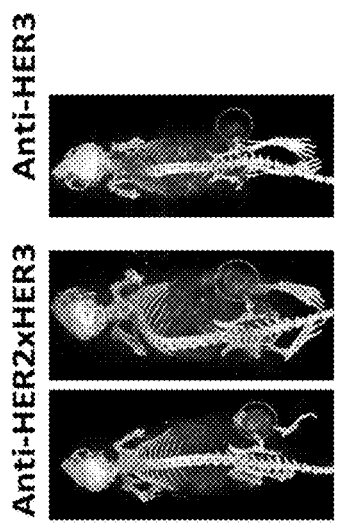
FIG. 2A: Increased in vivo tumor-targeting of bispecific over monoclonal antibody. Micro-PET imaging demonstrates that the PB4188 variant more effectively accumulates in tumors compared to the HER3 monoclonal.
Figure 2C:
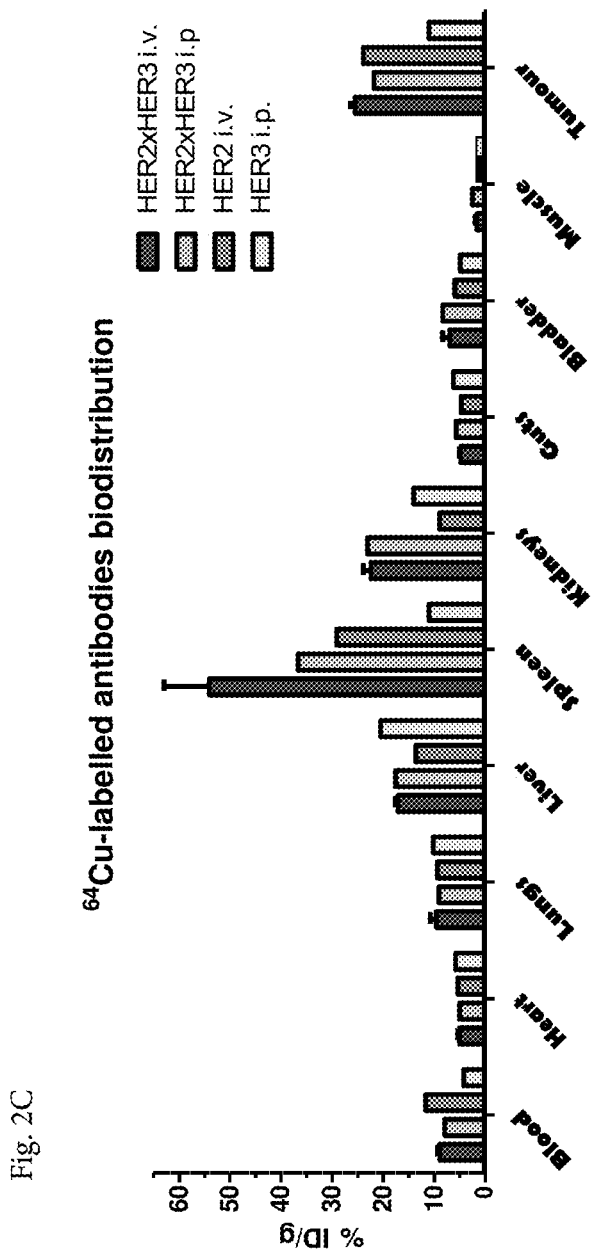
FIG. 2C: Quantitative biodistribution for tumour uptake in the 4 mAb groups at 48 hrs. Results are expressed as a percentage of the injected dose per gram of tissue (% ID/g), error bars indicate ±S.

Gamma-counter quantification of radioactivity present in tumors confirmed that levels of PB4188 variant in the tumors were 2.5-fold higher than for the parental anti-HER3 antibody (FIG. 2B). Overall, in vitro and in vivo data demonstrate that HER2-targeting is responsible for enhanced binding of PB4188 on tumor cells. Additional studies were performed using an anti-HER2 (MF3958) antibody. FIG. 2C summarizes the results of the respective antibodies labelled with 64Cu and injected in mouse xenografted with HER2 gene-amplified JIMT-1 tumors (n=4 mice for each antibody treatment).

Methods

Biodistribution study. Variants of bAb PB4188, anti-HER2 MF3958, and anti-HER3 MF3178 were conjugated to a bifunctional chelator [Paterson 2014 Dalton Transactions]. Binding characteristics of the conjugated products to the target were confirmed using flow cytometry-based assays. Proteins were then labelled with 64Cu and mice bearing JIMT-1 breast xenografts were administered the radiolabeled antibodies via tail vein (FIGS. 2A-B and "i.v." for FIG. 2C) or intraperitoneal ("i.p." for FIG. 2C). MicroPET/CT images were acquired 48 hrs post-injection, after which tumor were excised and radioactivity was measured in a gamma counter. Results were expressed as percentage injected dose per gram tissue.

Example 2 Inhibition of Heterodimer Formation

Heterodimerization assays based on the enzyme fragment complementation technology were used. The δ-galactosidase enzyme can be artificially split into two inactive fragments, the enzyme donor and the enzyme acceptor, which combine into an active enzyme only when in close proximity. Each sequence encoding either the enzyme donor or the enzyme acceptor is linked to the extracellular and transmembrane domains of each heterodimerization partner. Both genes are then co-transfected in U2OS cells to express extracellular domains of RTK receptors linked to one domain of δ-galactosidase (ED or EA). Upon agonistic stimulation of one RTK receptor, both RTK receptors dimerize, inducing formation of an active fully reconstituted β-galactosidase enzyme. Ultimately, β-galactosidase activity is measured by adding a substrate that upon hydrolyzation will lead to light emission.

Figure 3A:
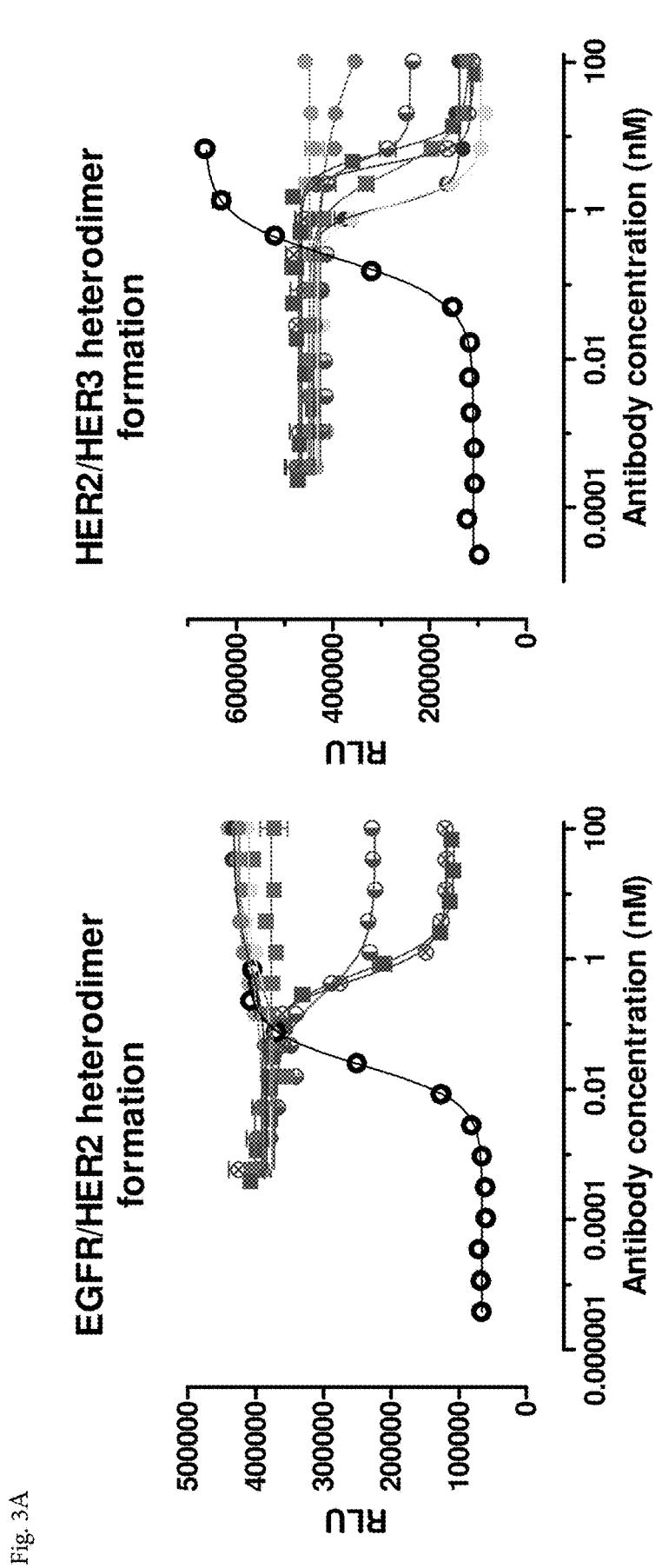
FIG. 3A and FIG. 3B: Antibody antagonist mode dose response curves in EGFR:HER2 (FIG. 3A, left), HER2:HER3 (FIG. 3A, right) and HER2:HER4 (FIG. 3B) assays. Reporter cells were seeded for 4 hr at 37° C. at 2.5K/well in the case of EGFR:HER2 or 5K/well in the case of HER2:HER3 and HER2:HER4. Antibodies were serially diluted and incubated for 3 hr at 37° C. prior to stimulation for 16 hrs with 10 ng/ml EGF or 30 ng/ml HRG-62 in the case of EGFR:HER2 or HER2:HER3 and HER2:HER4, respectively. Reference stimulation curves of agonists were obtained by incubating titrations of ligands alone for 24 hrs. Each data point represents the mean and standard deviation of four replicates per dose. Data were plotted in GraphPad Prism and curve fits were performed using a log (inhibitor) vs response-variable response (4 parameters) fit to calculate IC50's.
Figure 3B:
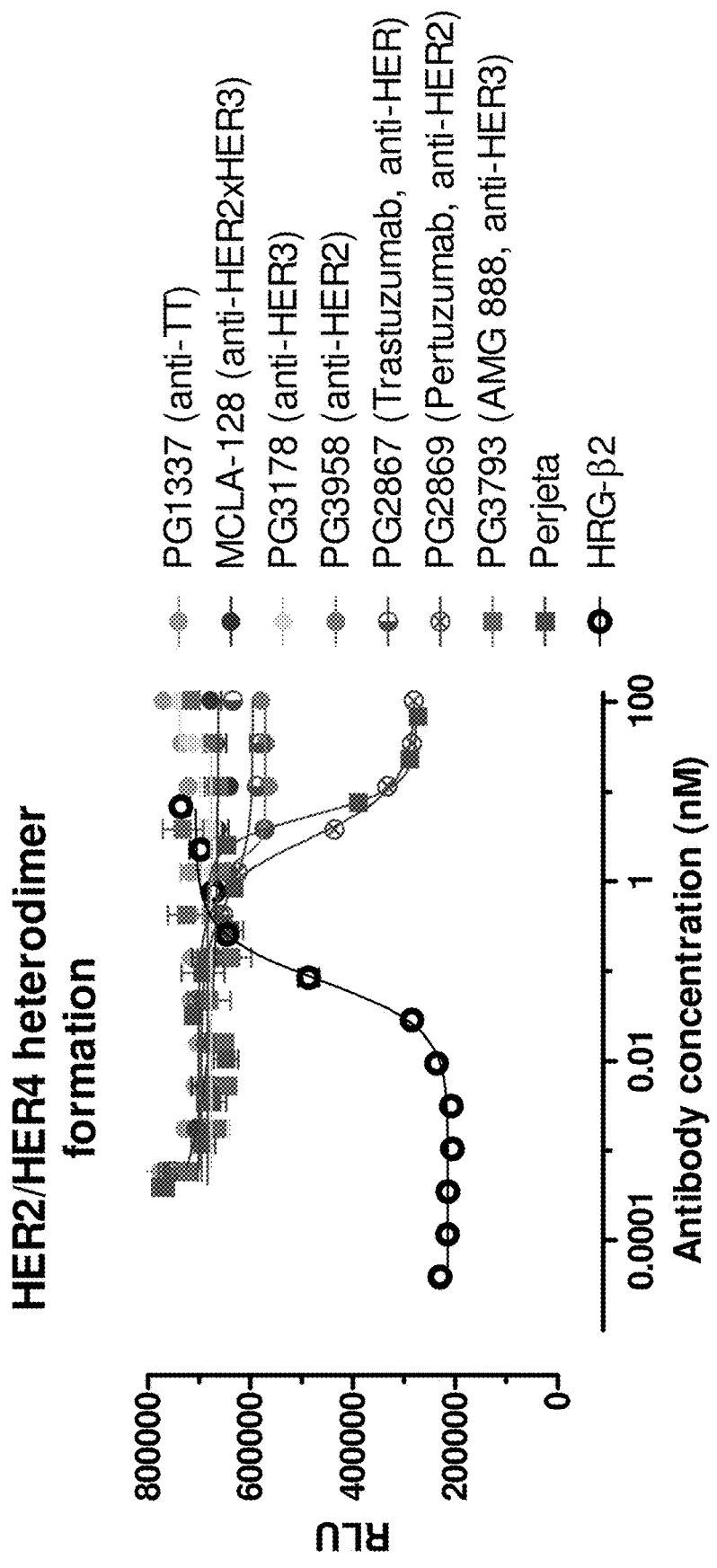

Antibodies where tested in EGFR:HER2, HER2:HER3 and HER3:HER4 heterodimerization reporter cell lines. RTK heterodimerization assays were run with the bispecific antibody MCLA-128 (MF3178 arm and MF3958 arm); anti-HER3 antibodies MF3178/PG3178 and PG3793/AMG-888/patritumab; and anti-HER2 antibodies MF3958/PG3958, PG2867/trastuzumab, PG2869/pertuzumab, and Perjeta (clinical batch of pertuzumab). EGF and HRG titrations in EGFR:HER2 and HER2:HER3, HER2:HER4 assays showed dose-dependent agonist responses (FIG. 3). MCLA-128 showed complete inhibition of HER2:HER3 dimer formation specifically and had no effect on EGFR:HER2 or HER2:HER4 heterodimerization. In contrast, trastuzumab (PG2867) behaved as partial antagonist in EGFR:HER2 and HER2:HER3 assays.

MCLA-128 and PG3178 fully inhibited HRG-induced HER2:HER3 dimerization with the highest potency (Table 1).

TABLE 1

Summary results of EC50 of antibodies tested in RTK heterodimerization assays. EC50 were determined non-linear regressions (4 parameters) in Prism.

| IC50 (nM) | EGFR:HER2 | HER2:HER3 | HER2:HER4 |
|---|---|---|---|
| PG1337 | — | — | — |
| PB4188 | — | 1.12 | — |
| PG3187 | — | 1.27 | — |
| PG3958 | — | — | 1.69 |
| PG2867 | 0.30 | 4.91 | 0.63 |
| PG2869 | 0.47 | 4.22 | 2.91 |
| PG3793 | — | 3.23 | — |
| Perjeta | 0.61 | 6.26 | 5.44 |
| Agonist | 0.02 | 0.22 | 0.08 |

The potency of trastuzumab was about 4-fold lower than MCLA-128 or PG3178 in the HER2:HER3 assay. Perjeta (clinical pertuzumab) behaved as full antagonist in all three assays and gave a similar profile as PG2867 (pertuzumab). In HER2:HER4 assays, both anti-HER2 PG3958 and PG2867 (pertuzumab) showed minor decreases in dimerization that appeared to be dose-dependent. Small non-specific responses in EGFR:HER2 assays were observed at high concentrations of PG1337, MCLA-128, PG3178 and PG3958.

MCLA-128 showed specific inhibition of HER2:HER3 heterodimers only. This indicates that upon binding on HER2, MCLA-128 should not sterically impair interaction of HER2 with EGFR upon EGF stimulation, nor impair heterodimerization of HER2 with HER4 upon HRG stimulation.

The latter is in line with observation in the HRG-induced cell cycle-based proliferation assay of T47D cells. Assays using these cells failed to demonstrate inhibitory activity of MCLA-128 or PG3178, which was presumably attributed to the higher expression of HER4 compared to HER3. HRG is thought to preferably signal via HER2:HER4 in T47D cells instead of HER2:HER3, explaining the lack of efficacy of MCLA-128 and indicating a specificity of MCLA-128 for HRG-induced HER2:HER3 dimers and not for HRG-induced HER2:HER4 dimers.

In the current study, trastuzumab blocked EGF- and HRG-induced heterodimerization of EGFR:HER2 and HER2:HER3, respectively. Trastuzumab and pertuzumab behaved as partial and full antagonist, respectively, which is in line with the generally accepted claim that trastuzumab blocks ligand-independent activation of HER2 while pertuzumab inhibits ligand-dependent signaling. The fact that a trastuzumab inhibitory response is observed in these assays might be due to the overexpression of both targets. This might allow a more sensitive readout than traditional immunoprecipitation experiments.

Finally, while PG3793 showed a lower binding affinity than PG3178 on MCF-7, its lower potency in HER2:HER3 heterodimerization assay is less severe (2.5-fold difference in dimerization assay potency versus 30-fold difference in binding assay affinity). This discrepancy between binding affinity and antagonism potency has previously been observed in the case of MCLA-128 and PG3178. While PG3178 binds MCF-7 with a slightly better affinity than MCLA-128, MCLA-128 outperforms PG3178 in a cell cycle-based proliferation assay.

Example 3

Study Objective and Regulatory Compliance

The objective of the research is to evaluate the in vivo anti-tumor efficacy of MCLA-128, PG2863 and PG2869 antibodies in the treatment of the subcutaneous human ovarian cancer PDX model of OV-10-0050 in BALB/c nude mice.

Experimental Design

The experimental design is indicate in table 2. In all groups, blood was sampled in 4 animals on day 2 (24 hr post first dose) and in the remaining 4 animals on day 6 (5 days post first dose). At the designated time point, 50-100 µl blood was collected into sterile collection tubes (Microvette CB300Z clotting activator/serum, Sarstedt B.V. cat #16.440.100), allowing the samples to clot at room temperature for 45 minutes, centrifuging for 10 minutes at 3000 rpm and taking up the aqueous layer (about 20 µl serum) into another 1.5 mL sterile Eppendorf for immediate storage at −80° C. Samples are shipped on dry ice.

TABLE 1

Description of Experimental Design

| Group | N[a] | Treatment | Dose mg/kg | Dosevolume ml/kg[b] | Conc. mg/ml |
|---|---|---|---|---|---|
| 1 | 8 | Vehicle Control (DPBS) | — | 10 | — |
| 2 | 8 | MCLA-128 | 25 | 10 | 2.5 |
| 3 | 8 | PG2863 | 25 | 10 | 2.5 |
| 4 | 8 | PG2869 | 25 | 10 | 2.5 |

[a]N: number of animals per group;
[b]Dose volume: adjust dosing volume based on body weight 10 µl/g.

All animals were treated on day 1, 8, 15, 22, 29 (weekly treatment for 5 weeks) Route was I.P. for all groups Tumor samples were harvested at 48 hr post last dose (day 31). Tumors were fixed in neutral buffered formalin (tissue:fixative ratio of at least 1:20) for 24 hrs, and then converted to FFPE blocks.

Preparation of Neutral buffer formalin: Put one bag of PBS powder in a clear 5 L-volumetric flask, added 4.5 L de-ionized water and stirred to disperse the powder to obtain a clear solution. Then added 500 ml formaldehyde to stir until a homogenous solution was achieved.

Materials

Animals: Species: *Mus musculus*: Strain: BALB/c nude; Age: 6-8 weeks; Sex: female Body weight: 18-22 g; Number of animals: 32 mice plus spare Animal supplier: Shanghai Sino-British SIPPR/BK Laboratory Animal Co., LTD.

Diet: Animals had free access to irradiation sterilized dry granule food during the entire study period; Water: Animals had free access to sterile drinking water.

Antibody Package and Storage Condition:

MCLA-128; cryovials, 10×1.5 ml/vial at 2.5 mg/ml, stored at 4° C.

PG2863; cryovials, 10×1.5 ml/vial at 2.5 mg/ml, stored at 4° C.

PG2869; cryovials, 10×1.5 ml/vial at 2.5 mg/ml, stored at 4° C.

Generation of the PDX Model

The human ovarian cancer PDX model of OV-10-0050 was originally established from a 48 years old female patient presenting grade 3 adenocarcinoma of the ovaries. A surgically resected clinical sample was implanted in nude mice (defined as passage 0, P0) and the following serial implantations were defined as P1, P2, etc. The P6 tumor tissue was used for this study.

Tumor Implantation Each mouse was implanted subcutaneously at the right flank with the OV-10-0050 P6 tumor slices which cut by scissor (~30 mm3) for tumor development. The treatments were started on day 30 after tumor implantation when the average tumor size reached approximately 152 mm3. 32 tumor bearing mice were randomized into 4 groups with a stratified randomization method and each group consisted of 8 tumor-bearing mice. The day of randomization was noted as day 1, and it was day of start of treatment. The test articles were administered to the mice according to the predetermined regimen as shown in the experimental design table (Table 2).

Observations

All the procedures related to animal handling, care and the treatment in the study were performed according to the guidelines approved by the Institutional Animal Care and Use Committee (IACUC) of WuXi AppTec following the guidance of the Association for Assessment and Accreditation of Laboratory Animal Care (AAALAC). At the time of routine monitoring, the animals were daily checked for any effects of tumor growth and treatments on normal behavior such as mobility, food and water consumption (only by visual inspection), body weight gain/loss (body weights were measured twice weekly), eye/hair matting and any other abnormal effect as stated in the protocol. Death and observed clinical signs were recorded on the basis of the numbers of animals within each subset.

Tumor MEASUREMENTS

Tested was whether the tumor growth could be delayed or if mice could be cured. Tumor size was measured twice weekly in two dimensions using a caliper, and the volume was expressed in mm3 using the formula: V=0.5 a×b2 where a and b are the long and short diameters of the tumor, respectively. The tumor size was then used for calculations of T-C, T/C and TGI values. T-C was calculated with T as the median time (in days) required for the treatment group tumors to reach a predetermined size (e.g., 500 mm3), and C as the median time (in days) for the control group tumors to reach the same size. The T/C value (in percent) is an indication of antitumor effectiveness; T and C were the mean volumes of the treated and control groups, respectively, on a given day. TGI was calculated for each group using the formula: TGI (%) [1−(Ti−T0)/(Vi−V0)]×100; Ti was the average tumor volume of a treatment group on a given day, T0 was the average tumor volume of the treatment group on the first day of treatment, Vi was the average tumor volume of the vehicle control group on the same day with Ti, and V0 was the average tumor volume of the vehicle group on the first day of treatment.

Statistical Analysis

Summary statistics, including mean and the standard error of the mean (SEM), are provided for the tumor volume of each group at each time point (detailed in table 3). Statistical analysis of difference in tumor volume among the groups and the analysis of drug interaction were conducted on the data obtained at the best therapeutic time point after the final dose (the 29th day after grouping).

A one-way ANOVA was performed to compare tumor volume among groups, and when a significant F-statistics (P<0.001, a ratio of treatment variance to the error variance) was obtained, comparisons between groups were carried out with Games-Howell. All data were analyzed using SPSS 17.0. p<0.05 was considered to be statistically significant.

Results

Mortality, Morbidity, and Body Weight Gain or Loss

Animal body weight was monitored regularly as an indirect measure of toxicity. No groups lost weight as a result of test article administration (FIG. 4) and no deaths or morbidity were observed. Thus, there does not appear to be obvious toxicity associated with administering MCLA-128, PG2863 and PG2869 antibodies to tumor-bearing BALB/c nude mice.

Figure 4:
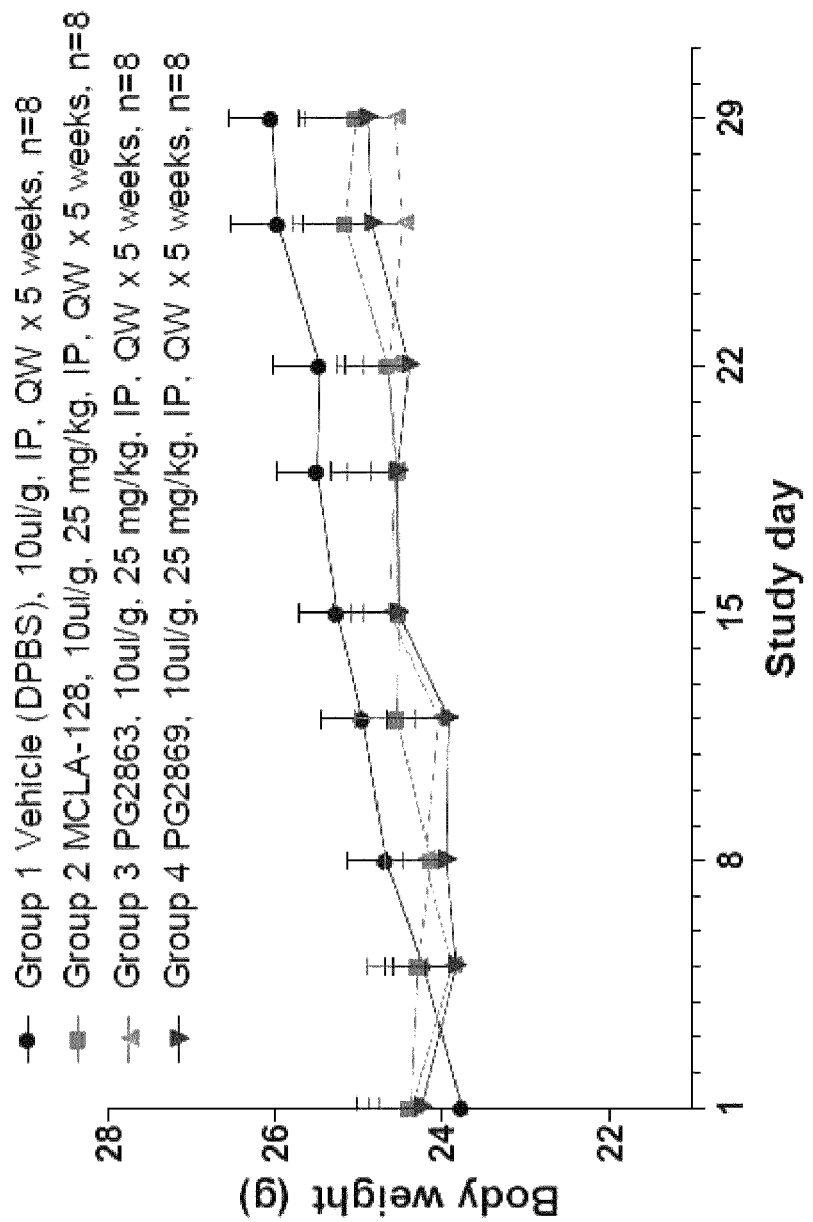
FIG. 4: Body Weight Changes of Mice in the Different Groups. Body weight changes after administering MCLA-128, PG2863 and PG2869 antibodies to female BALB/c nude mice bearing OV-10-0050 established tumors. Data points represent group mean body weight. Error bars represent standard error of the mean (SEM).
Figure 5:
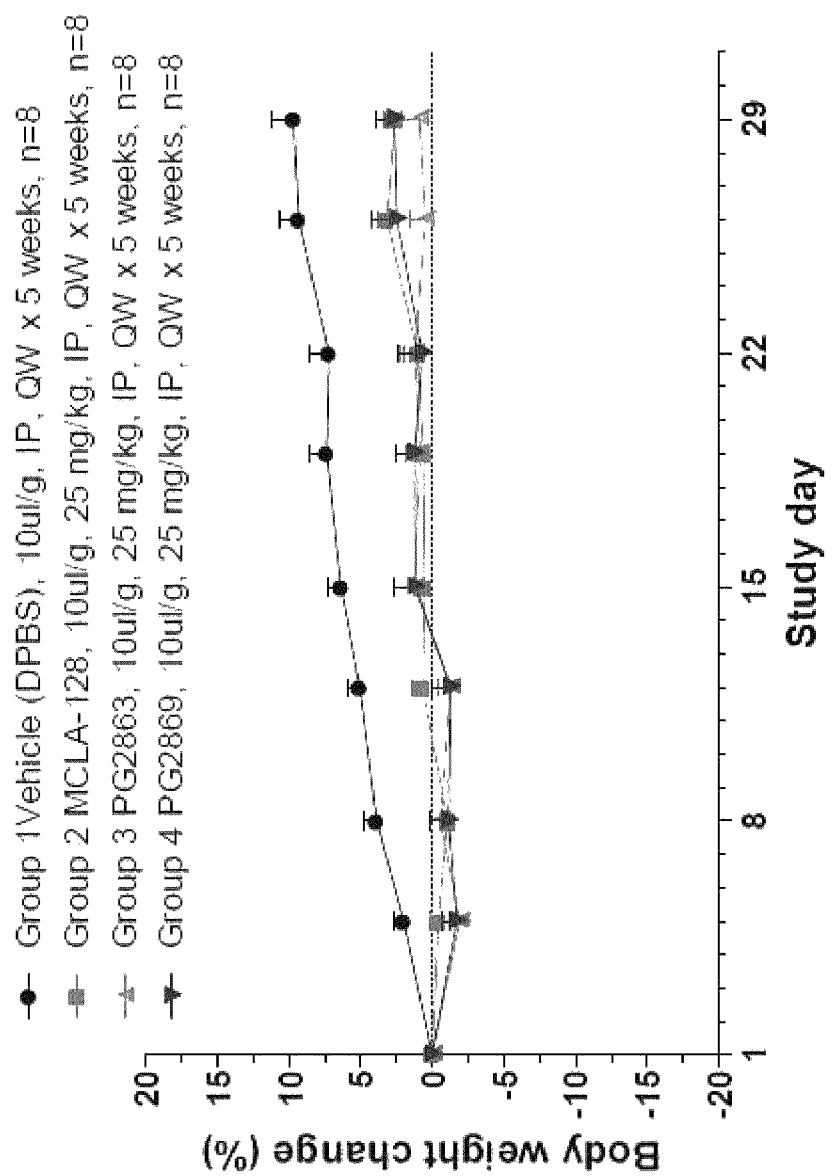
FIG. 5: Relative Change of Body Weights (%). BW change was calculated based on animal weight on the first day of dosing. Data points represent percent group mean change in BW. Error bars represent standard error of the mean (SEM).
Figure 6:
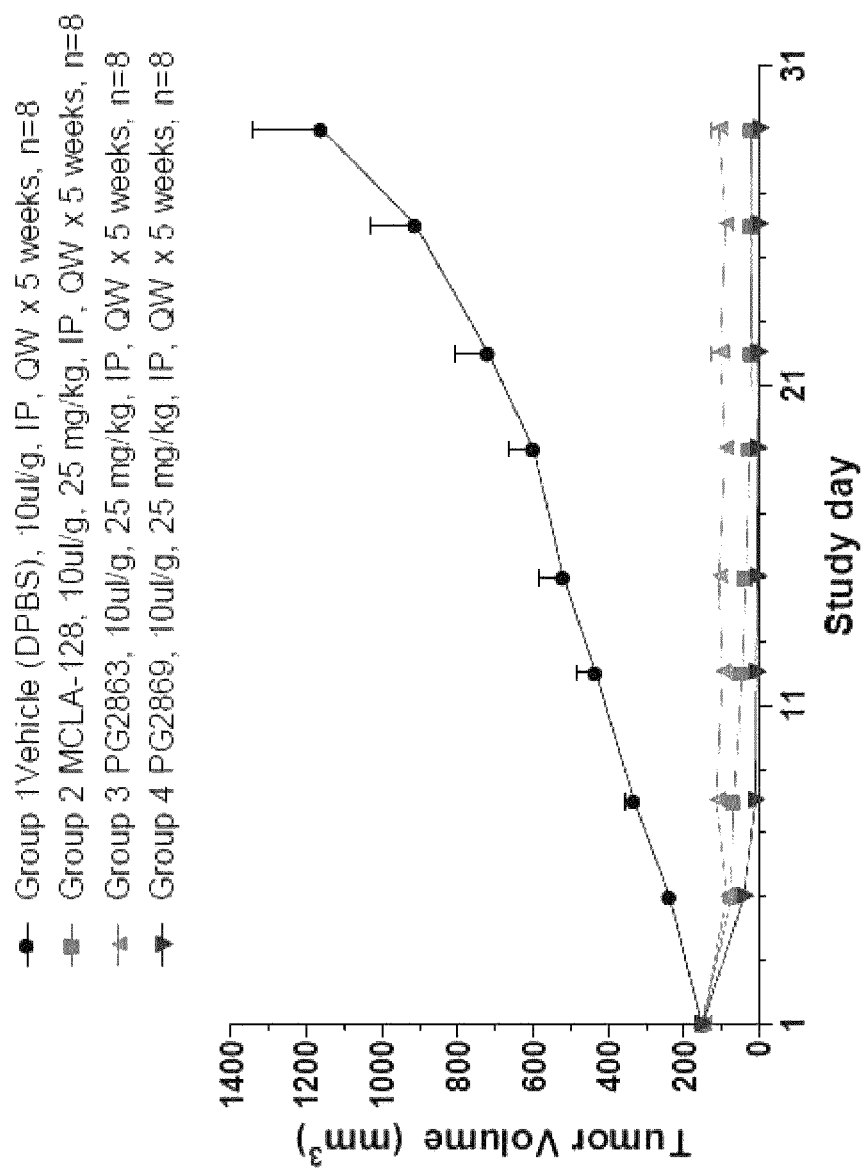
FIG. 6: Tumor Growth Curve. Tumor volume trace after administering MCLA-128, PG2863 and PG2869 antibodies to female BALB/c nude mice bearing OV-10-0050 established tumors. Data points represent group mean, error bars represent standard error of the mean (SEM).

Body weight change in female BALB/c nude mice bearing OV-10-0050 xenografts dosed with MCLA-128, PG2863 and PG2869 antibodies are shown in FIG. 4 and FIG. 5. Mean tumor volume over time in female BALB/c nude mice bearing OV-10-0050 xenografts dosed with MCLA-128, PG2863 and PG2869 antibodies are shown in Table 3. FIG. 6 shows the tumor growth.

TABLE 3

Tumor volume over time (mm$^3$)$^a$

| Days$^b$ | Vehicle (DPBS) | MCLA-128 25 mg/kg | PG2863 25 mg/kg | PG2869 25 mg/kg |
| --- | --- | --- | --- | --- |
| 1 | 152 ± 17 | 151 ± 21 | 152± | 152 ± 21 |
| 5 | 239 ± 18 | 75 ± 12 | 87 ± 10 | 41 ± 8 |
| 8 | 332 ± 26 | 69 ± 15 | 115± | 12 ± 1 |
| 12 | 434 ± 50 | 47 ± 11 | 98 ± 13 | 9 ± 1 |
| 15 | 520 ± 63 | 36 ± 10 | 108± | 6 ± 1 |
| 19 | 598 ± 64 | 26 ± 8 | 92 ± 16 | 4 ± 1 |
| 22 | 718 ± 88 | 23 ± 8 | 106± | 3 ± 1 |
| 26 | 911 ± 118 | 21 ± 9 | 91 ± 16 | 2 ± 1 |
| 29 | 1,161± | 23 ± 11 | 108± | 1 ± 0 |

$^a$Mean ± SEM;
$^b$Study day

Results and Discussion

In the study, the therapeutic efficacy of MCLA-128, PG2863 and PG2869 antibodies as a single agent in the treatment of the OV-10-0050 human ovarian cancer xenograft model was evaluated. The results of tumor sizes in different groups at different time points after tumor inoculation are shown in the Table 3, Table 4, and FIG. 4.

The mean tumor size of the vehicle treated control mice reached 1,161 mm$^3$ at day 29 after grouping. Treatment with the test articles MCLA-128, PG2863 and PG2869 antibodies at 25 mg/kg (QW×5 weeks) produced significant antitumor activity: their mean tumor sizes were 23, 108 and 1 mm3, respectively at the same time (T/C value=1.95%, 9.28% and 0.06%; TGI value=112.78%, 104.37% and 114.96%; p value=0.002, 0.003 and 0.002, respectively) their tumor growth all delays more than 14 days, at the tumor size of 500 mm³ compared with the vehicle group. Treatment causes partial regression or complete regression of the tumor. A mouse was considered to have a partial regression (PR) when tumor volume was reduced 50% or greater of its day 1 volume for three consecutive measurement during the course of the study and >13.5 mm³ for one or more of these three measurements. And to have a complete regression (CR) when <13.5 mm³ for three consecutive measurement during the course of the study. Tumor free survival was considered as no palpable tumor was detected at the end of the study.

Treatment with MCLA-128, PG2863 and PG-2869 resulted different ratio of PR, CR and TFS. The mouse amount in each group that shows PR, CR and TFS is shown is table 5. All the testing articles were tolerated well by the tumor-bearing animals. No body weight loss was observed in all of treatment groups.

In summary, the three test antibodies as single agent all produced significant antitumor activity against the OV-10-0050 human ovarian cancer xenograft model in this study. It was well tolerated by the tumor-bearing animals. The results indicated that the antibodies are safe and effective anticancer agents.

MCLA-128 also shows anti-tumor activity in cells expressing gene fusions involving the HRG gene. The MDA-MB-175 cell line contains the DOC4-NRG1 gene fusion, which results in a proliferative autocrine loop due to NRG1 expression. This gene fusion has until this date not been discovered in a cancer patient setting [Sanchez-Valdivieso 2002].

Figure 7:
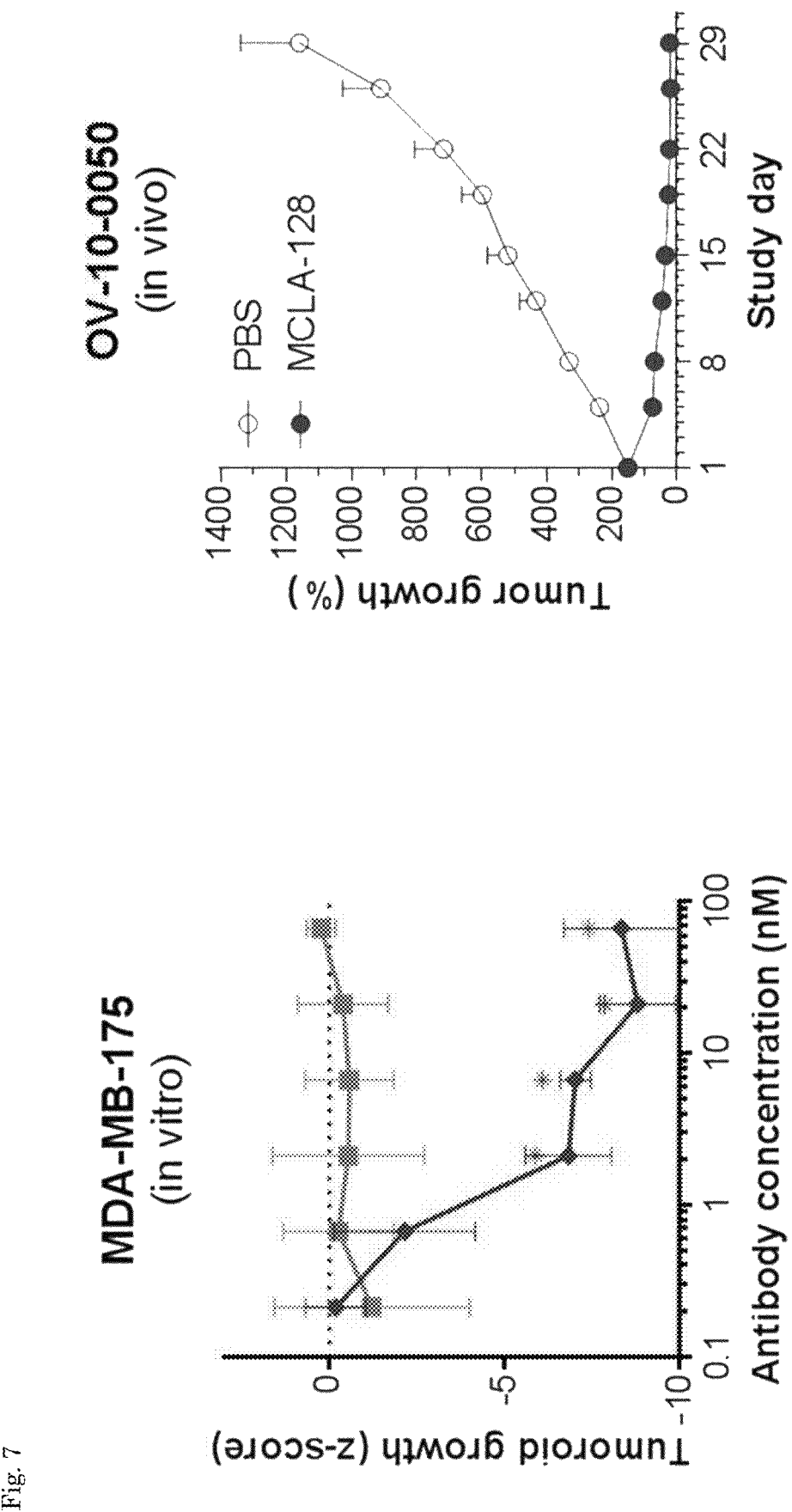
FIG. 7: Growth inhibition of tumor line MDA-MB-175 and OV-10-0050 in vitro and in vivo.

From a panel of breast cancer cell lines, MDA-MB-175 cells were sensitive to single agent MCLA-128, demonstrating the importance of the HER3/HRG signaling axis in this cell line (FIG. 7 left panel). The activation of the HER2 in this cell line has also been demonstrated in vivo, where a single dose of pertuzumab, but not trastuzumab, inhibited orthotopic MDA-MB-175 tumor growth. Although the relevance of DOC4-NRG1 gene fusion in breast cancer patients has been debated [Sanchez-Valdivieso 2002], other gene fusions have recently gained interest. In particular, the CD74-NRG1 fusion has been reported by independent groups in invasive mucinous adenocarcinoma, a subpopulation of non-small cell lung cancer [Fernandez-Cuesta 2014, Duruisseaux 2016]. Several other NRG1 gene fusions have also been detected, namely VAMP2-NRG1, RBPMS-NRG1 and WRN-NRG1 in lung cancer, as well as RAB2IL1-NRG1 in ovarian cancer [Jung 2015, Dhanasekaran, 2014]. This diversity of gene fusions may be

TABLE 4

Tumor growth inhibition calculation for injected MCLA-128; PG2863 and PG2869 antibodies in the OV-10-0050 model calculated based on tumor volume measurements at day 29 after grouping.

| Treatment | Tumor Size (mm³)ᵃ | T/Cᵇ (%) | TGI (%) | T-C (days) At 500 mm³ | p valueᶜ |
|---|---|---|---|---|---|
| Vehicle (DPBS) | 1,161 ± 182 | — | | 0 | — |
| MCLA-128 (25 mg/kg) | 23 ± 11 | 1.95 | 112.78 | >14 | 0.002 |
| PG2863 (25 mg/kg) | 108 ± 22 | 9.28 | 104.37 | >14 | 0.003 |
| PG2869 (25 mg/kg) | 1 ± 0 | 0.06 | 114.96 | >14 | 0.002 |

ᵃMean ± SEM.
ᵇTumor Growth Inhibition is calculated by dividing the group average tumor volume for the treated group by the group average tumor volume for the control group (T/C). For a test article to be considered to have anti-tumor activity, T/C must be 50% or less. TGI is calculated using the formula TGI (%) = [1 − (Ti − T0)/(Vi − V0)] × 100.
ᶜp value is calculated based on tumor size, compared with the vehicle group.

TABLE 5

PR, CR and TFS statistics for different treatments

| Treatment | PR | CR | TFS |
|---|---|---|---|
| MCLA-128 (25 mg/kg) | 3 | 5 | 0 |
| PG2863 (25 mg/kg) | 3 | 0 | 0 |
| PG2869 (25 mg/kg) | 0 | 8 | 3 |

Example 4

MCLA-128 is a bispecific antibody targeting HER2 and HER3 receptor tyrosine kinases (RTK), which are involved in the proliferation and survival of cancer cells. MCLA-128 has been extensively studied in the context of heregulin (HRG)-induced HER3 signaling and proliferation. It has demonstrated stronger in vitro potency than: the combination of anti-HER2 antibodies pertuzumab (PG2869)+ trastuzumab (PG2867), which can block ligand-dependent and ligand-independent HER2:HER3 signaling, respectively [Agus 2002; Juntilla 2009]; the anti-HER3 MM-121 (PG2863), which blocks HRG-induced HER3 activation [Schoeberl 2010].

related to the location of NRG1 gene on chromosome 8, which is susceptible to translocations [Adelaide 2003].

OV-10-0050 was found to be HER-dependent. Treatment with afatinib (an irreversible inhibitor of EGFR and HER2 that also inhibits transphosporylation of HER3) led to tumor growth inhibition. The anti-tumor efficacy of MCLA-128 was compared to PBS (FIG. 7, right panel).

Mice: NOD-SCID, Crl:NU(NCr)-Foxn1nu and BALB/c Nude mice. Antibodies are dosed at 25 mg/kg during 4 weeks. Tumor volumes are measured by caliper twice a week.

Example 5: A Phase I/II Study of MCLA-128, a Full Length IgG1 Bispecific Antibody Targeting HER2 and HER3, in Patients with Solid Tumors Study Duration:

Accrual to the dose escalation part of the study (Part 1, first patient dosed on Feb. 3, 2015), has been completed after recruiting 28 patients. The first patient in Part 2 of the study, the dose expansion phase, was dosed on 15 Jan. 2016 in Europe. The total duration of Part 2 is approximately 25-32 months; however, the actual duration is influenced by several variables, e.g., overall subject recruitment rate.

Number of Sites:

Up to 13 sites are estimated to be involved during the study. Additional sites may be added to ensure there is an acceptable enrollment rate or to replace non-enrolling/withdrawn sites.

Number of Patients:

Twenty-eight (28) patients were enrolled in Part 1. For Part 2, at least 20 evaluable patients, and up to approximately 40, may be enrolled in the grouped advanced/metastatic non-small cell lung cancer with invasive mucinous adenocarcinoma or documented NRG1 fusion; NSCLC).

Patients who do not complete at least two cycles of study treatment due to other reasons than disease progression, are not evaluable for efficacy and are replaced in the respective group.

This Example describes Part 2. While the example describes the administration of MCLA-128, an Erb-2, Erb-3 binding bispecific antibody, the example is not intended to be limiting to the use of this specific embodiment and applies to other bispecific antibodies disclosed herein.

Study Objectives:

Part 1

| Objective | |
|---|---|
| Primary: | |
| Determination of the MTD and/or MRD of MCLA-128. | Evaluation of adverse events (AEs) and dose limiting toxicities (DLT). |
| Secondary: | |
| To characterize the safety and tolerability of MCLA-128. | Frequency and nature of AEs/serious adverse events (SAEs). |
| PK profile of MCLA-128. | Assessment of PK variables, including total exposure, maximum concentration ($C_{max}$) clearance, volume of distribution (V), volume of distribution at steady state ($V_{ss}$), half-life ($t_{1/2}$), $AUC_{0-t}$ (area under the concentration versus time curve from time zero to time t), $AUC_{0-\infty}$ (area under the concentration versus time curve), $t_{max}$ (time to reach maximum concentration). |
| Immunogenicity of MCLA-128. | Incidence and serum titers of anti-drug antibodies against MCLA-128. |
| Evaluation of anti-tumor response and CBR. | Anti-tumor activity and clinical benefit assessed by RECIST v1.1 determining objective overall response rate (ORR), duration of response (DOR), progression-free survival (PFS) and survival; CBR is defined as the proportion of patients in whom a complete response (CR) or partial response (PR) or stable disease (SD) is observed (where SD) duration is a minimum of 12 weeks). |
| Exploratory (includes optional assessments): | |
| Presence of biomarkers and pharmacodynamic (PD) responses to MCLA-128. | Assessment of relevant tumor biomarkers and markers of MCLA-128 activity in archival and/or fresh tumor biopsy material and blood. The following candidate biomarkers are assessed: HER2, HER3, pHER2, pHER3 & heregulin; KRAS, NRAS, PIK3CA, BRAF mutation status (metastatic colorectal cancer (mCRC) patients only); circulating tumor deoxyribonucleic acid (DNA) and mutations in genes associated with HER2/HER3 signaling; phosphorylated molecules in the MAPK and AKT signaling pathway. |

Part 2

| Objective | |
|---|---|
| Primary (safety): | |
| To characterize the safety and tolerability of MCLA-128. | Frequency and nature of AEs. |
| Primary (efficacy): | |
| To explore the relationships between the anti-tumor activity of MCLA-128 and disease-related biomarkers | Overall response rate (ORR), DOR, CBR (defined as the proportion of patients in whom a CR or PR is observed, or SD of a minimum duration of 12 weeks) per RECIST 1.1 as per local investigator's assessment. The relationship between anti-tumor activity and biomarkers including expression of HER2, HER3, and heregulin are explored, and serum biomarkers such as CA-125 (ovarian, endometrial) and CA-19-9 (gastric) |
| Secondary: | |
| PK profile of MCLA-128. | Assessment of PK variables, including total exposure, $C_{max}$, V, $V_{ss}$, $t_{1/2}$, $AUC_{0-t}$, $AUC_{0-\infty}$, $t_{max}$. Population PK analysis |
| Immunogenicity of MCLA-128. | Incidence and serum titers of anti-drug antibodies against MCLA-128. |
| Evaluation of PFS and overall survival, duration of response | |
| Exploratory (includes optional assessments): | |
| Assessment of other relevant tumor biomarkers and markers of MCLA-128 activity in preferably fresh tumor sample/biopsy material or archival and blood. | The following candidate biomarkers are assessed if sufficient sample is available: Tumor sample pHER2, pHER3, HER2:HER3 dimerization; |

| Objective | |
|---|---|
| | Hereregulin and (depending on availability) mutations in cancer genes including those associated with HER2 and HER3 Phosphorylated molecules in the MAPK and AKT signaling pathway. Heregulin-gene fusions Blood Fcgamma receptor polymorphism Circulating tumor DNA and mutation analysis in cancer genes including those associated with HER2/HER3 signaling; Circulating tumor cells and HER2 status |

Study Design:

This is a Phase I/II, open-label, multi-center, multi-national, dose escalation, single group assignment study to assess the safety, tolerability, PK, PD, immunogenicity and anti-tumor activity of MCLA-128.

The study is designed in 2 parts:

Part 1

Accrual to Part 1 of the study was met on 24 Nov. 2015 and as of 24 Jan. 2017 all Part 1 patients had completed the study. Nine dose levels were investigated: 40 mg, 80 mg, 160 mg in cohorts of 1 patient and 240 mg, 360 mg, 480 mg, 600 mg, 750 mg, and 900 mg in cohorts of 3 patients. MCLA-128 was initially given over approximately 60 minutes on Day 1 of a 3-week treatment cycle. During Part 1 the infusion duration was extended to 2 hours with the option of increasing it up to 4 hours to mitigate infusion-related reactions (IRRs).

No dose limiting toxicities (DLTs) were experienced at any of the dose levels. Three additional patients were dosed in each of the 600 mg and 750 mg cohorts in order to have sufficient PK information.

As an MTD was not reached at the dose level of 900 mg, the Data Review Committee (DRC) for MCLA-128-CL01 decided to assign the dose level of 750 mg as the RP2D of the study, based on the cumulative safety, available PK data and PK simulations.

Part 2

Part 2 includes a further characterization of the safety and tolerability of the selected dose level of MCLA-128, as well as assessment of CBR, defined as the proportion of patients with a CR, PR or durable SD (SD for at least 12 weeks in duration), in expansion groups of selected patient populations.

A weekly dose regimen with a 4-week cycle is evaluated in newly recruited patients consisting of a flat dose of 400 mg weekly for the first 2 cycles, with an 800 mg loading dose for the initial administration. From cycle 3, MCLA-128 is given at a dose of 400 mg weekly for 3 weeks followed by 1 week off. Mandatory pre-medication is administered to mitigate IRRs. However, corticosteroids are only mandatory prior to the loading dose of Day 1 of Cycle 1 and should only be used for subsequent infusions as per the investigator's discretion to manage IRRs.

Safety of the weekly schedule is reviewed during a run-in period after the first 5 patients treated have completed at least 2 treatment cycles. The DRC reviews all safety data with a focus on incidence of grade 3-4 toxicities, incidence and severity of IRRs, and compliance. If the DRC review concludes that toxicity is unacceptable, the Sponsor continues patient enrolment with the 3-week cycle dose regimen until a sufficient number of patients have been enrolled per cohort.

No within-patient dose escalation is permitted in Part 2.

Patient populations of interest to be assessed in Part 2 of the study are:

NSCLC with documented NRG1 fusions-only open for recruitment in Asia

At least 20 and up to approximately 40 patients may be enrolled in each Group (C-F) including a minimum of 10 patients per cohort treated with the weekly recommended dose. Previously closed cohorts may be reopened.

Duration of Treatment

Patients in both Part 1 and 2 of the study may remain on treatment until disease progression, death, unacceptable toxicity or discontinuation for any other reason.

Data Review Committee (DRC):

All dose escalation decisions in Part 1 were made by a DRC who convened to review all available safety data and PK data. The DRC participants included the Principal Investigators (or their representatives), the Sponsor's Medical Director, the study Medical Monitor, study Pharmacovigilance Physician, study Project Manager, study Statistician, and invited experts as required (such as clinical pharmacology expert).

In Part 2, the DRC reviews the data following completion of the safety run-in period for the weekly dose before expanding the weekly dose regimen in all subsequent patients.

Study Assessments:

The study consists of a molecular pre-screening assessment up to a 4-week (28-day) screening period, followed by sequential treatment cycles until treatment withdrawal or termination for any reason. The treatment cycle duration is 3 weeks (21 days) for patients treated at the initial recommended dose in Part 2, and 4 weeks (28 days) for patients treated at the weekly recommended dose in Part 2. All patients should attend an End of Treatment visit within 1 week after treatment cessation and a Final Study Visit 30 days after end of treatment or discontinuation from study.

Patients who have not progressed or withdrawn consent on completion of the Final Study Visit are followed up every 3 months for up to 2 years (approximately) to check their disease progression and/or survival status until the commencement of their next anti-cancer treatment.

Where ongoing evaluation of safety data and available PK, PD and anti-tumor activity data during the trial suggest that alternative dosing frequencies should be evaluated, or that other patient populations should be evaluated in Part 2, these modifications are clarified in a protocol amendment prior to commencing these evaluations.

Molecular Pre-Screening and Screening:

Molecular pre-screening is performed in local laboratories qualified to perform molecular screening for NRG1 fusions. To initiate pre-screening, a patient must meet one of the following criteria:

Histological diagnosis of IMA and documented absence of EGFR/ALK alterations. Note: IMA patients who have not performed the pre-screening test for NRG1 fusion can enter the trial.

OR

Pathological examination does not allow IMA diagnosis but the investigator suspects the IMA based on symptoms, imaging features (e.g. localized consolidation, multiple bilateral nodules or consolidations), non-smoker and documented absence of EGFR/ALK alterations.

The molecular pre-screening Informed Consent Form (ICF) must be signed by NSCLC patients identified for potential study participation before the fresh or archival tumor tissue is submitted for analysis for determination of NRG1 fusion status. Testing can be performed at any time of the natural history of the disease (e.g. at diagnosis, during the first line of therapy, at progression, etc) up to a maximum of one year prior to Cycle 1 Day 1. A fresh tumor sample (formalin-fixed paraffin-embedded; FFPE) or an archival tumor sample not older than 1 year, is required for the assessment of the presence of the NRG1 fusion. The sample should be submitted to a local laboratory qualified for testing by molecular profiling (PCR, next generation sequencing [DNA or RNA] or FISH) of NRG1 fusion status. Patients with a positive local NRG1 fusion result are then eligible to sign the main study ICF if they are willing and able to enter the main study.

Main Informed Consent Form

The main study ICF must be signed by all patients prior to any screening procedures or assessments being conducted. The screening assessments are performed within 4 weeks prior to Cycle 1 Day 1, with the exception of the serum pregnancy test which must be conducted within 7 days of Cycle 1 Day 1. To be considered for screening, a baseline mandatory tumor sample, preferably a block, from fresh or archival tissue is requested. The sponsor indicates the preference for fresh tissue. Archival is acceptable and should have been taken within 2 years from screening other than for NSCLC which must be within 1 year. It should be noted that for NSCLC patients, the baseline biopsy for screening is still required even if a pre-screening biopsy sample is provided for pre-screening local testing of NRG1. Following completion of all required screening assessments and confirmation of all eligibility criteria the patient can begin dosing on Cycle 1 Day 1.

Safety Assessments

Concurrent illnesses are captured at baseline; AEs and concomitant therapies are monitored throughout study participation. Safety assessments include reviewing Eastern Cooperative Oncology Group (ECOG) performance status, physical examination (including height and weight), vital signs and electrocardiograms (ECG). A cardiac function test of the Left Ventricular Ejection Fraction (LVEF) is also be carried out at Screening, end of Cycle 4 (or Cycle 5 Day 1), End of Study Visit, and at any time during the study if clinically indicated. Laboratory evaluations include clinical chemistry, hematology, coagulation tests, urinalysis and pregnancy testing. Note that a cytokine panel analysis was performed up until 1 Aug. 2017.

On all MCLA-128 administration days, the patients must remain at the clinic for at least 60 minutes from the time of the end of infusion (longer where there are PK samples required) for observation and repeat vital signs prior to discharge from the clinic. Further additional safety assessments should be performed as clinically indicated and, if needed, duration of stay in clinic should be increased based on Investigator's judgment.

Immunogenicity Assessment

Serum titers of anti-MCLA-128 antibodies are measured on Day 1 at pre-dose for each of Cycles 1, 2, 3, 4 and then every fourth cycle thereafter (Cycle 8, 12, 16 etc), and at the End of Treatment Visit and the Final Study Visit with a window of −3 days prior to the MCLA-128 administration.

Pharmacokinetics Assessment

Part 1 and Part 2 initial recommended dose schedule: In Cycle 1, blood samples are collected for PK analysis on Day 1 at pre-dose, at end of infusion (EOI), and at 1, 2, 4, 8, 24 hours post EOI, then on Day 4 (or Day 3), Day 8 and Day 15. In Cycles 2-4, only a pre-dose and EOI blood sample is collected.

Part 2 weekly recommended dose schedule: In Cycle 1, blood samples are collected for PK analysis on Day 1 at pre-dose, EOI, 2, 4, 24 hours post EOI, then predose on Days 8 and 15, and predose and EOI on Day 22. In Cycles 2 and 3, a pre-dose and EOI blood sample is collected on Day 15. In Cycle 4 blood samples are collected pre-dose on Day 1, and pre-dose and EOI on Day 15. Every 2 cycles thereafter (Cycles 6, 8, 10 etc) a pre-dose blood sample is collected on Day 15.

Tumor Assessment

Tumor assessment is evaluated according to RECIST version 1.1 per local investigator. Imaging is obtained at Screening and at the end of every 2 cycles of treatment for patients receiving the 3-week cycle regimen and every 6 weeks for patients receiving the 4-week cycle regimen.

Biomarker and Pharmacodynamics Assessments

A range of biomarker and pharmacodynamic tests are performed on archived and/or fresh tumor sample material and/or blood (liquid biopsy), depending on availability of archived or existing tumor tissue, consent for further tumor samples, and consent for specific biomarker testing.

The following candidate biomarkers are assessed in case sufficient sample is available:

HER2, HER3, HER2:HER3 dimerization, phosphorylated HER2 (pHER2) and HER3 (pHER3) and heregulin;

Circulating plasma tumor DNA (ctDNA) and tumor sample DNA (depending on availability) are used to examine mutations in cancer genes including those associated with HER2 and HER3 signaling Phosphorylated molecules in the MAPK and AKT signaling pathway;

Fcgamma receptor polymorphism;

Circulating tumor cells for HER2;

Heregulin-gene fusions

No germ line DNA assessment is included (except for Fcgamma receptor polymorphism).

At baseline the patient is requested to provide a mandatory tumor sample tissue, preferably a block, which could be from fresh or archival tissue. The sponsor indicates the preference for fresh tissue. Archival is acceptable and should have been taken within 2 years from screening other than for NSCLC which must be within 1 year. In addition the patient is requested optionally to provide a tumor sample/biopsy at the end of Cycle 4 and optionally at the End of Treatment Visit.

Blood samples are also taken at these time points for the purpose of liquid biopsy testing.

Eligibility Criteria:

The study enrolls patients with NSCLC.

General Inclusion Criteria for Part 2

1. Age 18 years or older;
2. At least one measurable lesion according to RECIST v1.1;
3. Performance status of ECOG 0 or 1;
4. Estimated life expectancy of at least 12 weeks;

5. Toxicities incurred as a result of previous anti-cancer therapy resolved to ≤Grade 1 (as defined by NCI CTCAE v4.03), except for alopecia, lymphopenia assessed as non-clinically significant, Grade 2 sensory neurotoxicity;
6. At least a 4-week interval between the last received radiotherapy and the first scheduled day of dosing with MCLA-128 (with the exception of up to 1×8 Gy for pain palliation);
7. Complete recovery from major surgery (stable and <Grade 2 toxicity acceptable);
8. Laboratory values at Screening:
    a. Absolute neutrophil count ≥1.5×10$^9$/L without colony stimulating factor support;
    b. Platelets ≥100×10$^9$/L;
    c. Hemoglobin ≥9 g/dL or ≥2.2 mmol/L (not transfusion dependent);
    d. Total bilirubin <1.5 times the upper limit of normal (ULN) (unless due to Gilbert's syndrome);
    e. AST (SGOT)≤2.5×ULN; ALT (SGPT)≤2.5×ULN; ≤5×ULN for patients with advanced solid tumors with liver metastases; patients with confirmed bony metastases are permitted on study with isolated elevations in ALP>5×ULN;
    f. Serum creatinine ≤1.5×ULN or estimated glomerular filtration rate (GFR) of >50 mL/min based on the Cockroft-Gault formula;
    g. Coagulation function (INR and aPTT≤1.5 ULN, unless on therapeutic anticoagulants)
    h. Urine protein ≤2+(as measured by dipstick) or ≤100 mg/24 hours urine;
9. Able to provide at baseline a mandatory tumor biopsy sample (FFPE), preferably a block, from fresh (preferred) or archival tissue. Archival tissue must be collected within 2 years before screening, other than for NSCLC which must be within 1 year.
10. Negative pregnancy test results available as defined by urine or blood human chorionic gonadotropin (hCG) test during Screening and within 7 days of Cycle 1, Day 1 in women of childbearing potential (defined as women ≤50 years of age or history of amenorrhea for ≤12 months prior to study entry);
11. Sexually active male and female patients of childbearing potential must agree to use an effective method of birth control (e.g., barrier methods with spermicides, oral or parenteral contraceptives and/or intrauterine devices) during the entire duration of the study and for 6 months after final administration of MCLA-128. Note that sterility in female patients must be confirmed in the patients' medical records and be defined as any of the following: surgical hysterectomy with bilateral oophorectomy, bilateral tubular ligation, natural menopause with last menses >1 year ago; radiation induced oophorectomy with last menses >1 year ago; chemotherapy induced menopause with 1 year interval since last menses;
12. Ability to give written, informed consent prior to any study-specific Screening procedures, with the understanding that the consent may be withdrawn by the patient at any time without prejudice;
13. Capable of understanding the mandated and optional protocol requirements, is willing and able to comply with the study protocol procedures and has signed the main informed consent document. For any optional biopsy sampling (tissue and/or blood) and long-term sample storage, additional consent is required;
14. Patient with metastatic cancer who has disease progression after having received treatment with all available therapies known to convey clinical benefit.
15. Unresectable or metastatic NSCLC meeting one of the following conditions:
    Biopsy-proven invasive mucinous adenocarcinoma (IMA). Note: IMA patients who have not performed the pre-screening test for NRG1 fusion can enter the trial.
    OR
    NSCLC with documented NRG1 fusion determined at in a qualified local laboratory by molecular profiling using methods such as PCR, next generation sequencing [DNA or RNA] or FISH in patients with no known driver mutations or fusions in EGFR/ALK genes.
16. Documented disease progression by investigator assessment on at least one line of standard therapy in the locally advanced or metastatic setting Statistical Analysis:

Part 1 and Part 2

Anti-tumor and clinical benefit variables are summarized descriptively for each group in Part 2. Where appropriate, variables are presented in terms of absolute and relative change from baseline. Categorical data is presented as percentages and frequency tabulations.

Where appropriate, data from those patients who receive what becomes identified as the MTD or the MRD during Part 1, and those receiving the same dose in Part 2, may be combined and summarized, as well as being summarized independently.

The frequency and nature of serious and non-serious AEs is assessed in absolute and relative frequencies and coded according to MedDRA medical dictionary.

Part 1

Data evaluation is descriptive in nature. Patient demographics, disease characteristics and pharmacokinetic and pharmacodynamic variables are summarized at each dose level. The frequency and nature of DLTs are also summarized at each dose level.

Part 2

With N=20 per cohort in Part 2, clinically meaningful observed correlation coefficients of at least 0.38 would be distinguishable from zero with 95% confidence; lesser, non-clinically meaningful observed correlations would not be distinguishable from zero. Hence 20 subjects per cohort in Part 2 is considered sufficient to explore the relationship between the anti-tumor activity of MCLA-128 and disease related biomarkers.

In the event that signs of clinical activity are seen, additional patients up to a total of approximately 40 may be recruited. With 40 patients, true clinical response rates of, for example, 10% to 50% can be estimated with reasonable precision of approximately ±5% to ±8%.

PK parameters are summarized for each cohort in Part 1 and each tumor group in Part 2. Arithmetic and geometric means are provided in addition to medians, range, SD and % CV. AUC is calculated according to the trapezoid rule. Serum concentration profiles against time are plotted for each group.

REFERENCES

Yarden Y, Pines G. 2012. The ERBB network: at last, cancer therapy meets systems biology. Nat Rev Cancer July 12; 12(8):553-63.

Wilson T R, Fridlyand J, Yan Y, Penuel E, Burton L, Chan E, Peng J, Lin E, Wang Y, Sosman J, Ribas A, Li J, Moffat J, Sutherlin D P, Koeppen H, Merchant M, Neve R, Settleman J. 2012. Widespread potential for growth-factor-driven resistance to anticancer kinase inhibitors. Nature. July 26; 487(7408):505-9.

Balko J M, Miller T W, Morrison M M, Hutchinson K, Young C, Rinehart C, Sanchez V, Jee D, Polyak K, Prat A, Perou C M, Arteaga C L, Cook R S. 2012. The receptor tyrosine kinase ErbB3 maintains the balance between luminal and basal breast epithelium. Proc Natl Acad Sci USA. January 3; 109(1):221-6.

Zhang H, Berezov A, Wang Q, Zhang G, Drebin J, Murali R, Greene M I. 2007. ErbB receptors: from oncogenes to targeted cancer therapies. J Clin Invest. August; 117(8): 2051-8.

Sergina N V, Rausch M, Wang D, Blair J, Hann B, Shokat K M, Moasser M M. 2007. Escape from HER-family tyrosine kinase inhibitor therapy by the kinase-inactive HER3. Nature. January 25; 445(7126):437-41.

Junttila T T, Akita R W, Parsons K, Fields C, Lewis Phillips G D, Friedman L S, Sampath D, Sliwkowski M X. 2009. Ligand-independent HER2/HER3/PI3K complex is disrupted by trastuzumab and is effectively inhibited by the PI3K inhibitor GDC-0941. Cancer Cell. May 5; 15(5): 429-40.

Ocana A, Vera-Badillo F, Seruga B, Templeton A, Pandiella A, Amir E. 2013. HER3 overexpression and survival in solid tumors: a meta-analysis. J Natl Cancer Inst. February 20; 105(4):266-73.

Junttila, T. T., K. Parsons, et al. (2010). "Superior In vivo Efficacy of Afucosylated Trastuzumab in the Treatment of HER2-Amplified Breast Cancer." Cancer Research 70(11): 4481-4489

Merchant et al. Nature Biotechnology, Vol. 16 Jul. 1998 pp 677-681

Adelaïde et al. (2003) Genes Chromosome Cancer, 37(4), 333.

Agus et al. (2002) Cancer Cell 2(2), 127.

Birnbaum et al (2003). Lancet Oncol 4: 639-642.

Chua et al (2009). Oncogene 28, 4041-4052 Cooke et al (2008). BMC Cancer 8: 288.

Duruisseaux et al. (2016) NRG1 fusion in a French cohort of invasive mucinous lung adenocarcinoma. Canc Med.

Falls D L. (2003). Exp Cell Res 284: 14-30.

Fernandez-Cuesta et al. (2014) Canc Disc. 4(4), 415.

Fernandez-Cuesta and Thomas (2015). Clinical Cancer Research 21(9): 1989-1994.

Hayes and Gullick (2008). J Mammary Gland Biol Neoplasia 13: 205-214.

Jung et al. (2015) J Thor Oncol 10(7), 1107.

Juntilla et al. (2009) Cancer Cell 15(5), 429.

Pole et al (2006). Oncogene 25:5693-5706.

Sanchez-Valdivieso et al. (2002) Br J Canc, 86(8), 1362.

Schoeberl et al. (2010) Canc Res 70(6), 2485.

Weinstein et al. (1998). Oncogene 17: 2107-2113.

The invention claimed is:

1. A method of treating non-small cell lung cancer or pancreatic cancer in a subject, wherein the method comprises administering to the subject a bispecific antibody that comprises a first antigen-binding site that can bind an extracellular part of ErbB-2, and a second antigen-binding site that can bind an extracellular part of ErbB-3, wherein cells of said cancer comprise an NRG1 fusion gene comprising at least a portion of the NRG1-gene fused to a sequence from a different chromosomal location;
   the first antigen-binding site comprising a heavy chain CDR1 comprising the amino acid sequence of SEQ ID NO:40, a heavy chain CDR2 comprising the amino acid sequence of SEQ ID NO: 41, and a heavy chain CDR3 comprising the amino acid sequence SEQ ID NO:42; and
   the second antigen-binding site comprising a heavy chain CDR1 comprising the amino acid sequence of SEQ ID NO:54, a heavy chain CDR2 comprising the amino acid sequence of SEQ ID NO: 55, and a heavy chain CDR3 comprising the amino acid sequence SEQ ID NO:56; and
   wherein the first antigen binding site and the second antigen binding site comprise a light chain CDR1 comprising the amino acid sequence of SEQ ID NO:75, a light chain CDR2 comprising the amino acid sequence of SEQ ID NO:76, and a light chain CDR3 comprising the amino acid sequence SEQ ID NO:77.

2. The method of claim 1, wherein the NRG1 fusion gene comprises at least the 3' end of the NRG1-gene fused to a 5' sequence from a different chromosomal location.

3. The method of claim 1, wherein the cancer is non-small cell lung cancer.

4. The method of claim 3, wherein the non-small cell lung cancer is of the invasive mucinous adenocarcinoma subtype.

5. The method of claim 1, wherein the cancer is pancreatic cancer.

6. The method of claim 1, wherein the cancer is a metastasis of non-small cell lung cancer.

7. The method of claim 1, wherein the NRG1-fusion gene expresses a protein that comprises an NRG1 EGF-like domain.

8. The method of claim 1, wherein the NRG-fusion is a fusion of NRG1 and a gene on human chromosome 8.

9. The method of claim 8, wherein the gene on human chromosome 8 encodes an excreted protein or a cellular membrane associated protein.

10. The method of claim 1, wherein the NRG1 fusion gene is a fusion of the 3' end of the NRG1-gene with the 5' sequence of one of the genes selected from the group consisting of CD74; DOC4; TNFRSFIOB; CLU; VAMP2; SLC3A2; RBPMS; WRN; SDC4; KIF13B; SLECA2; PDE7A; ATP1B1; CDK1; BMPR1B; MCPH1 and RAB2IL1.

11. The method of claim 1, wherein the cell is of an epithelial origin.

12. The method of claim 1, wherein the subject has undergone a therapy targeted towards EGFR inhibition.

13. The method of claim 1, wherein a ErbB-1 cell-surface receptor density; a ErbB-2 cell-surface receptor density; a ErbB-3 cell-surface receptor density; a ErbB-4 cell-surface receptor density, or a combination thereof on the cell has been determined.

14. The method of claim 13, characterized in that the cell has less than 400,000 ErbB-1 cell-surface receptors per cell, or less than 200,000 ErbB-1 cell-surface receptors per cell.

15. The method of claim 1, further comprising administering to the subject an ErbB-1 inhibitor.

16. The method of claim 15, wherein the ErbB-1 inhibitor is cetuximab.

17. The method of claim 1, wherein the first antigen-binding site comprises a heavy chain comprising the amino acid sequence of SEQ ID NO:39.

18. The method of claim 1, wherein the second antigen-binding site comprises a heavy chain comprising the amino acid sequence of SEQ ID NO:53.

19. The method of claim 1, wherein the first antigen binding site and the second antigen binding site comprise a light chain comprising the amino acid sequence of SEQ ID NO: 78.

20. The method of claim 1, wherein the bispecific antibody comprises the first antigen-binding site comprising the amino acid sequence of SEQ ID NO:39, the second antigen-binding site comprising the amino acid sequence of SEQ ID NO:53, and the common light chain comprising the amino acid sequence of SEQ ID NO: 78.

* * * * *

SEQUENCE LISTING

```
Sequence total quantity: 151
SEQ ID NO: 1            moltype = DNA  length = 370
FEATURE                 Location/Qualifiers
misc_feature            1..370
                        note = MF2926
source                  1..370
                        mol_type = other DNA
                        organism = synthetic construct
CDS                     20..370
SEQUENCE: 1
ggcccagccg gccatggccc aggtccagct gcagcagtct ggacctgagc tggtgaaacc    60
tggggcttca gtgatgattt cctgcaaggc ttctggttac tcattcactg gctaccacat   120
gaactgggtg aagcaaagtc ctgaaaagag ccttgagtgg attggagaca taaatcctag   180
cattggtacg actgcccaca accagatttt cagggcaag gccacaatga ctgttgacaa   240
atcctccaac acagcctaca tgcagctcaa gagcctgaca tctgaagact ctggagtctt   300
ttactgtgtt agaagagggg actggtcctt cgatgtctgg ggcacaggga ccacggtcac   360
cgtctccagt                                                         370

SEQ ID NO: 2            moltype = AA  length = 117
FEATURE                 Location/Qualifiers
REGION                  1..117
                        note = Synthetic Construct
source                  1..117
                        mol_type = protein
                        organism = synthetic construct
SEQUENCE: 2
QVQLQQSGPE LVKPGASVMI SCKASGYSFT GYHMNWVKQS PEKSLEWIGD INPSIGTTAH    60
NQIFRAKATM TVDKSSNTAY MQLKSLTSED SGVFYCVRRG DWSFDVWGTG TTVTVSS      117

SEQ ID NO: 3            moltype = AA  length = 16
FEATURE                 Location/Qualifiers
REGION                  1..16
                        note = MF2926 CDR1
source                  1..16
                        mol_type = protein
                        organism = synthetic construct
SEQUENCE: 3
GYHMNWVKQS PEKSLE                                                    16

SEQ ID NO: 4            moltype = AA  length = 6
FEATURE                 Location/Qualifiers
```

```
REGION                    1..6
                          note = MF2926 CDR2
source                    1..6
                          mol_type = protein
                          organism = synthetic construct
SEQUENCE: 4
NQIFRA                                                                      6

SEQ ID NO: 5              moltype = AA  length = 8
FEATURE                   Location/Qualifiers
REGION                    1..8
                          note = MF2926 CDR3
source                    1..8
                          mol_type = protein
                          organism = synthetic construct
SEQUENCE: 5
RGDWSFDV                                                                    8

SEQ ID NO: 6              moltype = DNA  length = 379
FEATURE                   Location/Qualifiers
misc_feature              1..379
                          note = MF2930
source                    1..379
                          mol_type = other DNA
                          organism = synthetic construct
CDS                       20..379
SEQUENCE: 6
ggcccagccg gccatggccg aggtccagct gcagcagtct ggggctgaac tggtgaagcc        60
tggagcctca gtgatgatgt cctgtaaggt ttctggctac accttcactt cctatcctat       120
agcgtggatg aagcaggttc atggaaagag cctagaatgg attggaaatt ttcatcctta       180
cagtgatgat actaagtaca atgaaaactt caagggcaag gccacattga ctgtagaaaa       240
atcctctagc acagtctact tggagctcag ccgattaaca tctgatgact ctgctgttta       300
ttactgtgca agaagtaacc cattatatta ctttgctatg gactactggg gtcaaggaac       360
ctcggtcacc gtctccagt                                                    379

SEQ ID NO: 7              moltype = AA  length = 120
FEATURE                   Location/Qualifiers
REGION                    1..120
                          note = Synthetic Construct
source                    1..120
                          mol_type = protein
                          organism = synthetic construct
SEQUENCE: 7
EVQLQQSGAE LVKPGASVMM SCKVSGYTFT SYPIAWMKQV HGKSLEWIGN FHPYSDDTKY        60
NENFKGKATL TVEKSSSTVY LELSRLTSDD SAVYYCARSN PLYYFAMDYW GQGTSVTVSS       120

SEQ ID NO: 8              moltype = AA  length = 16
FEATURE                   Location/Qualifiers
REGION                    1..16
                          note = MF2930 CDR1
source                    1..16
                          mol_type = protein
                          organism = synthetic construct
SEQUENCE: 8
SYPIAWMKQV HGKSLE                                                         16

SEQ ID NO: 9              moltype = AA  length = 6
FEATURE                   Location/Qualifiers
REGION                    1..6
                          note = MF2930 CDR2
source                    1..6
                          mol_type = protein
                          organism = synthetic construct
SEQUENCE: 9
NENFKG                                                                      6

SEQ ID NO: 10             moltype = AA  length = 11
FEATURE                   Location/Qualifiers
REGION                    1..11
                          note = MF2930 CDR3
source                    1..11
                          mol_type = protein
                          organism = synthetic construct
SEQUENCE: 10
SNPLYYFAMD Y                                                               11

SEQ ID NO: 11             moltype = DNA  length = 385
FEATURE                   Location/Qualifiers
```

```
misc_feature            1..385
                        note = MF1849
source                  1..385
                        mol_type = other DNA
                        organism = synthetic construct
CDS                     20..385
SEQUENCE: 11
gcccagccg gccatggccc aggtgcagct ggtggagtct ggggggaggcg tggtccagcc    60
tgggaggtcc ctgagactct cctgtgcagc ctctggattc accttcagta gctatggcat   120
gcactgggtc cgccaggctc caggcaaggg gctggagtgg gtggcagtta tatcatatga   180
tggaagtaat aaatactatg cagactccgt gaagggccga ttcaccatct ccagagacaa   240
ttccaagaac acgctgtatc tgcaaatgaa cagcctgaga gctgaggaca cggccgtgta   300
ttactgtgca aaaggtgact acggttctta ctcttcttac gcctttgatt attggggcca   360
aggtaccctg gtcaccgtct ccagt                                         385

SEQ ID NO: 12           moltype = AA  length = 122
FEATURE                 Location/Qualifiers
REGION                  1..122
                        note = Synthetic Construct
source                  1..122
                        mol_type = protein
                        organism = synthetic construct
SEQUENCE: 12
QVQLVESGGG VVQPGRSLRL SCAASGFTFS SYGMHWVRQA PGKGLEWVAV ISYDGSNKYY    60
ADSVKGRFTI SRDNSKNTLY LQMNSLRAED TAVYYCAKGD YGSYSSYAFD YWGQGTLVTV   120
SS                                                                  122

SEQ ID NO: 13           moltype = AA  length = 5
FEATURE                 Location/Qualifiers
REGION                  1..5
                        note = MF1849 CDR1
source                  1..5
                        mol_type = protein
                        organism = synthetic construct
SEQUENCE: 13
SYGMH                                                                 5

SEQ ID NO: 14           moltype = AA  length = 17
FEATURE                 Location/Qualifiers
REGION                  1..17
                        note = MF1849 CDR2
source                  1..17
                        mol_type = protein
                        organism = synthetic construct
SEQUENCE: 14
VISYDGSNKY YADSVKG                                                   17

SEQ ID NO: 15           moltype = AA  length = 13
FEATURE                 Location/Qualifiers
REGION                  1..13
                        note = MF1849 CDR3
source                  1..13
                        mol_type = protein
                        organism = synthetic construct
SEQUENCE: 15
GDYGSYSSYA FDY                                                       13

SEQ ID NO: 16           moltype = DNA  length = 385
FEATURE                 Location/Qualifiers
misc_feature            1..385
                        note = MF2973
source                  1..385
                        mol_type = other DNA
                        organism = synthetic construct
CDS                     20..385
SEQUENCE: 16
gcccagccg gccatggccc aggtgcagct gaagcagtct ggggctgagc tggtgaggcc    60
tggggcttca gtgaagttgt cctgcaaggc ttctggctac attttcactg gctactatat   120
aaactggttg aggcagaggc ctggacaggg acttgaatgg attgcaaaaa tttatcctgg   180
aagtggtaat acttactaca tgagaagttt caggggcaag gccacactga ctgcagaaga   240
atcctccagc actgcctaca tgcagctcag cagcctgaca tctgaggact ctgctgtcta   300
tttctgtgca agagggcccc actatgatta cgacggcccc tggtttgttt actggggcca   360
agggactctg gtcaccgtct ccagt                                         385

SEQ ID NO: 17           moltype = AA  length = 122
FEATURE                 Location/Qualifiers
REGION                  1..122
                        note = Synthetic Construct
```

```
source                  1..122
                        mol_type = protein
                        organism = synthetic construct
SEQUENCE: 17
QVQLKQSGAE LVRPGASVKL SCKASGYIFT GYYINWLRQR PGQGLEWIAK IYPGSGNTYY    60
NEKFRGKATL TAEESSSTAY MQLSSLTSED SAVYFCARGP HYDYDGPWFV YWGQGTLVTV   120
SS                                                                 122

SEQ ID NO: 18           moltype = AA  length = 16
FEATURE                 Location/Qualifiers
REGION                  1..16
                        note = MF2973 CDR1
source                  1..16
                        mol_type = protein
                        organism = synthetic construct
SEQUENCE: 18
GYYINWLRQR PGQGLE                                                   16

SEQ ID NO: 19           moltype = AA  length = 6
FEATURE                 Location/Qualifiers
REGION                  1..6
                        note = MF2973 CDR2
source                  1..6
                        mol_type = protein
                        organism = synthetic construct
SEQUENCE: 19
NEKFRG                                                               6

SEQ ID NO: 20           moltype = AA  length = 13
FEATURE                 Location/Qualifiers
REGION                  1..13
                        note = MF2973 CDR3
source                  1..13
                        mol_type = protein
                        organism = synthetic construct
SEQUENCE: 20
GPHYDYDGPW FVY                                                      13

SEQ ID NO: 21           moltype = DNA  length = 382
FEATURE                 Location/Qualifiers
misc_feature            1..382
                        note = MF3004
source                  1..382
                        mol_type = other DNA
                        organism = synthetic construct
CDS                     20..382
SEQUENCE: 21
ggcccagccg gccatggccc aggtgcagct gaagcagtct ggggctgagc tggtgaggcc    60
tggggcttca gtgaagctgt cctgcaaggc ttctggctac actttcactg gctactatat   120
aaactgggtg aagcagaggc ctggacaggg acttgagtgg attgcaagga tttatcctgg   180
aagtggttat acttactaca tgagaagtt caagggcaag gccacactga ctgcagaaga   240
atccctccag cactgcctac atgcacctcag cagcctgaca tctgaggact ctgctgtcta   300
tttctgtgca agaccccact atggttacga cgactggtac ttcggtgtct ggggcacagg   360
caccacggtc accgtctcca gt                                           382

SEQ ID NO: 22           moltype = AA  length = 121
FEATURE                 Location/Qualifiers
REGION                  1..121
                        note = Synthetic Construct
source                  1..121
                        mol_type = protein
                        organism = synthetic construct
SEQUENCE: 22
QVQLKQSGAE LVRPGASVKL SCKASGYTFT GYYINWVKQR PGQGLEWIAR IYPGSGYTYY    60
NEKFKGKATL TAEESSSTAY MHLSSLTSED SAVYFCARPH YGYDDWYFGV WGTGTTVTVS   120
S                                                                  121

SEQ ID NO: 23           moltype = AA  length = 16
FEATURE                 Location/Qualifiers
REGION                  1..16
                        note = MF3004 CDR1
source                  1..16
                        mol_type = protein
                        organism = synthetic construct
SEQUENCE: 23
GYYINWVKQR PGQGLE                                                   16

SEQ ID NO: 24           moltype = AA  length = 6
FEATURE                 Location/Qualifiers
```

-continued

```
REGION                  1..6
                        note = MF3004 CDR2
source                  1..6
                        mol_type = protein
                        organism = synthetic construct
SEQUENCE: 24
NEKFKG                                                                      6

SEQ ID NO: 25           moltype = AA  length = 12
FEATURE                 Location/Qualifiers
REGION                  1..12
                        note = MF3004 CDR3
source                  1..12
                        mol_type = protein
                        organism = synthetic construct
SEQUENCE: 25
PHYGYDDWYF GV                                                              12

SEQ ID NO: 26           moltype = DNA  length = 382
FEATURE                 Location/Qualifiers
misc_feature            1..382
                        note = MF2971
source                  1..382
                        mol_type = other DNA
                        organism = synthetic construct
SEQUENCE: 26
ggcccagccg gccatggccc aggtgcagct gaagcagtct ggggctgagc tggtgaggcc          60
tggggcttca gtgaaactgt cctgcaaggc ttctggctac actttcactg cctactatat         120
aaactgggtg aagcagaggc ctggacaggg acttgagtgg attgcaagga tttatcctgg         180
aagtggctat acttactaca tgagattttt caagggcagg gccacactga ctgcagacga         240
atcctccagc actgcctaca tgcaactcag cagcctgaca tctgaggact ctgctgtcta         300
tttctgtgca agacctccgg tctactatga ctcggcctgg tttgcttact ggggccaagg         360
gactctggtc accgtctcca gt                                                  382

SEQ ID NO: 27           moltype = AA  length = 16
FEATURE                 Location/Qualifiers
REGION                  1..16
                        note = MF2971 CDR1
source                  1..16
                        mol_type = protein
                        organism = synthetic construct
SEQUENCE: 27
AYYINWVKQR PGQGLE                                                          16

SEQ ID NO: 28           moltype = AA  length = 6
FEATURE                 Location/Qualifiers
REGION                  1..6
                        note = MF2971 CDR2
source                  1..6
                        mol_type = protein
                        organism = synthetic construct
SEQUENCE: 28
NEIFKG                                                                      6

SEQ ID NO: 29           moltype = AA  length = 12
FEATURE                 Location/Qualifiers
REGION                  1..12
                        note = MF2971 CDR3
source                  1..12
                        mol_type = protein
                        organism = synthetic construct
SEQUENCE: 29
PPVYYDSAWF AY                                                              12

SEQ ID NO: 30           moltype = DNA  length = 382
FEATURE                 Location/Qualifiers
misc_feature            1..382
                        note = MF3025
source                  1..382
                        mol_type = other DNA
                        organism = synthetic construct
CDS                     20..382
SEQUENCE: 30
ggcccagccg gccatggccc aggtgcagct gaagcagtct ggggctgagc tggtgaggcc          60
tggggacttca gtgaagctgt cctgcaaggc ttctggctac actttcactg gctactatat        120
aaactgggtg aagcagaggc ctggacaggg acttgagtgg attgcaagga tttatcctgg         180
aagtggttat acttactaca tgagaagtt caagggcaag gccacactga ctgcagaaga          240
```

```
atcctccaac actgcctata tgcacctcag cagcctgaca tctgaggact ctgctgtcta    300
tttctgtgca aggccccact atggttacga cgactggtac ttcgctgtct ggggcacagg    360
gaccacggtc accgtctcca gt                                             382
```

```
SEQ ID NO: 31            moltype = AA   length = 121
FEATURE                  Location/Qualifiers
REGION                   1..121
                         note = Synthetic Construct
source                   1..121
                         mol_type = protein
                         organism = synthetic construct
SEQUENCE: 31
QVQLKQSGAE LVRPGTSVKL SCKASGYTFT GYYINWVKQR PGQGLEWIAR IYPGSGYTYY    60
NEKFKGKATL TAEESSNTAY MHLSSLTSED SAVYFCARPH YGYDDWYFAV WGTGTTVTVS    120
S                                                                    121

SEQ ID NO: 32            moltype = AA   length = 16
FEATURE                  Location/Qualifiers
REGION                   1..16
                         note = MF3025 CDR1
source                   1..16
                         mol_type = protein
                         organism = synthetic construct
SEQUENCE: 32
GYYINWVKQR PGQGLE                                                     16

SEQ ID NO: 33            moltype = AA   length = 6
FEATURE                  Location/Qualifiers
REGION                   1..6
                         note = MF3025 CDR2
source                   1..6
                         mol_type = protein
                         organism = synthetic construct
SEQUENCE: 33
NEKFKG                                                                6

SEQ ID NO: 34            moltype = AA   length = 12
FEATURE                  Location/Qualifiers
REGION                   1..12
                         note = MF3025 CDR3
source                   1..12
                         mol_type = protein
                         organism = synthetic construct
SEQUENCE: 34
PHYGYDDWYF AV                                                         12

SEQ ID NO: 35            moltype = DNA   length = 385
FEATURE                  Location/Qualifiers
misc_feature             1..385
                         note = MF2916
source                   1..385
                         mol_type = other DNA
                         organism = synthetic construct
CDS                      20..385
SEQUENCE: 35
ggcccagccg ccatggccc aggtccagct gcagcagtct ggggctgagc tggtgaggcc     60
tggggcttca gtgaagctgt cctgcaaggc ttctggctac actttcactg gctactatat    120
aaactgggtg aagcagaggc ctggacaggg acttgagtgg attgcaagga tttatcctgg    180
cagtggtcat acttcctaca tgagaagtt caagggcaag gccacactga ctacagaaaa    240
atcctccagc actgcctaca tgcagctcag cagcctgaca tctgaggact ctgctgtcta    300
tttctgtgca agacctatct actttgatta cgcaggggga tacttcgatg tctggggcac    360
aagaaccctcg gtcaccgtct ccagt                                         385

SEQ ID NO: 36            moltype = AA   length = 122
FEATURE                  Location/Qualifiers
REGION                   1..122
                         note = Synthetic Construct
source                   1..122
                         mol_type = protein
                         organism = synthetic construct
SEQUENCE: 36
QVQLQQSGAE LVRPGASVKL SCKASGYTFT GYYINWVKQR PGQGLEWIAR IYPGSGHTSY    60
NEKFKGKATL TTEKSSSTAY MQLSSLTSED SAVYFCARPI YFDYAGGYFD VWGTRTSVTV    120
SS                                                                   122

SEQ ID NO: 37            moltype = AA   length = 13
FEATURE                  Location/Qualifiers
REGION                   1..13
                         note = MF2916 CDR3
```

```
source                      1..13
                            mol_type = protein
                            organism = synthetic construct
SEQUENCE: 37
PIYFDYAGGY FDV                                                                    13

SEQ ID NO: 38               moltype = DNA   length = 382
FEATURE                     Location/Qualifiers
misc_feature                1..382
                            note = MF3958
source                      1..382
                            mol_type = other DNA
                            organism = synthetic construct
CDS                         20..382
SEQUENCE: 38
ggcccagccg gccatggccc aggtgcagct ggtgcagtct ggcgccgaag tgaagaaacc    60
tggcgccagc gtgaagctga gctgcaaggc cagcggctac accttcaccg cctactacat   120
caactgggtc cgacaggccc caggccaggg cctggaatgg atcggcagaa tctaccccgg   180
ctccggctac accagctacg cccagaagtt ccagggcaga gccaccctga ccgccgacga   240
gagcaccagc accgcctaca tggaactgag cagcctgcgg agcgaggata ccgccgtgta   300
cttctgcgcc agaccccccg tgtactacga cagcgcttgg tttgcctact ggggccaggg   360
caccctggtc accgtctcca gt                                            382

SEQ ID NO: 39               moltype = AA   length = 121
FEATURE                     Location/Qualifiers
REGION                      1..121
                            note = Synthetic Construct
source                      1..121
                            mol_type = protein
                            organism = synthetic construct
SEQUENCE: 39
QVQLVQSGAE VKKPGASVKL SCKASGYTFT AYYINWVRQA PGQGLEWIGR IYPGSGYTSY    60
AQKFQGRATL TADESTSTAY MELSSLRSED TAVYFCARPP VYYDSAWFAY WGQGTLVTVS   120
S                                                                   121

SEQ ID NO: 40               moltype = AA   length = 5
FEATURE                     Location/Qualifiers
REGION                      1..5
                            note = MF3958 CDR1
source                      1..5
                            mol_type = protein
                            organism = synthetic construct
SEQUENCE: 40
AYYIN                                                                              5

SEQ ID NO: 41               moltype = AA   length = 17
FEATURE                     Location/Qualifiers
REGION                      1..17
                            note = MF3958 CDR2
source                      1..17
                            mol_type = protein
                            organism = synthetic construct
SEQUENCE: 41
RIYPGSGYTS YAQKFQG                                                                17

SEQ ID NO: 42               moltype = AA   length = 12
FEATURE                     Location/Qualifiers
REGION                      1..12
                            note = MF3958 CDR3
source                      1..12
                            mol_type = protein
                            organism = synthetic construct
SEQUENCE: 42
PPVYYDSAWF AY                                                                     12

SEQ ID NO: 43               moltype = DNA   length = 382
FEATURE                     Location/Qualifiers
misc_feature                1..382
                            note = MF3031
source                      1..382
                            mol_type = other DNA
                            organism = synthetic construct
SEQUENCE: 43
ggcccagccg gccatggccc aggtccagct gcagcagtct ggggctgagc tggtgaggcc    60
tggggcttca gtgaagctgt cctgcaaggc ttctggctac actttcactg cctactatat   120
aaactgggtg aagcagaggc ctggacaggg acttgagtgg attgcaaaga tttatcctgg   180
aagtggttat acttactaca atgagaattt caggggcaag gccacactga ctgcagaaga   240
atcctccagt actgcctaca tacaactcag cagcctgaca tctgaggact ctgctgtcta   300
```

```
tttctgtgca agaggcgtct atgattacga cggggcctgg tttgcttact ggggccaagg   360
gactctggtc accgtctcca gt                                            382
```

SEQ ID NO: 44          moltype = AA  length = 16
FEATURE                Location/Qualifiers
REGION                 1..16
                       note = MF3031 CDR1
source                 1..16
                       mol_type = protein
                       organism = synthetic construct
SEQUENCE: 44
AYYINWVKQR PGQGLE                                                   16

SEQ ID NO: 45          moltype = AA  length = 6
FEATURE                Location/Qualifiers
REGION                 1..6
                       note = MF3031 CDR2
source                 1..6
                       mol_type = protein
                       organism = synthetic construct
SEQUENCE: 45
NENFRG                                                              6

SEQ ID NO: 46          moltype = AA  length = 12
FEATURE                Location/Qualifiers
REGION                 1..12
                       note = MF3031 CDR3
source                 1..12
                       mol_type = protein
                       organism = synthetic construct
SEQUENCE: 46
GVYDYDGAWF AY                                                       12

SEQ ID NO: 47          moltype = DNA  length = 382
FEATURE                Location/Qualifiers
misc_feature           1..382
                       note = MF3991
source                 1..382
                       mol_type = other DNA
                       organism = synthetic construct
CDS                    20..382
SEQUENCE: 47
```
ggcccagccg gccatggccc aggtgcagct ggtgcagtct ggcgccgaag tgaagaaacc   60
tggcgccagc gtgaagctga gctgcaaggc cagcggctac accttcaccg cctactacat   120
caactgggtc cgacaggccc caggccaggg cctggaatgg atcggcagaa tctacccccgg  180
ctccggctac accagctacg cccagaagtt ccagggcaga gccaccctga ccgccgacga   240
gagcaccagc acctacatgg aactgagcag cctgcgg agaggata ccgccgtgta        300
cttctgcgcc agacccccact acggctacga cgactggtac ttcggcgtgt ggggccaggg  360
caccctggtc accgtctcca gt                                            382
```

SEQ ID NO: 48          moltype = AA  length = 121
FEATURE                Location/Qualifiers
REGION                 1..121
                       note = Synthetic Construct
source                 1..121
                       mol_type = protein
                       organism = synthetic construct
SEQUENCE: 48
QVQLVQSGAE VKKPGASVKL SCKASGYTFT AYYINWVRQA PGQGLEWIGR IYPGSGYTSY   60
AQKFQGRATL TADESTSTAY MELSSLRSED TAVYFCARPH YGYDDWYFGV WGQGTLVTVS   120
S                                                                   121

SEQ ID NO: 49          moltype = AA  length = 5
FEATURE                Location/Qualifiers
REGION                 1..5
                       note = MF3991 CDR1
source                 1..5
                       mol_type = protein
                       organism = synthetic construct
SEQUENCE: 49
AYYIN                                                               5

SEQ ID NO: 50          moltype = AA  length = 17
FEATURE                Location/Qualifiers
REGION                 1..17
                       note = MF3991 CDR2
source                 1..17
                       mol_type = protein
                       organism = synthetic construct

```
SEQUENCE: 50
RIYPGSGYTS YAQKFQG                                                         17

SEQ ID NO: 51           moltype = AA  length = 12
FEATURE                 Location/Qualifiers
REGION                  1..12
                        note = MF3991 CDR3
source                  1..12
                        mol_type = protein
                        organism = synthetic construct
SEQUENCE: 51
PHYGYDDWYF GV                                                              12

SEQ ID NO: 52           moltype = DNA  length = 391
FEATURE                 Location/Qualifiers
misc_feature            1..391
                        note = MF3178
source                  1..391
                        mol_type = other DNA
                        organism = synthetic construct
CDS                     20..391
SEQUENCE: 52
ggcccagccg gccatggccc aggtgcagct ggtgcagtct ggggctgagg tgaagaagcc          60
tggggcctca gtgaaggtct cctgcaaggc ttctggatac accttcaccg gctactatat         120
gcactgggtg cgacaggccc ctggacaagg gcttgagtgg atgggatgga tcaaccctaa         180
cagtggtggc acaaactatg cacagaagtt tcagggcagg gtcacgatga ccagggacac         240
gtccatcagc acagcctaca tggagctgag caggctgaga tctgacgaca cggctgtgta         300
ttactgtgca agagatcatg gttctcgtca tttctggtct tactggggct tgattattg          360
gggccaaggt accctggtca ccgtctccag t                                         391

SEQ ID NO: 53           moltype = AA  length = 124
FEATURE                 Location/Qualifiers
REGION                  1..124
                        note = Synthetic Construct
source                  1..124
                        mol_type = protein
                        organism = synthetic construct
SEQUENCE: 53
QVQLVQSGAE VKKPGASVKV SCKASGYTFT GYYMHWVRQA PGQGLEWMGW INPNSGGTNY           60
AQKFQGRVTM TRDTSISTAY MELSRLRSDD TAVYYCARDH GSRHFWSYWG FDYWGQGTLV          120
TVSS                                                                      124

SEQ ID NO: 54           moltype = AA  length = 5
FEATURE                 Location/Qualifiers
REGION                  1..5
                        note = MF3178 CDR1
source                  1..5
                        mol_type = protein
                        organism = synthetic construct
SEQUENCE: 54
GYYMH                                                                       5

SEQ ID NO: 55           moltype = AA  length = 17
FEATURE                 Location/Qualifiers
REGION                  1..17
                        note = MF3178 CDR2
source                  1..17
                        mol_type = protein
                        organism = synthetic construct
SEQUENCE: 55
WINPNSGGTN YAQKFQG                                                         17

SEQ ID NO: 56           moltype = AA  length = 15
FEATURE                 Location/Qualifiers
REGION                  1..15
                        note = MF3178 CDR3
source                  1..15
                        mol_type = protein
                        organism = synthetic construct
SEQUENCE: 56
DHGSRHFWSY WGFDY                                                           15

SEQ ID NO: 57           moltype = DNA  length = 385
FEATURE                 Location/Qualifiers
misc_feature            1..385
                        note = MF3176
source                  1..385
                        mol_type = other DNA
                        organism = synthetic construct
```

| | | |
|---|---|---|
| CDS | 20..385 | |
| SEQUENCE: 57 | | |
| ggcccagccg gccatggccg aggtgcagct gttggagtct ggggggaggct tggtacagcc | | 60 |
| tggggggtcc ctgagactct cctgtgcagc ctctggattc acctttagca gctatgccat | | 120 |
| gagctgggtc cgccaggctc cagggaaggg gctggagtgg gtctcagcta ttagtggtag | | 180 |
| tggtggtagc acatactacg cagactccgt gaagggccgg ttcaccatct ccagagacaa | | 240 |
| ttccaagaac acgctgtatc tgcaaatgaa cagcctgaga gccgaggaca cggctgtgta | | 300 |
| ttactgtgca agagattggt ggtacccgcc gtactactgg ggctttgatt attggggcca | | 360 |
| aggtaccctg gtcaccgtct ccagt | | 385 |
| | | |
| SEQ ID NO: 58 | moltype = AA length = 122 | |
| FEATURE | Location/Qualifiers | |
| REGION | 1..122 | |
| | note = Synthetic Construct | |
| source | 1..122 | |
| | mol_type = protein | |
| | organism = synthetic construct | |
| SEQUENCE: 58 | | |
| EVQLLESGGG LVQPGGSLRL SCAASGFTFS SYAMSWVRQA PGKGLEWVSA ISGSGGSTYY | | 60 |
| ADSVKGRFTI SRDNSKNTLY LQMNSLRAED TAVYYCARDW WYPPYYWGFD YWGQGTLVTV | | 120 |
| SS | | 122 |
| | | |
| SEQ ID NO: 59 | moltype = AA length = 5 | |
| FEATURE | Location/Qualifiers | |
| REGION | 1..5 | |
| | note = MF3176 CDR1 | |
| source | 1..5 | |
| | mol_type = protein | |
| | organism = synthetic construct | |
| SEQUENCE: 59 | | |
| SYAMS | | 5 |
| | | |
| SEQ ID NO: 60 | moltype = AA length = 17 | |
| FEATURE | Location/Qualifiers | |
| REGION | 1..17 | |
| | note = MF3176 CDR2 | |
| source | 1..17 | |
| | mol_type = protein | |
| | organism = synthetic construct | |
| SEQUENCE: 60 | | |
| AISGSGGSTY YADSVKG | | 17 |
| | | |
| SEQ ID NO: 61 | moltype = AA length = 13 | |
| FEATURE | Location/Qualifiers | |
| REGION | 1..13 | |
| | note = MF3176 CDR3 | |
| source | 1..13 | |
| | mol_type = protein | |
| | organism = synthetic construct | |
| SEQUENCE: 61 | | |
| DWWYPPYYWG FDY | | 13 |
| | | |
| SEQ ID NO: 62 | moltype = DNA length = 391 | |
| FEATURE | Location/Qualifiers | |
| misc_feature | 1..391 | |
| | note = MF3163 | |
| source | 1..391 | |
| | mol_type = other DNA | |
| | organism = synthetic construct | |
| SEQUENCE: 62 | | |
| ggcccagccg gccatggccc aggtgcagct ggtgcagtct ggggctgagg tgaagaagcc | | 60 |
| tggggcctca gtgaaggtct cctgcaaggc ttctggatac accttcaccg gctactatat | | 120 |
| gcactgggtg cgacaggccc ctggacaagg gcttgagtgg atgggatgga tcaacccta a | | 180 |
| cagtggtggc acaaactatg cacagaagtt tcagggcagg gtcacgatga ccagggacac | | 240 |
| gtccatcagc acagcctaca tggagctgag caggctgaga tctgacgaca cggccgtgta | | 300 |
| ttactgtgca aaagattctt actctcgtca tttctactct tggtgggcct tgattattg g | | 360 |
| gggccaaggt accctggtca ccgtctccag t | | 391 |
| | | |
| SEQ ID NO: 63 | moltype = AA length = 17 | |
| FEATURE | Location/Qualifiers | |
| REGION | 1..17 | |
| | note = MF3163 CDR2 | |
| source | 1..17 | |
| | mol_type = protein | |
| | organism = synthetic construct | |
| SEQUENCE: 63 | | |
| WINPNSGGTN YAQKFQG | | 17 |
| | | |
| SEQ ID NO: 64 | moltype = AA length = 15 | |

```
FEATURE                 Location/Qualifiers
REGION                  1..15
                        note = MF3163 CDR3
source                  1..15
                        mol_type = protein
                        organism = synthetic construct
SEQUENCE: 64
DSYSRHFYSW WAFDY                                                          15

SEQ ID NO: 65           moltype = DNA  length = 382
FEATURE                 Location/Qualifiers
misc_feature            1..382
                        note = MF3099
source                  1..382
                        mol_type = other DNA
                        organism = synthetic construct
CDS                     20..382
SEQUENCE: 65
ggcccagccg gccatggccg aggtccagct gcagcagcct ggggctgagc tggtgaggcc          60
tgggacttca gtgaagttgt cctgcaaggc ttctggctac accttcacca gctactggat        120
gcactgggta aagcagaggc ctggacaagg ccttgagtgg atcggaattc ttgatccttc        180
tgatagttat actacctaca atcaaaagtt caagggcaag gccacattaa cagtagacac        240
atcctccagc atagcctaca tgcagctcag cagcctgaca tctgaggact ctgcgctcta        300
ttactgtgca agagggggag attacgacga gggaggtgct atggactact ggggtcaagg        360
aacctcggtc accgtctcca gt                                                 382

SEQ ID NO: 66           moltype = AA  length = 121
FEATURE                 Location/Qualifiers
REGION                  1..121
                        note = Synthetic Construct
source                  1..121
                        mol_type = protein
                        organism = synthetic construct
SEQUENCE: 66
EVQLQQPGAE LVRPGTSVKL SCKASGYTFT SYWMHWVKQR PGQGLEWIGI LDPSDSYTTY          60
NQKFKGKATL TVDTSSSIAY MQLSSLTSED SALYYCARGG DYDEGGAMDY WGQGTSVTVS        120
S                                                                       121

SEQ ID NO: 67           moltype = AA  length = 5
FEATURE                 Location/Qualifiers
REGION                  1..5
                        note = MF3099 CDR1
source                  1..5
                        mol_type = protein
                        organism = synthetic construct
SEQUENCE: 67
SYWMH                                                                      5

SEQ ID NO: 68           moltype = AA  length = 17
FEATURE                 Location/Qualifiers
REGION                  1..17
                        note = MF3099 CDR2
source                  1..17
                        mol_type = protein
                        organism = synthetic construct
SEQUENCE: 68
ILDPSDSYTT YNQKFKG                                                        17

SEQ ID NO: 69           moltype = AA  length = 12
FEATURE                 Location/Qualifiers
REGION                  1..12
                        note = MF3099 CDR3
source                  1..12
                        mol_type = protein
                        organism = synthetic construct
SEQUENCE: 69
GGDYDEGGAM DY                                                             12

SEQ ID NO: 70           moltype = DNA  length = 391
FEATURE                 Location/Qualifiers
misc_feature            1..391
                        note = MF3307
source                  1..391
                        mol_type = other DNA
                        organism = synthetic construct
CDS                     20..391
SEQUENCE: 70
ggcccagccg gccatggccc aggtgcagct ggtgcagtct ggggctgagg tgaagaagcc          60
tggggcctca gtgaaggtct cctgcaaggc ttctggatac accttcaccg gctactatat        120
```

```
gcactgggtg cgacaggccc ctggacaagg gcttgagtgg atgggatgga tcaaccctaa    180
cagtggtggc acaaactatg cacagaagtt tcagggcagg gtcacgatga ccagggacac    240
gtccatcagc acagcctaca tggagctgag caggctgaga tctgacgaca cggccgtgta    300
ttactgtgca agaggttctc gtaaacgtct gtctaactac ttcaacgcct ttgattattg    360
gggccaaggt accctggtca ccgtctccag t                                   391

SEQ ID NO: 71          moltype = AA   length = 124
FEATURE                Location/Qualifiers
REGION                 1..124
                       note = Synthetic Construct
source                 1..124
                       mol_type = protein
                       organism = synthetic construct
SEQUENCE: 71
QVQLVQSGAE VKKPGASVKV SCKASGYTFT GYYMHWVRQA PGQGLEWMGW INPNSGGTNY     60
AQKFQGRVTM TRDTSISTAY MELSRLRSDD TAVYYCARGS RKRLSNYFNA FDYWGQGTLV    120
TVSS                                                                 124

SEQ ID NO: 72          moltype = AA   length = 17
FEATURE                Location/Qualifiers
REGION                 1..17
                       note = MF3307 CDR2
source                 1..17
                       mol_type = protein
                       organism = synthetic construct
SEQUENCE: 72
WINPNSGGTN YAQKFQG                                                    17

SEQ ID NO: 73          moltype = AA   length = 15
FEATURE                Location/Qualifiers
REGION                 1..15
                       note = MF3307 CDR3
source                 1..15
                       mol_type = protein
                       organism = synthetic construct
SEQUENCE: 73
GSRKRLSNYF NAFDY                                                      15

SEQ ID NO: 74          moltype = AA   length = 95
FEATURE                Location/Qualifiers
REGION                 1..95
                       note = variable region of IGKV1-39
source                 1..95
                       mol_type = protein
                       organism = synthetic construct
SEQUENCE: 74
DIQMTQSPSS LSASVGDRVT ITCRASQSIS SYLNWYQQKP GKAPKLLIYA ASSLQSGVPS     60
RFSGSGSGTD FTLTISSLQP EDFATYYCQQ SYSTP                                95

SEQ ID NO: 75          moltype = AA   length = 11
FEATURE                Location/Qualifiers
REGION                 1..11
                       note = IGKV1-39 CDR1
source                 1..11
                       mol_type = protein
                       organism = synthetic construct
SEQUENCE: 75
RASQSISSYL N                                                          11

SEQ ID NO: 76          moltype = AA   length = 7
FEATURE                Location/Qualifiers
REGION                 1..7
                       note = IGKV1-39 CDR2
source                 1..7
                       mol_type = protein
                       organism = synthetic construct
SEQUENCE: 76
AASSLQS                                                                7

SEQ ID NO: 77          moltype = AA   length = 9
FEATURE                Location/Qualifiers
REGION                 1..9
                       note = IGKV1-39 CDR3
source                 1..9
                       mol_type = protein
                       organism = synthetic construct
SEQUENCE: 77
QQSYSTPPT                                                              9
```

```
SEQ ID NO: 78              moltype = AA   length = 107
FEATURE                    Location/Qualifiers
REGION                     1..107
                           note = IGKV1-39/jk1
source                     1..107
                           mol_type = protein
                           organism = synthetic construct
SEQUENCE: 78
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPTFGQ GTKVEIK                 107

SEQ ID NO: 79              moltype = AA   length = 214
FEATURE                    Location/Qualifiers
REGION                     1..214
                           note = IGKV1-39/jk1 common light chain
source                     1..214
                           mol_type = protein
                           organism = synthetic construct
SEQUENCE: 79
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 80              moltype = AA   length = 108
FEATURE                    Location/Qualifiers
REGION                     1..108
                           note = IGKV1-39/jk5
source                     1..108
                           mol_type = protein
                           organism = synthetic construct
SEQUENCE: 80
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPITFG QGTRLEIK                108

SEQ ID NO: 81              moltype = AA   length = 450
FEATURE                    Location/Qualifiers
REGION                     1..450
                           note = heavy chain for erbB-2 binding
source                     1..450
                           mol_type = protein
                           organism = synthetic construct
SEQUENCE: 81
QVQLVQSGAE VKKPGASVKL SCKASGYTFT AYYINWVRQA PGQGLEWIGR IYPGSGYTSY    60
AQKFQGRATL TADESTSTAY MELSSLRSED TAVYFCARPP VYYDSAWFAY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTDPPSRE   360
EMTKNQVSLT CEVKGFYPSD IAVEWESNGQ PENNYKTTPP VLDSDGSFFL YSKLTVDKSR   420
WQQGNVFSCS VMHEALHNHY TQKSLSLSPG                                   450

SEQ ID NO: 82              moltype = AA   length = 453
FEATURE                    Location/Qualifiers
REGION                     1..453
                           note = heavy chain for erbB-3 binding
source                     1..453
                           mol_type = protein
                           organism = synthetic construct
SEQUENCE: 82
QVQLVQSGAE VKKPGASVKV SCKASGYTFT GYYMHWVRQA PGQGLEWMGW INPNSGGTNY    60
AQKFQGRVTM TRDTSISTAY MELSRLRSDD TAVYYCARDH GSRHFWSYWG FDYWGQGTLV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK RVEPKSCDKT HTCPPCPAPE   240
LLGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTKPP   360
SREEMTKNQV SLKCLVKGFY PSDIAVEWES NGQPENNYKT TPPVLDSDGS FFLYSKLTVD   420
KSRWQQGNVF SCSVMHEALH NHYTQKSLSL SPG                               453

SEQ ID NO: 83              moltype = DNA  length = 379
FEATURE                    Location/Qualifiers
misc_feature               1..379
                           note = MF2889
source                     1..379
                           mol_type = other DNA
                           organism = synthetic construct
CDS                        20..379
```

```
SEQUENCE: 83
ggcccagccg gccatggccg aggtccagct gcagcagtct ggagctgagc tggtaaggcc         60
tgggacttca gtgaaggtgt cctgcaaggc ttctggatac gccttcacta attatttgat        120
agagtgggta aagcagaggc ctggccaggg ccttgagtgg attggagtga tttatcctga        180
aggtggtggt actatctaca atgagaagtt caagggcaag gcaacactga ctgcagacaa        240
atcctccagc actgcctaca tgcagctcag cggcctgaca tctgaggact ctgcggtcta        300
tttctgtgca agaggagact atgattacaa atatgctatg gactactggg gtcaaggaac        360
ctcggtcacc gtctccagt                                                     379

SEQ ID NO: 84           moltype = AA  length = 120
FEATURE                 Location/Qualifiers
REGION                  1..120
                        note = Synthetic Construct
source                  1..120
                        mol_type = protein
                        organism = synthetic construct
SEQUENCE: 84
EVQLQQSGAE LVRPGTSVKV SCKASGYAFT NYLIEWVKQR PGQGLEWIGV IYPEGGGTIY          60
NEKFKGKATL TADKSSSTAY MQLSGLTSED SAVYFCARGD YDYKYAMDYW GQGTSVTVSS         120

SEQ ID NO: 85           moltype = AA  length = 5
FEATURE                 Location/Qualifiers
REGION                  1..5
                        note = MF2889 CDR1
source                  1..5
                        mol_type = protein
                        organism = synthetic construct
SEQUENCE: 85
NYLIE                                                                      5

SEQ ID NO: 86           moltype = AA  length = 17
FEATURE                 Location/Qualifiers
REGION                  1..17
                        note = MF2889 CDR2
source                  1..17
                        mol_type = protein
                        organism = synthetic construct
SEQUENCE: 86
VIYPEGGGTI YNEKFKG                                                        17

SEQ ID NO: 87           moltype = AA  length = 11
FEATURE                 Location/Qualifiers
REGION                  1..11
                        note = MF2889 CDR3
source                  1..11
                        mol_type = protein
                        organism = synthetic construct
SEQUENCE: 87
GDYDYKYAMD Y                                                              11

SEQ ID NO: 88           moltype = DNA  length = 370
FEATURE                 Location/Qualifiers
misc_feature            1..370
                        note = MF2913
source                  1..370
                        mol_type = other DNA
                        organism = synthetic construct
CDS                     20..370
SEQUENCE: 88
ggcccagccg gccatggccg aggtcaagct gcagcagtct ggacctgagc tggtgaagcc         60
tggcgcttca gtgaagatat cctgcaaggc ttctggttac tcattcactg actacaaaat        120
ggactgggtg aagcagagcc atggaaagag cctcgaatgg attggaaata ttaatcctaa        180
cagtggtggt gttatctaca accagaagtt caggggcaag gtcacattga ctgttgacag        240
gtcctccagc gcagcctaca tggagctccg cagcctgaca tctgaggaca ctgcagtcta        300
ttattgttca agaggactgt gggatgctat ggactcctgg ggtcaaggaa cctcggtcac        360
cgtctccagt                                                               370

SEQ ID NO: 89           moltype = AA  length = 117
FEATURE                 Location/Qualifiers
REGION                  1..117
                        note = Synthetic Construct
source                  1..117
                        mol_type = protein
                        organism = synthetic construct
SEQUENCE: 89
EVKLQQSGPE LVKPGASVKI SCKASGYSFT DYKMDWVKQS HGKSLEWIGN INPNSGGVIY          60
NQKFRGKVTL TVDRSSSAAY MELRSLTSED TAVYYCSRGL WDAMDSWGQG TSVTVSS            117

SEQ ID NO: 90           moltype = AA  length = 16
```

```
FEATURE                 Location/Qualifiers
REGION                  1..16
                        note = MF2913 CDR1
source                  1..16
                        mol_type = protein
                        organism = synthetic construct
SEQUENCE: 90
DYKMDWVKQS HGKSLE                                                         16

SEQ ID NO: 91           moltype = AA   length = 6
FEATURE                 Location/Qualifiers
REGION                  1..6
                        note = MF2913 CDR2
source                  1..6
                        mol_type = protein
                        organism = synthetic construct
SEQUENCE: 91
NQKFRG                                                                     6

SEQ ID NO: 92           moltype = AA   length = 8
FEATURE                 Location/Qualifiers
REGION                  1..8
                        note = MF2913 CDR3
source                  1..8
                        mol_type = protein
                        organism = synthetic construct
SEQUENCE: 92
GLWDAMDS                                                                   8

SEQ ID NO: 93           moltype = DNA   length = 382
FEATURE                 Location/Qualifiers
misc_feature            1..382
                        note = MF1847
source                  1..382
                        mol_type = other DNA
                        organism = synthetic construct
CDS                     20..382
SEQUENCE: 93
ggcccagccg gccatggccc aggtgcagct ggtggagtct gggggaggcg tggtccagcc          60
tgggaggtcc ctgagactct cctgtgcagc ctctggattc accttcagta gctatggcat         120
gcactgggtc cgccaggctc caggcaaggg gctggagtgg gtggcagtta tatcatatga         180
tggaagtaat aaatactatg cagactccgt gaagggccga ttcaccatct ccagagacaa         240
ttccaagaac acgctgtatc tgcaaatgaa cagcctgaga gctgaggaca cggccgtgta         300
ttactgtgca aaaggttggt ggcatccgct gctgtctggc tttgattatt ggggccaagg         360
taccctggtc accgtctcca gt                                                 382

SEQ ID NO: 94           moltype = AA   length = 121
FEATURE                 Location/Qualifiers
REGION                  1..121
                        note = Synthetic Construct
source                  1..121
                        mol_type = protein
                        organism = synthetic construct
SEQUENCE: 94
QVQLVESGGG VVQPGRSLRL SCAASGFTFS SYGMHWVRQA PGKGLEWVAV ISYDGSNKYY          60
ADSVKGRFTI SRDNSKNTLY LQMNSLRAED TAVYYCAKGW WHPLLSGFDY WGQGTLVTVS         120
S                                                                        121

SEQ ID NO: 95           moltype = AA   length = 5
FEATURE                 Location/Qualifiers
REGION                  1..5
                        note = MF1847 CDR1
source                  1..5
                        mol_type = protein
                        organism = synthetic construct
SEQUENCE: 95
SYGMH                                                                      5

SEQ ID NO: 96           moltype = AA   length = 17
FEATURE                 Location/Qualifiers
REGION                  1..17
                        note = MF1847 CDR2
source                  1..17
                        mol_type = protein
                        organism = synthetic construct
SEQUENCE: 96
VISYDGSNKY YADSVKG                                                        17

SEQ ID NO: 97           moltype = AA   length = 12
```

```
FEATURE                 Location/Qualifiers
REGION                  1..12
                        note = MF1847 CDR3
source                  1..12
                        mol_type = protein
                        organism = synthetic construct
SEQUENCE: 97
GWWHPLLSGF DY                                                          12

SEQ ID NO: 98           moltype = DNA   length = 370
FEATURE                 Location/Qualifiers
misc_feature            1..370
                        note = MF3001
source                  1..370
                        mol_type = other DNA
                        organism = synthetic construct
CDS                     20..370
SEQUENCE: 98
ggcccagccg gccatggccg aggtccagct gcagcagtct ggggctgaac tggcaaaacc      60
tggggcctca gtgaagctgt cctgcaagac ttctggctac aactttccta tctactggat    120
gcactgggta aaacagaggc ctggacgggg tctggaatgg attggataca ttaatcctag    180
tactggttat attaagaaca atcagaagtt caaggacaag gccaccttga ctgcagacaa    240
atccctcaac acagcctaca tgcagctgaa cagcctgaca tatgaggact ctgcagtcta    300
ttactgtaca agagaaggga taactgggtt tacttactgg ggccaaggga ctctggtcac    360
cgtctccagt                                                            370

SEQ ID NO: 99           moltype = AA   length = 117
FEATURE                 Location/Qualifiers
REGION                  1..117
                        note = Synthetic Construct
source                  1..117
                        mol_type = protein
                        organism = synthetic construct
SEQUENCE: 99
EVQLQQSGAE LAKPGASVKL SCKTSGYNFP IYWMHWVKQR PGRGLEWIGY INPSTGYIKN      60
NQKFKDKATL TADKSSNTAY MQLNSLTYED SAVYYCTREG ITGFTYWGQG TLVTVSS        117

SEQ ID NO: 100          moltype = AA   length = 16
FEATURE                 Location/Qualifiers
REGION                  1..16
                        note = MF3001 CDR1
source                  1..16
                        mol_type = protein
                        organism = synthetic construct
SEQUENCE: 100
IYWMHWVKQR PGRGLE                                                      16

SEQ ID NO: 101          moltype = AA   length = 6
FEATURE                 Location/Qualifiers
REGION                  1..6
                        note = MF3001 CDR2
source                  1..6
                        mol_type = protein
                        organism = synthetic construct
SEQUENCE: 101
NQKFKD                                                                  6

SEQ ID NO: 102          moltype = AA   length = 8
FEATURE                 Location/Qualifiers
REGION                  1..8
                        note = MF3001 CDR3
source                  1..8
                        mol_type = protein
                        organism = synthetic construct
SEQUENCE: 102
EGITGFTY                                                                8

SEQ ID NO: 103          moltype = DNA   length = 385
FEATURE                 Location/Qualifiers
misc_feature            1..385
                        note = MF1898
source                  1..385
                        mol_type = other DNA
                        organism = synthetic construct
CDS                     20..385
SEQUENCE: 103
ggcccagccg gccatggccc aggtgcagct ggtggagtct gggggaggcg tggtccagcc      60
tgggaggtcc ctgagactct cctgtgcagc ctctggattc accttcagta gctatggcat    120
gcactgggtc cgccaggctc caggcaaggg gctgagtgg gtggcagtta tacatatga     180
```

```
tggaagtaat aaatactatg cagactccgt gaagggccga ttcaccatct ccagagacaa    240
ttccaagaac acgctgtatc tgcaaatgaa cagcctgaga gctgaggaca cggccgtgta    300
ttactgtgca aaagatggtt tccgtcgtac tactctgtct ggctttgatt attggggcca    360
aggtaccctg gtcaccgtct ccagt                                          385
```

| | | |
|---|---|---|
| SEQ ID NO: 104 | moltype = AA  length = 122 | |
| FEATURE | Location/Qualifiers | |
| REGION | 1..122 | |
| | note = Synthetic Construct | |
| source | 1..122 | |
| | mol_type = protein | |
| | organism = synthetic construct | |

SEQUENCE: 104
```
QVQLVESGGG VVQPGRSLRL SCAASGFTFS SYGMHWVRQA PGKGLEWVAV ISYDGSNKYY    60
ADSVKGRFTI SRDNSKNTLY LQMNSLRAED TAVYYCAKDG FRRTTLSGFD YWGQGTLVTV   120
SS                                                                 122
```

| | | |
|---|---|---|
| SEQ ID NO: 105 | moltype = AA  length = 13 | |
| FEATURE | Location/Qualifiers | |
| REGION | 1..13 | |
| | note = MF1898 CDR3 | |
| source | 1..13 | |
| | mol_type = protein | |
| | organism = synthetic construct | |

SEQUENCE: 105
```
DGFRRTTLSG FDY                                                       13
```

| | | |
|---|---|---|
| SEQ ID NO: 106 | moltype = DNA  length = 379 | |
| FEATURE | Location/Qualifiers | |
| misc_feature | 1..379 | |
| | note = MF3003 | |
| source | 1..379 | |
| | mol_type = other DNA | |
| | organism = synthetic construct | |
| CDS | 20..379 | |

SEQUENCE: 106
```
ggcccagccg gccatggccc aggtgcagct gaagcagtct ggacctgagc tggtgaagcc    60
tggggcctca gtgaagattt cctgcaaggc ttctggcgac gcattcagtt actcctggat   120
gaactgggtg aagcagaggc ctggaaaggg tcttgagtgg attggacgga tttatcctgg   180
agatggagat attaactaca tgggaagttt caagggcaag gccacactga ctgcagacaa   240
atcctccagc acagcccacc tgcaactcaa cagcctgaca tctgaggact ctgcggtcta   300
cttctgtgca agaggacagc tcggactaga ggcctggttt gcttattggg gccaggggac   360
tctggtcacc gtctccagt                                                 379
```

| | | |
|---|---|---|
| SEQ ID NO: 107 | moltype = AA  length = 120 | |
| FEATURE | Location/Qualifiers | |
| REGION | 1..120 | |
| | note = Synthetic Construct | |
| source | 1..120 | |
| | mol_type = protein | |
| | organism = synthetic construct | |

SEQUENCE: 107
```
QVQLKQSGPE LVKPGASVKI SCKASGDAFS YSWMNWVKQR PGKGLEWIGR IYPGDGDINY    60
NGKFKGKATL TADKSSSTAH LQLNSLTSED SAVYFCARGQ LGLEAWFAYW GQGTLVTVSS   120
```

| | | |
|---|---|---|
| SEQ ID NO: 108 | moltype = AA  length = 16 | |
| FEATURE | Location/Qualifiers | |
| REGION | 1..16 | |
| | note = MF3003 CDR1 | |
| source | 1..16 | |
| | mol_type = protein | |
| | organism = synthetic construct | |

SEQUENCE: 108
```
YSWMNWVKQR PGKGLE                                                    16
```

| | | |
|---|---|---|
| SEQ ID NO: 109 | moltype = AA  length = 6 | |
| FEATURE | Location/Qualifiers | |
| REGION | 1..6 | |
| | note = MF3003 CDR2 | |
| source | 1..6 | |
| | mol_type = protein | |
| | organism = synthetic construct | |

SEQUENCE: 109
```
NGKFKG                                                                6
```

| | | |
|---|---|---|
| SEQ ID NO: 110 | moltype = AA  length = 11 | |
| FEATURE | Location/Qualifiers | |
| REGION | 1..11 | |
| | note = MF3003 CDR3 | |

```
source                    1..11
                          mol_type = protein
                          organism = synthetic construct
SEQUENCE: 110
GQLGLEAWFA Y                                                              11

SEQ ID NO: 111            moltype = DNA   length = 391
FEATURE                   Location/Qualifiers
misc_feature              1..391
                          note = MF6058
source                    1..391
                          mol_type = other DNA
                          organism = synthetic construct
CDS                       20..391
SEQUENCE: 111
ggcccagccg gccatggccc aggtgcagct ggtgcagtct ggggctgacg tgaagaagcc        60
tggggcctca gtgaaggtca cgtgcaaggc ttctggatac accttcaccg gctactatat       120
gcactgggtg cgacaggccc tggacaagtc tcttgagtgg atgggatgga tcaaccctca       180
aagtggtggc acaaactatg caaagaagtt tcagggcagg gtctctatga ccagggagac       240
gtccacaagc acagcctaca tgcagctgag caggctgaga tctgacgaca cggctacgta       300
ttactgtgca agagatcatg gttctcgtca tttctggtct tactggggct ttgattattg       360
gggccaaggt accctggtca ccgtctccag t                                      391

SEQ ID NO: 112            moltype = AA   length = 124
FEATURE                   Location/Qualifiers
REGION                    1..124
                          note = Synthetic Construct
source                    1..124
                          mol_type = protein
                          organism = synthetic construct
SEQUENCE: 112
QVQLVQSGAD VKKPGASVKV TCKASGYTFT GYYMHWVRQA PGQALEWMGW INPQSGGTNY        60
AKKFQGRVSM TRETSTSTAY MQLSRLRSDD TATYYCARDH GSRHFWSYWG FDYWGQGTLV       120
TVSS                                                                    124

SEQ ID NO: 113            moltype = AA   length = 17
FEATURE                   Location/Qualifiers
REGION                    1..17
                          note = MF6058 CDR2
source                    1..17
                          mol_type = protein
                          organism = synthetic construct
SEQUENCE: 113
WINPQSGGTN YAKKFQG                                                       17

SEQ ID NO: 114            moltype = AA   length = 15
FEATURE                   Location/Qualifiers
REGION                    1..15
                          note = MF6058 CDR3
source                    1..15
                          mol_type = protein
                          organism = synthetic construct
SEQUENCE: 114
DHGSRHFWSY WGFDY                                                         15

SEQ ID NO: 115            moltype = DNA   length = 391
FEATURE                   Location/Qualifiers
misc_feature              1..391
                          note = MF6061
source                    1..391
                          mol_type = other DNA
                          organism = synthetic construct
CDS                       20..391
SEQUENCE: 115
ggcccagccg gccatggccc aggtgcagct ggtgcagtct ggggctgagg tgaagaagcc        60
tggggcctca gtgaaggtct cctgcaaggc ttctggatac accttcaccg gctactatat       120
gcactgggtg cgacaggccc tggacaaggc ttgagtgg atgggatgga tcaaccctca         180
gagtggtggc acaaactatg cacagaagtt taagggcagg gtcacgatga ccagggacac       240
gtccaccagc acagcctaca tggagctgag caggctgaga tctgacgaca cggctgtgta       300
ttactgtgca agagatcatg gttctcgtca tttctggtct tactggggct ttgattattg       360
gggccaaggt accctggtca ccgtctccag t                                      391

SEQ ID NO: 116            moltype = AA   length = 124
FEATURE                   Location/Qualifiers
REGION                    1..124
                          note = Synthetic Construct
source                    1..124
                          mol_type = protein
                          organism = synthetic construct
```

```
SEQUENCE: 116
QVQLVQSGAE VKKPGASVKV SCKASGYTFT GYYMHWVRQA PGQGLEWMGW INPQSGGTNY   60
AQKFKGRVTM TRDTSTSTAY MELSRLRSDD TAVYYCARDH GSRHFWSYWG FDYWGQGTLV  120
TVSS                                                              124

SEQ ID NO: 117          moltype = AA   length = 17
FEATURE                 Location/Qualifiers
REGION                  1..17
                        note = MF6061 CDR2
source                  1..17
                        mol_type = protein
                        organism = synthetic construct
SEQUENCE: 117
WINPQSGGTN YAQKFKG                                                 17

SEQ ID NO: 118          moltype = DNA   length = 391
FEATURE                 Location/Qualifiers
misc_feature            1..391
                        note = MF6065
source                  1..391
                        mol_type = other DNA
                        organism = synthetic construct
CDS                     20..391
SEQUENCE: 118
ggcccagccg gccatggccc aggtgcagct ggtgcagtct ggggctgagg tgaagaagcc   60
tggggcctca gtgaaggtct cctgcaaggc ttctggatac accttcacct cttactatat  120
gcactgggtg cgacaggccc ctggacaagg gcttgagtgg atgggatgga tcaaccctca  180
gggggttct acaaactatg cacagaagtt tcagggcagg gtcacgatga ccagggacac  240
gtccaccagc acagtgtaca tggagctgag caggctgaga tctgaggaca cggctgtgta  300
ttactgtgca agagatcatg gttctcgtca tttctggtct tactggggct ttgattattg  360
gggccaaggt accctggtca ccgtctccag t                                 391

SEQ ID NO: 119          moltype = AA   length = 124
FEATURE                 Location/Qualifiers
REGION                  1..124
                        note = Synthetic Construct
source                  1..124
                        mol_type = protein
                        organism = synthetic construct
SEQUENCE: 119
QVQLVQSGAE VKKPGASVKV SCKASGYTFT SYYMHWVRQA PGQGLEWMGW INPQGGSTNY   60
AQKFQGRVTM TRDTSTSTVY MELSRLRSED TAVYYCARDH GSRHFWSYWG FDYWGQGTLV  120
TVSS                                                              124

SEQ ID NO: 120          moltype = AA   length = 5
FEATURE                 Location/Qualifiers
REGION                  1..5
                        note = MF6065 CDR1
source                  1..5
                        mol_type = protein
                        organism = synthetic construct
SEQUENCE: 120
SYMH                                                                5

SEQ ID NO: 121          moltype = AA   length = 17
FEATURE                 Location/Qualifiers
REGION                  1..17
                        note = MF6065 CDR2
source                  1..17
                        mol_type = protein
                        organism = synthetic construct
SEQUENCE: 121
WINPQGGSTN YAQKFQG                                                 17

SEQ ID NO: 122          moltype = AA   length = 124
FEATURE                 Location/Qualifiers
REGION                  1..124
                        note = MF6055
source                  1..124
                        mol_type = protein
                        organism = synthetic construct
SEQUENCE: 122
QVQLVQSGAD VKKPGASVKV SCKASGYTFT GYYMHWVRQA PGQALEWMGW INPSSGGTNY   60
AKKFQGRVTM TRETSTSTAY MELSRLRSDD TATYYCARDH GSRHFWSYWG FDYWGQGTLV  120
TVSS                                                              124
```

```
SEQ ID NO: 123          moltype = AA   length = 124
FEATURE                 Location/Qualifiers
REGION                  1..124
                        note = MF6056
source                  1..124
                        mol_type = protein
                        organism = synthetic construct
SEQUENCE: 123
QVQLVQSGAD VKKPGASVKV TCKASGYTFT GYYMHWVRQA PGQALEWMGW INPSSGGTNY      60
AKKFQGRVSM TRETSTSTAY MQLSRLRSDD TATYYCARDH GSRHFWSYWG FDYWGQGTLV     120
TVSS                                                                  124

SEQ ID NO: 124          moltype = AA   length = 124
FEATURE                 Location/Qualifiers
REGION                  1..124
                        note = MF6057
source                  1..124
                        mol_type = protein
                        organism = synthetic construct
SEQUENCE: 124
QVQLVQSGAD VKKPGASVKV TCKASGYTFT GYYMHWVRQA PGQGLEWMGW INPQSGGTNY      60
AQKFQGRVTM TRDTSISTAY MQLSRLRSDD TAVYYCARDH GSRHFWSYWG FDYWGQGTLV     120
TVSS                                                                  124

SEQ ID NO: 125          moltype = AA   length = 124
FEATURE                 Location/Qualifiers
REGION                  1..124
                        note = MF6059
source                  1..124
                        mol_type = protein
                        organism = synthetic construct
SEQUENCE: 125
QVQLVQSGAE VKKPGASVKV SCKASGYTFT GYYMHWVRQA PGQGLEWMGW INPGSGSTNY      60
AQKFQGRVTM TRDTSISTAY MELSRLRSDD TAVYYCARDH GSRHFWSYWG FDYWGQGTLV     120
TVSS                                                                  124

SEQ ID NO: 126          moltype = AA   length = 124
FEATURE                 Location/Qualifiers
REGION                  1..124
                        note = MF6060
source                  1..124
                        mol_type = protein
                        organism = synthetic construct
SEQUENCE: 126
QVQLVQSGAD VKKPGASVKV SCKASGYTFT GYYMHWVRQA PGQALEWMGW INPSGGTNY       60
AKKFQGRVTM TRETSTSTAY MELSRLRSDD TATYYCARDH GSRHFWSYWG FDYWGQGTLV     120
TVSS                                                                  124

SEQ ID NO: 127          moltype = AA   length = 124
FEATURE                 Location/Qualifiers
REGION                  1..124
                        note = MF6062
source                  1..124
                        mol_type = protein
                        organism = synthetic construct
SEQUENCE: 127
QVQLVQSGAE VKKPGASVKV SCKASGYTFT GYYMHWVRQA PGQGLEWMGW INPGSGSTNY      60
AQKFQGRVTM TRDTSTSTAY MELSRLRSDD TAVYYCARDH GSRHFWSYWG FDYWGQGTLV     120
TVSS                                                                  124

SEQ ID NO: 128          moltype = AA   length = 124
FEATURE                 Location/Qualifiers
REGION                  1..124
                        note = MF6063
source                  1..124
                        mol_type = protein
                        organism = synthetic construct
SEQUENCE: 128
QVQLVQSGAE VKKPGASVKV SCKASGYTFT GYYMHWVRQA PGQGLEWMGW INPQSGGTNY      60
AKKFQGRVTM TRDTSTSTAY MELSRLRSDD TAVYYCARDH GSRHFWSYWG FDYWGQGTLV     120
TVSS                                                                  124

SEQ ID NO: 129          moltype = AA   length = 124
FEATURE                 Location/Qualifiers
REGION                  1..124
                        note = MF6064
```

```
source              1..124
                    mol_type = protein
                    organism = synthetic construct
SEQUENCE: 129
QVQLVQSGAE VKKPGASVKV SCKASGYTFT GYYMHWVRQA PGKGLEWMGW INPQSGGTNY    60
AQKFQGRVTM TRDTSTSTAY MELSRLRSDD TAVYYCARDH GSRHFWSYWG FDYWGQGTLV   120
TVSS                                                                124

SEQ ID NO: 130      moltype = AA  length = 124
FEATURE             Location/Qualifiers
REGION              1..124
                    note = MF6066
source              1..124
                    mol_type = protein
                    organism = synthetic construct
SEQUENCE: 130
QVQLVQSGAE VKKPGASVKV SCKASGYTFT GYYMHWVRQA PGQGLEWMGW INPQSGSTNY    60
AQKFQGRVTM TRDTSTSTAY MELSSLRSED TAVYYCARDH GSRHFWSYWG FDYWGQGTLV   120
TVSS                                                                124

SEQ ID NO: 131      moltype = AA  length = 124
FEATURE             Location/Qualifiers
REGION              1..124
                    note = MF6067
source              1..124
                    mol_type = protein
                    organism = synthetic construct
SEQUENCE: 131
QVQLVQSGAE VKKPGASVKV SCKASGYTFT GYYMHWVRQA PGQGLEWMGW INPQSGGTNY    60
AQKFQGRVTM TRDTSTSTAV MELSSLRSDD TAVYYCARDH GSRHFWSYWG FDYWGQGTLV   120
TVSS                                                                124

SEQ ID NO: 132      moltype = AA  length = 124
FEATURE             Location/Qualifiers
REGION              1..124
                    note = MF6068
source              1..124
                    mol_type = protein
                    organism = synthetic construct
SEQUENCE: 132
QVQLVQSGAE VKKPGASVKV SCKASGYTFT GYYMHWVRQA PGQGLEWMGW INPQSGGTNY    60
AQKFQGRVTM TRDTSTSTAY MELSRLRSDD TAVYYCARDH GSRHFWSYWG FDYWGQGTLV   120
TVSS                                                                124

SEQ ID NO: 133      moltype = AA  length = 124
FEATURE             Location/Qualifiers
REGION              1..124
                    note = MF6069
source              1..124
                    mol_type = protein
                    organism = synthetic construct
SEQUENCE: 133
QVQLVQSGAE VKKPGASVKV SCKASGYTFT GYYMHWVRQA PGQGLEWMGW INPQSGGTNY    60
AQKFQGRVTM TRDTSISTAY MELSRLRSDD TAVYYCARDH GSRHFWSYWG FDYWGQGTLV   120
TVSS                                                                124

SEQ ID NO: 134      moltype = AA  length = 124
FEATURE             Location/Qualifiers
REGION              1..124
                    note = MF6070
source              1..124
                    mol_type = protein
                    organism = synthetic construct
SEQUENCE: 134
QVQLVQSGAE VKKPGASVKV SCKASGYTFT SYYMHWVRQA PGQGLEWMGW INPSGGTNY     60
AQKFQGRVTM TRDTSTSTVY MELSRLRSED TAVYYCARDH GSRHFWSYWG FDYWGQGTLV   120
TVSS                                                                124

SEQ ID NO: 135      moltype = AA  length = 124
FEATURE             Location/Qualifiers
REGION              1..124
                    note = MF6071
source              1..124
                    mol_type = protein
                    organism = synthetic construct
SEQUENCE: 135
QVQLVQSGAE VKKPGASVKV SCKASGYTFT GYYMHWVRQA PGQGLEWMGW INPSSGSTNY    60
AQKFQGRVTM TRDTSTSTAY MELSSLRSED TAVYYCARDH GSRHFWSYWG FDYWGQGTLV   120
TVSS                                                                124
```

```
SEQ ID NO: 136          moltype = AA   length = 124
FEATURE                 Location/Qualifiers
REGION                  1..124
                        note = MF6072
source                  1..124
                        mol_type = protein
                        organism = synthetic construct
SEQUENCE: 136
QVQLVQSGAE VKKPGASVKV SCKASGYTFT GYYMHWVRQA PGQGLEWMGW INPSSGGTNY   60
AQKFQGRVTM TRDTSTSTVY MELSSLRSDD TAVYYCARDH GSRHFWSYWG FDYWGQGTLV  120
TVSS                                                               124

SEQ ID NO: 137          moltype = AA   length = 124
FEATURE                 Location/Qualifiers
REGION                  1..124
                        note = MF6073
source                  1..124
                        mol_type = protein
                        organism = synthetic construct
SEQUENCE: 137
QVQLVQSGAE VKKPGASVKV SCKASGYTFT GYYMHWVRQA PGQGLEWMGW INPSSGGTNY   60
AQKFQGRVTM TRDTSTSTAY MELSRLRSDD TAVYYCARDH GSRHFWSYWG FDYWGQGTLV  120
TVSS                                                               124

SEQ ID NO: 138          moltype = AA   length = 124
FEATURE                 Location/Qualifiers
REGION                  1..124
                        note = MF6074
source                  1..124
                        mol_type = protein
                        organism = synthetic construct
SEQUENCE: 138
QVQLVQSGAE VKKPGASVKV SCKASGYTFT GYYMHWVRQA PGQGLEWMGW INPSSGGTNY   60
AQKFQGRVTM TRDTSISTAY MELSRLRSDD TAVYYCARDH GSRHFWSYWG FDYWGQGTLV  120
TVSS                                                               124

SEQ ID NO: 139          moltype = AA   length = 121
FEATURE                 Location/Qualifiers
REGION                  1..121
                        note = MF2971 Synthetic Construct
source                  1..121
                        mol_type = protein
                        organism = synthetic construct
SEQUENCE: 139
QVQLKQSGAE LVRPGASVKL SCKASGYTFT AYYINWVKQR PGQGLEWIAR IYPGSGYTYY   60
NEIFKGRATL TADESSSTAY MQLSSLTSED SAVYFCARPP VYYDSAWFAY WGQGTLVTVS  120
S                                                                  121

SEQ ID NO: 140          moltype = AA   length = 16
FEATURE                 Location/Qualifiers
REGION                  1..16
                        note = MF2916 CDR1
source                  1..16
                        mol_type = protein
                        organism = synthetic construct
SEQUENCE: 140
GYYINWVKQR PGQGLE                                                   16

SEQ ID NO: 141          moltype = AA   length = 6
FEATURE                 Location/Qualifiers
REGION                  1..6
                        note = MF2916 CRD2
source                  1..6
                        mol_type = protein
                        organism = synthetic construct
SEQUENCE: 141
NEKFKG                                                              6

SEQ ID NO: 142          moltype = AA   length = 121
FEATURE                 Location/Qualifiers
REGION                  1..121
                        note = MF3031 Synthetic Construct
source                  1..121
                        mol_type = protein
                        organism = synthetic construct
```

```
SEQUENCE: 142
QVQLQQSGAE LVRPGASVKL SCKASGYTFT AYYINWVKQR PGQGLEWIAK IYPGSGYTYY        60
NENFRGKATL TAEESSSTAY IQLSSLTSED SAVYFCARGV YDYDGAWFAY WGQGTLVTVS       120
S                                                                      121

SEQ ID NO: 143          moltype = AA  length = 124
FEATURE                 Location/Qualifiers
REGION                  1..124
                        note = MF3163 Synthetic Construct
source                  1..124
                        mol_type = protein
                        organism = synthetic construct
SEQUENCE: 143
QVQLVQSGAE VKKPGASVKV SCKASGYTFT GYYMHWVRQA PGQGLEWMGW INPNSGGTNY        60
AQKFQGRVTM TRDTSISTAY MELSRLRSDD TAVYYCAKDS YSRHFYSWWA FDYWGQGTLV       120
TVSS                                                                   124

SEQ ID NO: 144          moltype = AA  length = 5
FEATURE                 Location/Qualifiers
REGION                  1..5
                        note = MF3163 CDR1
source                  1..5
                        mol_type = protein
                        organism = synthetic construct
SEQUENCE: 144
GYYMH                                                                    5

SEQ ID NO: 145          moltype = AA  length = 5
FEATURE                 Location/Qualifiers
REGION                  1..5
                        note = MF3307 CDR1
source                  1..5
                        mol_type = protein
                        organism = synthetic construct
SEQUENCE: 145
GYYMH                                                                    5

SEQ ID NO: 146          moltype = AA  length = 5
FEATURE                 Location/Qualifiers
REGION                  1..5
                        note = MF1898 CDR1
source                  1..5
                        mol_type = protein
                        organism = synthetic construct
SEQUENCE: 146
SYGMH                                                                    5

SEQ ID NO: 147          moltype = AA  length = 17
FEATURE                 Location/Qualifiers
REGION                  1..17
                        note = MF1898 CDR2
source                  1..17
                        mol_type = protein
                        organism = synthetic construct
SEQUENCE: 147
VISYDGSNKY YADSVKG                                                      17

SEQ ID NO: 148          moltype = AA  length = 5
FEATURE                 Location/Qualifiers
REGION                  1..5
                        note = MF6058 CDR1
source                  1..5
                        mol_type = protein
                        organism = synthetic construct
SEQUENCE: 148
GYYMH                                                                    5

SEQ ID NO: 149          moltype = AA  length = 5
FEATURE                 Location/Qualifiers
REGION                  1..5
                        note = MF6061 CDR1
source                  1..5
                        mol_type = protein
                        organism = synthetic construct
SEQUENCE: 149
GYYMH                                                                    5

SEQ ID NO: 150          moltype = AA  length = 15
FEATURE                 Location/Qualifiers
```

```
REGION                1..15
                      note = MF6061 CDR3
source                1..15
                      mol_type = protein
                      organism = synthetic construct
SEQUENCE: 150
DHGSRHFWSY WGFDY                                                           15

SEQ ID NO: 151        moltype = AA  length = 15
FEATURE               Location/Qualifiers
REGION                1..15
                      note = MF6065 CDR3
source                1..15
                      mol_type = protein
                      organism = synthetic construct
SEQUENCE: 151
DHGSRHFWSY WGFDY                                                           15
```